United States Patent
Melnick et al.

(10) Patent No.: US 9,913,870 B2
(45) Date of Patent: Mar. 13, 2018

(54) METHOD FOR STIMULATING AMP-ACTIVATED PROTEIN KINASE

(71) Applicants: DHARMA BIOMEDICAL, LLC, Miami, FL (US); FLAVEX NATUREXTRAKTE GMBH, Rehlingen (DE)

(72) Inventors: Steven J. Melnick, Coral Gables, FL (US); Karl-Werner Quirin, Beckingen (DE); Cheppail Ramachandran, Miami, FL (US); Melvin Rothberg, Weston, FL (US)

(73) Assignees: DHARMA BIOMEDICAL, LLC, Miami, FL (US); FLAVEX NATUREXTRAKTE GMBH (DE)

( * ) Notice: Subject to any disclaimer, the term of this patent is extended or adjusted under 35 U.S.C. 154(b) by 705 days.

(21) Appl. No.: 14/368,888

(22) PCT Filed: Jan. 11, 2013

(86) PCT No.: PCT/US2013/021142
§ 371 (c)(1),
(2) Date: Jun. 26, 2014

(87) PCT Pub. No.: WO2013/106647
PCT Pub. Date: Jul. 18, 2013

(65) Prior Publication Data
US 2015/0010615 A1 Jan. 8, 2015

Related U.S. Application Data

(60) Provisional application No. 61/618,311, filed on Mar. 30, 2012, provisional application No. 61/615,084, filed on Mar. 23, 2012, provisional application No. 61/586,553, filed on Jan. 13, 2012.

(51) Int. Cl.
| | | |
|---|---|---|
| *A61K 36/328* | (2006.01) | |
| *A61K 8/97* | (2017.01) | |
| *A61Q 19/08* | (2006.01) | |
| *A61Q 19/00* | (2006.01) | |

(52) U.S. Cl.
CPC .............. *A61K 36/328* (2013.01); *A61K 8/97* (2013.01); *A61Q 19/004* (2013.01); *A61Q 19/08* (2013.01)

(58) Field of Classification Search
CPC .................................................... A61K 36/328
USPC ......................................................... 424/748
See application file for complete search history.

(56) References Cited

U.S. PATENT DOCUMENTS

| | | | |
|---|---|---|---|
| 5,972,341 A * | 10/1999 | Andre ...................... A61K 8/35 424/401 |
| 6,630,177 B1 * | 10/2003 | Andre ...................... A61K 8/35 424/748 |
| 7,361,370 B2 * | 4/2008 | Bombardelli .......... A61K 31/11 424/725 |
| 8,574,637 B2 | 11/2013 | Minatelli et al. |
| 8,586,104 B2 | 11/2013 | Minatelli et al. |
| 8,652,544 B2 | 2/2014 | Minatelli et al. |
| 2002/0001599 A1 * | 1/2002 | Neubourg .............. A61K 8/046 424/400 |
| 2002/0061929 A1 * | 5/2002 | Majeed .................. C07C 69/734 514/532 |
| 2006/0051435 A1 * | 3/2006 | Udell ...................... A23L 33/20 424/725 |
| 2006/0104916 A1 | 5/2006 | Shekunov et al. |
| 2006/0193928 A1 * | 8/2006 | Soman ................. A61K 36/185 424/725 |
| 2008/0015336 A1 * | 1/2008 | Cornish ............. B01D 11/0203 528/498 |
| 2008/0317795 A1 * | 12/2008 | Traynor ................. A61K 8/062 424/401 |
| 2012/0213874 A1 * | 8/2012 | Mitra ................... A61K 36/328 424/756 |
| 2012/0237621 A1 * | 9/2012 | Brandt ................. A61K 36/328 424/748 |
| 2013/0059768 A1 * | 3/2013 | Hallaraker .......... A61K 31/683 514/1.1 |

OTHER PUBLICATIONS

Sahena et al. J. Food Engineering. 2009. vol. 95, pp. 240-253.*
Quirin, KW. Euro Cosmetics. 2011, vol. 19. One-page KOSMET Abstract.*
Starmans et al. Trends in Food Sci and Tech. 1996. vol. 7, pp. 191-197.*
Agarwal R et al., "Clinical trials with guggulipid—A new hypolipidemic agent of plant origin in primary hyperlipidemia" *Indian Journal of Medical Research*, 1986, 84:626-634. [Abstract].
Artaria C et al., "Lifting properties of the alkamide fraction from the fruit husks of Zanthoxylum bungeanum" *International Journal of Cosmetic Science*, 2011, 33:328-333.
Ashida Y et al. "Effect of coenzyme $Q_{10}$ as a supplement on wrinkle reduction" *Food Style 21*, 2004, 8(6):1-4.

(Continued)

*Primary Examiner* — Chris R Tate
(74) *Attorney, Agent, or Firm* — Saliwanchik, Lloyd & Eisenschenk

(57) ABSTRACT

The subject invention pertains to supercritical carbon dioxide extracts of *Commiphora mukul* resin (guggul), which can be modified or not modified by some ethanol addition; methods for their production; and methods of use, such as inhibiting HMG-CoA reductase, inhibiting transformation of pre-adipocytes to adipocytes, inhibiting triglyceride storage, promoting insulin sensitivity in adipocytes, treatment of disorders (for example, hypercholesterolemia, hyperlipidemia, hyperglycemia, obesity, metabolic syndrome, cardiovascular disease, atherosclerotic heart disease, autoimmune disorder, insulin resistance, leptin resistance, arthritis, cell proliferation disorder, such as cancer and atherosclerosis; damaged skin, sores, cuts, rashes, bruises, dryness, burns, sunburn, radiation burn, and infection), and regulating or suppressing appetite.

29 Claims, 36 Drawing Sheets

(56) References Cited

OTHER PUBLICATIONS

Chander R et al., "Cardioprotective Activity of Synthetic Guggulsterone (E and Z-Isomers) in Isoproterenol Induced Myocardial Isehemia in Rats: A comparative Study," *Indian Journal of Clinical Biochemistry*, 2003, 18(2)71-79.

Chen T-Q et al., "Supercritical fluid CO2 extraction, simultaneous determination of components in ultra-fine powder of Ganoderma sinense by HPLC-ESI-MS method" *Journal of the Taiwan Institute of Chemical Engineers*, 2011, 42:428-434.

Goldstein JL and Brown MS, "Regulation of the mevalonate pathway" *Nature*, 1990, 343:425-430.

Gopal K et al., "Clinical trial of ethyl acetate extract of gum gugulu (gugulipid) in primary hyperlipidemia" *Journal of the Association of Physicians of India*, 1986, 34(4):249-251. [Abstract].

Hoppe U et al., "Coenzyme $Q_{10}$, a cutaneous antioxidant and energizer" *BioFactors*, 1999, 9:371-378.

Inui M et al., "Mechanisms of inhibitory effects of $CoQ_{10}$ on UVB-induced wrinkle formation in vitro and in vivo" *BioFactors*, 2008, 32(1-4):237-243. [Abstract].

Izzat NN et al., "New Molecular Targets for Cholesterol-Lowering Therapy" *The Journal of Pharmacology and Experimental Therapeutics*, 2000, 293(2):315-320.

Kang TH et al., "Effects of red ginseng extract on UVB irradiated-induced skin aging in hairless mice" *Journal of Ethnopharmacology*, 2009, 123:446-451.

Kimura I et al., "New Triterpenes, Myrrhanol A and Myrrhanone A, from Guggul-Gum Resins, and their Potent Anti-Inflammatory Effect on Adjuvant-Induced Air-Pouch Granuloma of Mice" *Bioorganic & Medicinal Chemistry Letters*, 2001, 11:985-989.

Muta-Takada K et al., "Coenzyme $Q_{10}$ protects against oxidative stress-induced cell death and enhances the synthesis of basement membrane components in dermal and epidermal cells" *BioFactors*, 2009, 35(5):435-441.

Nityanand S et al., "Clinical trials with guggulipid. A new hypolipidemic agent" *Journal of the Association of Physicians of India*, 1989, 37(5):323-328. [Abstract].

Nityanand S et al., "Clinical trials with guggulipid. A New Hypolipidemic Agent" *Journal of the Association of Physicians of India*, 1987, 149-161.

Prahl S et al., "Aging skin is functionally anaerobic: Importance of coenzyme $Q_{10}$ for anti aging skin care" *BioFactors*, 2008, 32:245-255.

Quirin K-W, "Phytosterol-rich Extracts and Anti-Aging Benefits" *Euro Cosmetics*, 2011, 19:16-18.

Quirin K-W, "Phytosterol-Rich Soy Germ and Guggul Extracts Provide Anti-Ageing Benefits," *Cosmetic Science Technology*, 2011, pp. 18-24.

Ramachandran C et al., "Protective and restorative effects of a Commiphora mukul gum resin and triheptoanoin preparation on the CCL-110 skin fibroblast cell line" *International Journal of Cosmetic Science*, 2012, 34(2):155-160.

Ramachandran C et al., "Hypolipidemic Effects of a Proprietary Commiphora Mukul Gum Resin Extract and Medium-Chain Triglyceride Preparation (GU-MCT810)" *Journal of Evidence-Based Complementary & Alternative Medicine*, 2013, 18(4):248-256.

Rizzo G et al., "The Farnesoid X Receptor Promotes Adipocyte Differentiation and Regulates Adipose Cell Function in Vivo" *Molecular Pharmacology*, 2006, 70(4):1164-1173.

Sharma B et al., "Effects of guggulsterone isolated from Commiphora mukul in high fat diet induced diabetic rats" *Food and Chemical Toxicology*, 2009, 47:2631-2639.

Shishodia S and Aggarwal BB, "Guggulsterone Inhibits NF—κB and IκBα Kinase Activation, Suppresses Expression of Anti-apoptotic Gene Products, and Enhances Apoptosis" *The Journal of Biological Chemistry*, 2004, 279:47148-47158.

Shishodia S et al., "The Guggul for Chronic Diseases: Ancient Medicine, Modern Targets" *Anticancer Research*, 2008, 28:3647-3664.

Song J-J et al., "Guggulsterone suppresses LPS induced inflammation of human middle ear epithelial cells (HMEEC)" *International Journal of Pediatric Otorhinolarngology*, 2010, 74:1384-1387.

Sumien N et al., "Prolonged Intake of Coenzyme $Q_{10}$ Impairs Cognitive Functions in Mice[1-3]" *The Journal of Nutrition*, 2009, 139:1926-1932.

Urizar N L et al., "A Natural Product That Lowers Cholesterol as an Antagonist Ligand for FXR" *Science*, 2002, 296(5573):1703-1706.

Wilke Resources, Inc., GlucodOX(TM) Product Information, Oct. 13, 2011, http://web.archive.org/web/20111013115340/ http://wilkeresources.com/product-GlucodOX.html.

Wu J et al., "The Hypolipidemic Natural Product Guggulsterone Acts as an Antagonist of the Bile Acid Receptor" *Molecular Endocrinology*, 2002, 16(7):1590-1597.

Yang J-Y et al., "Guggulsterone Inhibits Adipocyte Differentiation and Induces Apoptosis in 3T3-L1 cells" *Obesity*, 2008, 16(1):16-22.

Vagbhata, Astanga Samgraha—(commentary by Indu)part-1, 06(page No. 04-09), ( Ref.pg. No. of publication:195 ), 1991, Central Council for Research in Ayurveda & Siddha, New Delhi, India.†

Ali Ibn-e-Abbaas Majoosi, Kaamil-al-Sena'ah Part II(10th century AD), 06 (page No. 10-15), ( Ref.pg. No. of publication:409 ), 2005 AD, Central Council for Research in Unani Medicine, New Delhi, India.†

Mohammad Akbar Arzani, Qaraabaadeen Qaadri (17th century AD), 05 (page No. 16-20), ( Ref.pg. No. of publication:419 ), 1968 AD, Ahmadi Publication, Delhi, India.†

\* cited by examiner
† cited by third party

METHOD FOR STIMULATING AMP-ACTIVATED PROTEIN KINASE

CROSS-REFERENCE TO RELATED APPLICATIONS

The present application is the National Stage of International Application No. PCT/US2013/021142, filed Jan. 11, 2013, which claims the benefit of U.S. Provisional Application Ser. No. 61/586,553, filed Jan. 13, 2012; U.S. Provisional Application Ser. No. 61/615,084, filed Mar. 23, 2012; and U.S. Provisional Application Ser. No. 61/618,311, filed Mar. 30, 2012, each of which is hereby incorporated by reference herein in its entirety, including any figures, tables, nucleic acid sequences, amino acid sequences, or drawings.

BACKGROUND OF THE INVENTION

Guggul is a type of myrrh derived from *Commiphora mukul*, a small tree of the Bursaceae family native to India, Pakistan and Bangladesh. The gum resin (guggul) has been traditionally used in Ayurveda for its hypolipidemic, hypocholesterolemic, anticancer, anti-diabetic and anti-inflammatory effects. These claims are supported by modern in vitro assays and some aspects could be confirmed in clinical trials. A review of guggul for chronic diseases is provided in Shishodia et al., "The Guggul for chronic diseases: Ancient medicine, modern targets. *Anticancer Research*, 2008, 28: 3647-3664.

BRIEF SUMMARY OF THE INVENTION

The present invention concerns supercritical $CO_2$ *Commiphora mukul* extracts and compositions containing them, and methods for their use. The inventors have produced and identified such compositions capable of supporting biological mechanisms such as glucose metabolism, cholesterol metabolism with cholesterol levels within the normal range, blood lipid metabolism, mitochondrial biogenesis (supporting the creation of new energy-producing mitochondria), and primary energy production. These beneficial mechanisms can facilitate health by promoting cellular glucose uptake; supporting cholesterol levels already within the normal range (e.g., through regulation of HMG-CoA reductase); regulating transformation of pre-adipocytes to adipocytes, and regulating triglyceride storage; and stimulating AMP-activated protein kinase (AMPK), the nutrient/energy sensor researched for its role in supporting energy levels in cells throughout the body (and a pharmacologic target for helping in the transport of glucose) and thus providing all of the beneficial downstream effects that arise from AMPK activation.

A special guggul extract was obtained by supercritical $CO_2$-extraction with a small amount of ethanol as co-solvent. The resulting extract is standardized with triheptanoin to give a light brownish, clear, oily liquid which is easy to use. Triheptanoin is a stable odd chain triglyceride offering high spreadability and good skin feel without a greasy character. The product is derived from castor oil and, due to its natural origin, meets Ecocert criteria and is suitable for the natural cosmetics concept. It is used as well in supplements especially for anaplerotic therapy of people with metabolic defects regarding ATP and energy production in consequence of mitochondrial fat oxidation disorders. The formulation of supercritical guggul extract with triheptanoin can improve guggul efficacy and bioavailability in many respects.

Supercritical $CO_2$ extraction dissolves no gum or carbohydrates and only part of the guggul resin. The purified supercritical extract represents 15-20% of the starting material and has a complex composition. Besides some volatile mono- and sesquiterpenes like myrcene and caryophyllene, there are diterpenes of the cembrene type such as cembrene A and mukulol (allylcembrol), triterpenes of the polypodane type such as myrrhanol and myrrhanone derivatives, pregnane-type guggulsterones, higher alcohols as well as guggulsterols and guggullignans. This makes analysis a demanding task, especially since reference substances are scarcely available. In a preferred embodiment, the formulation is standardized to 2% guggulsterones (e.g., by HPLC).

In addition to publications referring to internal application of guggul extracts focusing on reduction of plasma cholesterol and lipids as well as on anti-diabetic effects and anti-cancer effects, there are positive results reported for topical application in cosmetics and dermatology. These include efficacy against acne, dermatitis, impure skin and an oily face. Anti-sebum and cleansing properties are mentioned as well as the reduction of wrinkles. It has been shown that guggulsterones suppress activation of matrix metalloproteinases, especially MMP-9 which is associated with the degradation of type IV and V collagens (Shishodia S. et al., "Guggulsterone inhibits NF-kappaB and IkappaBalpha kinase activation, suppresses expression of anti-apoptotic gene products, and enhances apoptosis," *J. Biol. Chem.*, 2004, 279: 47148-47158). This means reduced breakdown of the extracellular matrix (ECM) which provides structural support to human cells and is essential for processes like wound healing and the development of fibrous connective tissue.

Using in vitro assays, the inventors have demonstrated that the supercritical guggul extracts of the invention have anti-adipogenic efficacy by inhibition of pre-adipocyte differentiation and stimulation of lipolytic enzymes resulting in reduced formation of adipose tissue. These two mechanisms suggest that guggul extract contributes to the formation of a firm, even and smooth skin surface and alleviates wrinkle formation The supercritical extract possesses properties making it useful for anti-inflammatory and anti-aging applications. A subtle increase of chronic inflammation level is a characteristic of skin aging. Inflammation is caused by activation of signal pathways such as nuclear factor kappaB (NF-KB) by various intrinsic (dysfunctions as a consequence of aging) and extrinsic (exposition to polluting chemicals, smoke, UV-radiation) impacts. A consequence is the release of inflammatory mediators such as pro-inflammatory cytokines, the expression of MMPs and the stimulation of cyclooxygenase enzymes (COX-2) which mediate the production of proinflammatory prostaglandins (PEG2). It could be demonstrated that guggulsterones are able to down-regulate and balance this cascade of inflammatory events (Song J. J. et al., "Guggulsterone suppresses LPS induced inflammation of human middle ear epithelial cells (HMEEC), "*Int. J. Pediatr. Otorhinolaryngol,*" 2010, 74(12):1384-7), and that myrrhanol has also significant anti-inflammatory effect (Kimura I. et al., "New triterpenes, myrrhanol A and myrrhanone A, from guggul-gum resins, and their potent anti-inflammatory effect on adjuvant-induced air-pouch granuloma of mice," *Bioorganic & Medicinal Chemistry Letters,* 2001, 11(8): 985-989). Inflammation is often affiliated with damaging free radicals and oxidative stress. In this regard, guggul constituents like cembrenoids, lignans and sterones make a positive impact as well (Chander R. et al., "Antioxidant activity of guggulsterone, the active principal of guggulipid from *Commiphora mukul*," *J. Med. Arom. Plant Sci.*, 2002, 24: 370-374).

Another aspect of guggul is its ability to stimulate AMPK-activated protein kinase (AMPK), which up-regulates cellular energy production by phosphorylation of key enzymes in metabolic pathways. Normally, AMPK activation is achieved by exercise and physical training. AMPK stimulation, which also has significance for type 2 diabetic conditions, could be demonstrated for supercritical guggul extract and the guggul-triheptanoin formulation in a cell free kinase test. The results were confirmed by a cell based bio-assay (Quirin K.-W., "Phytosterol-Rich Soy Germ and Guggul Extracts Provide Anti-Aging Benefits," *Cosmetic Science Technology*, March 2011, pp. 18-24, which is incorporated herein by reference in its entirety).

The skin is the largest human organ. The metabolically active deeper skin layers are responsible for ongoing skin regeneration and for hair growth functionality. With advancing age and impaired signal transduction pathways, a slow-down of mitochondrial function and accordingly energy metabolism is observed. This process is considered a key factor in the modern theory of skin aging. Such conditions highly benefit from AMPK activation, which plays a major role in boosting cellular energy and improving the overall energy balance by enhancing mitochondrial activity and capacity. AMPK stimulation influences a whole cascade of processes upstream and downstream. In particular, it switches on catabolic pathways which generate ATP and switches off ATP consuming actions on a cellular level and beyond. Therefore, guggul extract may be used as an effective anti-aging agent for the skin and probably as a hair growth stimulant due to its AMPK activity. The rejuvenating effect is supported by anti-oxidative, anti-inflammatory and anti-wrinkle properties. While guggul is a relatively new approach for regenerative skin treatment, other ingredients intended to stimulate the skin's energy metabolism, especially coenzyme Q10 (ubiquinone), are already well established in anti-aging cosmetic products (Prahl S. et al., "Ageing skin is functionally anaerobic: importance of coenzyme Q10 for anti ageing skin care," *Biofactors*, 2008, 32(1-4): 245-55). Guggul has a similar intention but is directed towards more complex targets on a cellular level.

With increasing longevity and the numbers of people in the 40+ generation, cosmetic ingredients providing anti-aging benefits are a big trend. Looking good strengthens one's self-esteem, improves the quality of life and social integration. Another emerging trend is natural ingredients which are conforming to the different standards that have been established today. The guggul extract compositions of the invention fulfill these requirements and may be used for the creation of cosmetic products that inhibit photo-aging, act against degenerative skin conditions and restore a healthy skin function.

One aspect of the invention concerns a composition comprising a supercritical $CO_2$ extract of *Commiphora mukul* resin (guggul), wherein the supercritical carbon dioxide extraction is optionally modified by some ethanol addition.

Optionally, in addition to the supercritical carbon dioxide extract, the composition further comprises an oil (natural or synthetic). In some embodiments, the oil comprises one or more medium chain triglycerides (MCTs). For example, the oil may be one or more triglycerides comprise C8 and C10 fatty acids (e.g., caprylic/capric triglyceride). In some embodiments, the oil comprises triheptanoin. The properties of the guggul extracts can be enhanced by MCTs, which gain rapid access to the mitochondria (energy producing organelle in cells); are more quickly and efficiently burned as fuel for energy; and are not susceptible to fat storage like long chain fatty acids and long chain triglycerides (LTCs). Given their high energy density, rapid rate of absorption, and quick metabolic conversion into cellular energy, MCTs have been used as an effective supplement for fueling physical exertion. MCTs, can be quickly mobilized in the post-exercise recovery phase to rebuild muscles and prevent the breakdown of proteins (catabolism) that can occur when the body exerts a maximum demand on its energy reserves.

Other examples of oil(s) that may be included in the composition are olive oil, chia seed oil, soy germ oil, pomegranate oil (seed, pericarp, fruit), fish oil, and seafood oil (e.g., hill oil). In some embodiments, the composition comprises triheptanoin with or without other medium chain triglycerides.

In some embodiments, the composition comprises at least 0.1% guggulsterone (total E and/or Z guggulsterones). In some embodiments, the composition comprises at least 1% guggulsterone. In some embodiments, the composition comprises 0.1%-5% guggulsterone (total E and/or Z guggulsterones). In some embodiments, the composition comprises 1%-5% guggulsterone (total E and/or Z guggulsterones). In some embodiments, the composition comprises 1.5%-3% guggulsterone (total E and/or Z guggulsterones). In some embodiments, the composition comprises about 0.1% to about 2% guggulsterone (total E and/or Z guggulsterones, e.g., about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% guggulsterone, or an increment in between).

In some embodiments, the composition comprises 1.9%-2.1% guggulsterones (e.g., by HPLC); 6%-9% phytosterol (e.g., sitosterol); essential oil; cembrene; mukulol (allycembrol); and less than 3% ethanol.

Optionally, the composition can include one or more additional agents, such as a botanical extract, mineral, vitamin, nutrient, other nutraceutical, dietary supplement, or active pharmaceutical ingredient. In some embodiments, the composition includes an additional botanical extract selected from among a sterol, sterone, steroid, polyphenol, flavonoid, terpenoid, alkaloid, or a polysaccharide.

The composition may be formulated for any delivery (administration) route to a subject. For example, the formulation may be a solid (such as a powder) or a liquid. In some embodiments, the formulation is an oral formulation for ingestion or a topical formulation for the skin. In some embodiments, the composition is 100% natural. The composition of the invention may be made using methods described herein.

In some embodiments, the composition of the invention is GU-MCT810, which is a nutraceutical ingredient complex that includes a supercritical carbon dioxide *Commiphora mukul* extract and a medium chain triglyceride (MCT) oil composed of C8 and C10 fatty acids. GU-MCT810 contains guggulsterones (preferably standardized to 2.0%, (e.g., by HPLC analysis), which have been linked to several mechanisms that support lipid metabolism, glucose metabolism, and cellular energy.

In some other embodiments, the composition of the invention is GU-TC7, which is a nutraceutical ingredient complex that includes a supercritical carbon dioxide *Commiphora mukul* extract and triheptanoin. GU-TC7 has been shown to enhance energy production, and promote healthy blood glucose and blood lipids.

Another aspect of the invention concerns a method for treating or delaying the onset of a disorder in a subject, comprising administering an effective amount of the composition of the invention to the subject. In some embodiments, the composition is an oral formulation, and the disorder is hypercholesterolemia, hyperlipidemia, hyperglycemia, obesity, metabolic syndrome, cardiovascular disease, atherosclerotic heart disease, autoimmune disorder, insulin resistance, leptin resistance, arthritis, cell proliferation disorder (cancer or other proliferation disorder involving aberrant cell growth, e.g., vascular proliferative disease such as atherosclerosis, post-angioplasty restenosis, vein graft disease, and transplant vasculopathy)), or a combination of two or more of the foregoing. In some embodiments, the composition is a topical formulation, and the disorder is damaged skin (epidermis, dermis, or collagen), sores, cuts, rashes, bruises, dryness, burns, sunburn, radiation burn, infection, or a combination of two or more of the foregoing.

Another aspect of the invention concerns a method for regulating or suppressing appetite in a subject by administering an effective amount of a composition of the invention to the subject.

The subject in the methods of the invention may be a human or non-human animal. In some embodiments, the subject is a mammalian subject (human or non-human mammal).

Another aspect of the invention pertains to a method for inhibiting HMG-CoA reductase, inhibiting transformation of pre-adipocytes to adipocytes and inhibiting triglyceride storage, promoting insulin sensitivity in adipocytes, stimulating AMPK, promoting heat shock protein production (for example, heat shock protein 70 (HSP70)), inhibiting production of phosphorylated target of rapamycin (TOR), and increasing $NAD^+$ and NAD/NADH ratio, comprising contacting a target cell with an effective amount of a composition of the invention in vitro or in vivo. Cells to be contacted in vitro or in vivo may be those of a human or non-human animal subject. In some embodiments, the cells to be contacted are those of a mammalian subject (human or non-human mammal).

Another aspect of the invention concerns a method for producing a supercritical carbon dioxide extract of *Commiphora mukul* resin (guggul), comprising subjecting guggul to supercritical carbon dioxide extraction, resulting in a supercritical extract. The carbon dioxide may or may not be modified by ethanol addition. Preferably, the supercritical carbon dioxide extraction is carried out with a blend of carbon dioxide and ethanol as co-solvent under supercritical conditions. In some embodiments, the supercritical solvent comprises 1%-20% ethanol. In some embodiments, the supercritical solvent comprises 5%-15% ethanol.

Optionally, the production method further comprises cryo-milling the guggul prior to supercritical carbon dioxide extraction. Preferably, the cryo-milling is carried out using liquid carbon dioxide as a cryogen. However, other cryogens, such as liquid nitrogen or liquid argon, may be used. Preferably, the cryogen (e.g., liquid carbon dioxide) is injected directly into the milling chamber.

Preferably, the production method further comprises mixing the cryo-milled guggul with an inert carrier. The inert carrier may be an inert mineral carrier, such as flux-calcinated diatomite. Calcination is advantageous in that it avoids introduction of any organic components into the abstract. Preferably, the ratio of carrier to gum powder is selected or adjusted such that the mixture maintains powder form under ambient conditions, suitable for subsequent supercritical extraction. In some embodiments, the mixture comprises 35%-70% carrier. In some embodiments, the mixture comprises 40%-60% carrier.

In some embodiments, the extraction pressure is adjusted to 150-500 bar, and the extraction temperature is in the range of 40 degrees C. to 80 degrees C. In some embodiments, the extraction pressure is adjusted to 200-400 bar, and the extraction temperature is in the range of 45 degrees C. to 60 degrees C. Preferably, the supercritical extract is obtained by pressure release to 50-80 bar at a temperature in the range of 25 degrees C. to 70 degrees C.

Preferably, the supercritical $CO_2$ extract is obtained by a two-stage separation at which non-volatiles (e.g., sterols, sterones, polypodane-type triterpenes, and guggulignans) are obtained in the first stage, and the lower molecular weight components (e.g., mono- and sesquiterpenes and cembrenoid type diterpenes) are obtained together with the main proportion of ethanol in the second stage.

Following supercritical $CO_2$ extraction, ethanol may be removed from the supercritical extract using methods known in the art, such as vacuum evaporation.

Preferably, the supercritical $CO_2$ extract is combined with one or more medium chain triglycerides to form a liquid extract. In some embodiments, the liquid extract contains 1%-5% guggulsterone. In some embodiments, the liquid extract contains 1.5%-3% guggulsterone. In some embodiments, the composition comprises at least 0.1% guggulsterone (total E and/or Z guggulsterones). In some embodiments, the composition comprises about 0.1% to about 2% guggulsterone (total E and/or Z guggulsterones, e.g., about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% guggulsterone, or an increment in between).

The liquid guggul extract can be dried to a powder by blending on a solid carrier, such as a maltodextrin or starch type of plant extract, soluble or insoluble fibers, or milled plant parts such as rice hull powder, or with mineral powder. Alternatively, microencapsulation, nanoencapsulation, microemulsion, nanoemulsion or formulations in the form of liposomes are possible.

DETAILED DISCLOSURE OF THE INVENTION

Figure 1:
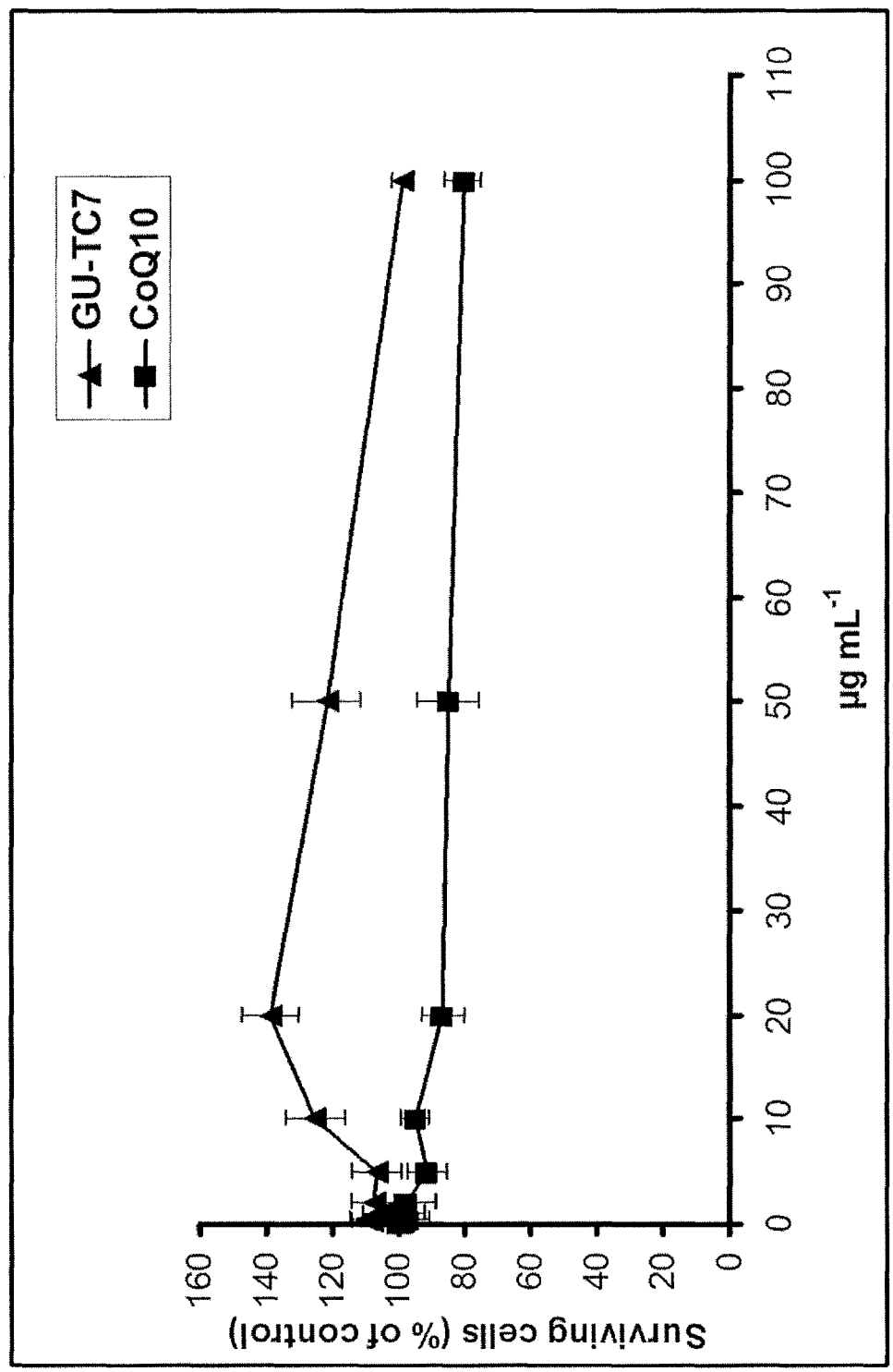
FIG. 1 is a graph showing cytotoxicity of GU-TC7 and CoQ10 in CCL-110 human skin fibroblast cell line. Cells were treated with GU-TC7 and CoQ10 for 24 hours and MTT assay was performed.

The $CO_2$ *Commiphora mukul* extracts of the invention and compositions containing them have many potential benefits. The inventors have identified compositions capable of supporting important biological mechanisms such as glucose metabolism (Claudel, T. et al. "The farnesoid X receptor: a molecular link between bile acid and lipid and glucose metabolism" *Arterioscler Thromb Vasc Biol.*, 2005; 25(10): 2020-2030; Lage, R. et al. "AMPK: a metabolic gauge regulating whole-body energy homeostasis" *Trends in Molec Med.*, 2008; 14:539-549; Long, Y. C. et al. "AMP-activated protein kinase signaling in metabolic regulation" *J Clin Invest.*, 2006, 116:1776-1783; Steinberg, G. R. et al. "AMPK in health and disease" *Physiol Rev.*, 2009, 89:1025-1078; Hardie, D. G. et al. "AMP-activated protein kinase-development of the energy sensor concept" *J. Physiol.*, 2006, 574:7-15; Stayrook, K. R. et al. "Regulation of Carbohydrate Metabolism by the Farnesoid X Receptor" *Endocrinology*, 2005, 146(3):984-991; Lim, C. T. et al. "AMPK as a mediator of hormonal signaling" *Endocrinology*, 2010, 44: 87-97; Osler, M. E. et al. "Minireview: Adenosine'5'-Monophosphate-Activated Protein Kinase Regulation of Fatty Acid Oxidation in Skeletal Muscle" *Endocrinology*, 2008, 149: 935-941; Sharma, B. et al. "Effects of guggulsterone isolated from *Commiphora mukul* in high fat diet induced diabetic rats" *Food Chem. Toxicol.*, 2009, 47(10):2631-2639); cholesterol metabolism with cholesterol levels already within the normal range; blood lipid metabolism (Claudel, T. et al. *Arterioscler Thromb Vasc Biol.*, 2005; Lage, R. et al. *Trends in Molec Med.*, 2008; Long, Y. C. et al. *J Clin Invest.*, 2006; Steinberg, G. R. et al. *Physiol Rev.*, 2009; Hardie, D. G. et al. *J. Physiol.*, 2006; Stayrook, K. R. et al. *Endocrinology*, 2005; Lim, C. T. et al. *Endocrinology*, 2010; Osler, M. E. et al. *Endocrinology*, 2008; Yang, J. H. et al. "Guggulsterone inhibits adipocyte differentiation and induces apoptosis in 3T3-L1 cells" *Obesity*, 2008, 16:16-22; Rizzo, G. et al. "The farnesoid X receptor promotes adipocyte differentiation and regulates adipose cell function in vivo" *Mol Pharmacol.*, 2006, 70:1164-1173; Nityanand, S. et al. "Clinical trials with guggulipid. A new hypolipidaemic agent" *J Assoc Physicians India*, 1989, 37:323-328; Gopal, K. et al. "Clinical trial of ethyl acetate extract of gum gugulu (gugulipid) in primary hyperlipidemia" *J Assoc Physicians India*, 1986, 34:249-251; Agarwal, R. et al. "Clinical trials of guggulipid—a new hypolipidemic agent of plant origin in primary hyperlipidemia" *Indian J Med Res.*, 1986, 84:626-634; Urizar, N. L. et al. "A natural product that lowers cholesterol as an agonist ligand for FXR" *Science*, 2002, 296:1703-1707); mitochondrial biogenesis (supporting the creation of new energy-producing mitochondria) (Lage, R. et al. *Trends in Molec Med.*, 2008; Long, Y. C. et al. *J Clin Invest.*, 2006; Steinberg, G. R. et al. *Physiol Rev.*, 2009; Hardie, D. G. et al. *J. Physiol.*, 2006; Lim, C. T. et al. *Endocrinology*, 2010; Canto, C. et al. "AMPK regulates energy expenditure by modulating $NAD^+$ metabolism and SIRT1 activity" *Nature*, 2009, 458:1056-1062); and primary energy production (Lage, R. et al. *Trends in Molec Med.*, 2008; Long, Y. C. et al. *J Clin Invest.*, 2006; Steinberg, G. R. et al. *Physiol Rev.*, 2009; Hardie, D. G. et al. *J. Physiol.*, 2006; Lim, C. T. et al. *Endocrinology*, 2010; Osler, M. E. et al. *Endocrinology*, 2008; Canto, C. et al. *Nature*, 2009).

These beneficial mechanisms can facilitate health by promoting cellular glucose uptake (Claudel, T. et al. *Arterioscler Thromb Vasc Biol.*, 2005; Lage, R. et al. *Trends in Molec Med.*, 2008; Long, Y. C. et al. *J Clin Invest.*, 2006; Steinberg, G. R. et al. *Physiol Rev.*, 2009; Hardie, D. G. et al. *J. Physiol.*, 2006; Stayrook, K. R. et al. *Endocrinology*, 2005; Gruzman, A. et al. "Adenosine monophosphate-activated protein kinase (AMPK) as a new target for antidiabetic drugs: A review on metabolic, pharmacologic and chemical considerations" *Rev Diabet Stud.*, 2009, 6:13-36); supporting cholesterol levels already within the normal range (e.g., through regulation of HMG-CoA reductase) (Izzat, N. N. et al. "New Molecular Targets for Cholesterol Lowering Therapy" *Perspectives in Pharmacology*, 2000, 293(2):315-320; Urizar, N. L. et al. *Science*, 2002); regulating transformation of pre-adipocytes to adipocytes (i.e., fat cells) and regulating triglyceride storage (Yang, J. H. et al. *Obesity*, 2008; Rizzo, G. et al. *Mol Pharmacol.*, 2006; Hardie, D. G. "The AMP-activated protein kinase pathway-new players upstream and downstream" *J Cell Sci.*, 2004, 117:5479-

5487; Urizar, N. L. et al. *Science,* 2002; Yang, J. H. et al. "Enhanced pro-apoptotic and anti-adipogenic effects of genistein plus guggulsterone in 3T3-L1 adipocytes" *BioFactors,* 2008, 30:159-169); and stimulating AMPK, the nutrient/energy sensor researched for its role in supporting energy levels in cells throughout the body (and a pharmacologic target for helping in the transport of glucose), and thus providing all the beneficial downstream effects that arise from AMPK activation (Lage, R. et al. *Trends in Molec Med.,* 2008; Long, Y. C. et al. *J Clin Invest.,* 2006; Steinberg, G. R. et al. *Physiol Rev.,* 2009; Hardie, D. G. et al. *J Physiol.,* 2006; Lim, C. T. et al. *Endocrinology,* 2010; Osler, M. E. et al. *Endocrinology,* 2008; Hardie, D. G. *J Cell Sci.,* 2004).

Coenzyme Q10 (CoQ10) is a major ingredient in skin care products because of its anti-wrinkle effects, although it has some side effects especially at higher amounts. In this study, we compare the anti-wrinkle related properties of CoQ10 and a proprietary *Commiphora mukul* gum resin (guggul) and triheptanoin preparation (GU-TC7). GU-TC7 is prepared with a supercritical $CO_2$-co-solvent extraction with ethanol, standardized to 2% guggulsterones and tri-heptanoin, a triglyceride composed of three 7-carbon fatty acids. Treatment of CCL-110 skin fibroblasts with GU-TC7 demonstrates a mild proliferative effect compared to CoQ10 and increased type I collagen synthesis. Additionally, GU-TC7 inhibited matrix metallo-proteinase-1 (MMP-1) expression in a dose-dependent manner at 20-100 μg $mL^{-1}$ and inhibited human elastase expression by more than 50% as compared to no elastase inhibition with CoQ10 treatment. These results suggest that GU-TC7 possesses properties that are applicable to the treatment of wrinkles and may be considered for its further evaluation in skin care products.

The skin consists of two distinct layers, the dermis and epidermis. The dermis is the thicker, deeper layer of the skin underlying the epidermis and is mainly composed of such connective tissues such as collagen and elastic fibres. Collagen fiber is the main component of the extracellular matrix and has a direct effect on skin tension. The elastic fibres together with collagen fibres form a network within the dermis. Elastin is an insoluble elastic fibrous protein in connective tissues that imparts elasticity and flexibility to connective tissue and is important in maintaining the youthful elasticity of the skin. Consequently, damage to elastin impairs elasticity of the skin; this usually occurs as a result of the natural aging process and is more often intensified by photo aging caused by excessive sun exposure (Schwartz, E. et al. "Collagen alterations in chronically sun-damaged human skin" *J. Photochem. Photobiol.,* 1993, 58:841-844; Lavker, R. M. "Structural alterations in exposed and unexposed aged skin" *J. Invest. Dermatol.* 1979, 73:559-566). Elastase is the major enzyme capable of degrading elastin and exerts pro-oxidative (Wiedow, O. et al. "An elastase-specific inhibitor of human skin" *J. Biol. Chem.,* 1990, 265:14791-14795) and pro-inflammatory (Kim, Y. H. et al. "Anti-wrinkle activity of *Platycarya strobilacea* extract and its application as a cosmeceutical ingredient" *J. Cosmet. Sci.,* 2010, 61:211-224) damage on connective tissue. Activation of elastase can break down connective tissue, promote a chronic inflammatory cycle and produce wrinkles in the skin. Repeated exposure to ultra-violet (UV) rays damage skin connective tissue and is thought to be associated with wrinkle formation. Research demonstrates that neutrophil elastase activity is elevated in the chronic UVB-irradiated skin of hairless mice, and neutrophil elastase was confirmed to be involved in MMP activation (Takeuchi, H. et al. "Neutrophil elastase contributes to extracellular matrix damage induced by chronic low-dose UV irradiation in a hairless mouse photoaging model" *J. Dermatol. Sci.,* 2010, 60:151-158). Therefore, reducing elastase activity can improve and prolong the elasticity and youthful appearance for the skin.

Topical treatment of the skin with biological agents such as retinoids can repair damage in aged/sun-damaged skin (Klingman, A. M. et al. "Topical tretinoin for photoaged skin" *J. Am. Acad. Dermatol.,* 1986, 15:836-859; Weiss, J. S. et al. "Topical tretinoin improves photoaged skin: a double blind, vehicle-controlled study" *JAMA,* 1988, 259: 527-532). The mechanisms of retinoids' action include inhibition of matrix metalloproteinase (MMP) generation (Fisher, G. J. et al. "The molecular basis of sun-induced premature skin ageing and retinoid antagonism" *Nature* (London), 1996, 379:335-338; Fisher, G. J. et al. "Pathophysiology of premature skin aging induced by ultraviolet light" *N. Engl. J. Med.,* 1997, 337:1419-1428) and stimulation of connective tissue matrix synthesis (Griffiths, C. E. M. et al. "Restoration of collagen formation in photodamaged human skin by tretinoin (retinoid acid)" *N. Eng. J. Med.,* 1993, 329:530-534; Talwar, H. S. et al. "Reduced type I and III procollagens in photodamaged adult human skin" *J. Invest. Dermatol.,* 1995, 105:285-290). In addition to retinoids, several medicinal herbs have been shown to possess anti-aging properties (Kim, S. W. et al. "Induction of extracellular matrix synthesis in normal human fibroblasts by anthraquinone isolated from *Morinda citrifolia* (Noni) fruit" *J. Med. Food,* 2005, 8:552-555; Aslam, M. N. et al. "Pomegranate as a cosmeceutical source: pomegranate fractions promote proliferation and procollagen synthesis and inhibit matrix metalloproteinase-1 production in human skin cells" *J. Ethnopharmacol.,* 2006, 103:311-318; Jung, E. et al. "Effect of *Camellia japonica* oil on human type I procollagen production and skin barrier function" *J. Ethnopharmacol.,* 2007, 112:127-131; Kim, Y. H. et al. "Anti-wrinkle activity of ziyuglucoside I isolated from a *Sanguisorba officinalis* root extract and its application as a cosmeceutical ingredient" *Biosci. Biotechnol. Biochem.,* 2008, 72:303-311; Kang, T. H. et al. "Effect of red ginseng extract on UVB irradiated-induced aging in hairless mice" *J. Ethnopharmacol.,* 2009, 123:446-452; Artaria, C. et al. "Lifting properties of the alkamide fraction from the fruit husks of *Zandthroxylum bungeanum*" *Int. J. Cosmet. Sci.,* 2011, 10:1468-2494), some of which are regularly included in cosmetic skin care products marketed throughout the world.

Aging of skin is mainly associated with the reduction in the level of type I collagen, which is the principal component of the dermis. Type I collagen is the main structural component of the extra-cellular matrix, which is known to perform a pivotal function in the maintenance of the structure of the dermis. Matrix metalloproteinases are enzymes related to collagenase that play a critical role in the degradation of basal membranes and the extra-cellular matrix. MMP-1, collagen type I and elastase are common biomarkers associated with anti-wrinkle effects and skin aging. Consequently, these biomarkers represent potential targets for the evaluation of compounds included in cosmeceutical products for the treatment of wrinkles, in particular, the inhibitory effect on MMP-1 and elastase activity and induction of type I collagen synthesis. In the ancient Ayurveda literature, guggul, the gum resin from the bark of *Commiphora mukul* is reported to possess anti-wrinkle effects. In the Examples, the inventors describe the effect of GU-TC7 on wrinkle-associated biomarkers in CCL-110 skin fibroblasts; GU-TC7 is a proprietary guggul formulation prepared by a super-critical $CO_2$-co-solvent extraction with ethanol, standardized to 2.0% guggulsterones and triheptanoin, a triglyceride composed of three 7-carbon fatty acids that has also been linked to several mechanisms that support lipid metabolism, glucose metabolism and cellular energy (Urizar, N. L. et al. "A natural product that lowers cholesterol as an antagonist ligand for FXR" *Science*, 2002, 296:1703-1706; Shishodia, S. et al. "The guggul for chronic diseases" *Anticancer Res.*, 2008:3647-3664; Wu, J. et al. "The hypolipidemic natural product guggulsterone acts as an antagonist of the bile acid receptor" *Mol. Endocrinol.*, 2009, 16:1590-1597). GU-TC7, a clear pale-yellow liquid, is also compared to coenzyme Q10 (CoQ10), a common ingredient in anti-wrinkle preparations.

Using in vitro assays, the inventors have demonstrated that the supercritical $CO_2$ guggul extracts of the invention and compositions of the invention containing the extracts have anti-adipogenic efficacy by inhibition of pre-adipocyte differentiation and stimulation of lipolytic enzymes resulting in reduced formation of adipose tissue. These mechanisms suggest that guggul extract contributes to the formation of a firm, even and smooth skin surface and alleviates wrinkle formation. The supercritical $CO_2$ guggul extracts of the invention and compositions of the invention containing the extracts possess properties making them useful for anti-inflammatory and anti-aging applications.

Another significant property observed from the supercritical $CO_2$ guggul extracts of the invention, and compositions containing the extracts, is their ability to stimulate AMPK-activated protein kinase (AMPK), which up-regulates cellular energy production by phosphorylation of key enzymes in metabolic pathways. AMPK activation is associated directly and indirectly with multiple molecular pathways that involve regulation of lipid metabolism, carbohydrate metabolism, protein metabolism, cell growth, apoptosis, and aging and that show clear anti-proliferative and anti-cancer effects, (see, for example, Fay J. R. et al., "Energy Homeostasis and Cancer Prevention: The AMP-Activated Protein Kinase", *Cancer Prev. Res.*, 2009, 2(4):301-309; Luo Z. et al., "AMPK as a metabolic tumor suppressor: control of metabolism and cell growth," *Future Oncol.*, 2010, 6(3): 457-470; and Motoshima H. et al., "AMPK and cell proliferation—AMPK as a therapeutic target for atherosclerosis and cancer," *J. Physiol.*, 2006, 574.1:63-71). Without being limited by theory of mechanism of action, the ability to stimulate AMPK activity makes the compositions of the invention useful for treatment and delay of cancers such as cancer of the lung, breast, colon, ovary, gastrointestinal tract, head and neck, endometrium, and skin, as well as other cell proliferation disorders involving aberrant cell growth (e.g., vascular proliferative diseases such as atherosclerosis, post-angioplasty restenosis, vein graft disease, and transplant vasculopathy). Consistent with this, compositions of the invention have shown to have anti-cancer effects against the CEM (human leukemic lymphoblast), CEM.VLB (human leukemic lymphoblasts resistant to vinca alkaloids (vinblastine)), and HepG2 (human hepatocellular carcinoma) cell lines. Thus, methods of the invention include methods for treating or delaying the onset of a cell proliferation disorder (e.g., cancer) in a subject, comprising administering an effective amount of a composition of the invention to the subject.

Without being bound by theory, in some embodiments, the proliferation disorder to be treated is a disorder (e.g., cancer) characterized by aberrant AMPK regulation or otherwise treatable by increased activation of AMPK.

Furthermore, the methods of the invention include methods for killing or inhibiting the growth of abnormally proliferating cells in vitro in vivo, comprising contacting the cells with an effective amount of a composition of the invention in vitro or in vivo. In some embodiments, the abnormal proliferation is characterized by aberrant AMPK regulation or otherwise inhibited by increasing AMPK activation in the cells.

In addition to use as a monotherapy to treat or delay the onset of a proliferation disorder, compositions of the invention may be used as an adjunctive agent in combination with other agents useful for treating the proliferation disorder. For example, compositions of the invention may be administered to a subject before, during, or after administration of another anti-cancer treatment (e.g. chemotherapy, radiation therapy, immunotherapy, and/or surgery) to treat or delay the onset of cancer. Methods for killing or inhibiting the growth of abnormally proliferating cells in vitro or vivo may utilize additional agents useful for killing or inhibiting abnormally proliferating cells as well. Additional agents (e.g., anti-cancer agents such as chemotherapeutic agents) may be administered to the subject or contacted with the cells within the composition of the inventions or in separate compositions.

Additionally, without being limited by theory of mechanism of action, the compositions of the invention may be administered to a subject to regulate or suppress appetite, based on the inventors' observations of suppression of AMPK in a hypothalamus cell line. Thus, the methods of the invention also include a method for regulating or suppressing appetite in a subject by administering an effective amount of a composition of the invention to the subject.

The optimal formulations for the compositions of the invention can be readily determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

The compositions of the invention may be administered by any conventional route including oral and parenteral. Examples of parenteral routes are subcutaneous, intradermal, transcutaneous, intravenous, intramuscular, intraorbital, intracapsular, intrathecal, intraspinal, intracisternal, intraperitoneal, etc. The compositions of the invention can be formulated for the most effective route of administration, including for example, oral, topical, transdermal, sublingual, buccal, parenteral, rectal, intranasal, intrabronchial or intrapulmonary administration. By way of example, the composition may be formulated as a microencapsulation, nanoencapsulation, microemulsion, nanoemulsion, liposomal preparation, capsule, tablet, sublingual form, quick-dissolve form, biofilm, oil solubilization, spray, or cosmeceutical preparation (e.g., cream, oil, or shampoo).

In some embodiments, the composition is administered systemically (e.g., orally). In some embodiments, the composition is administered locally at the site of action.

In some embodiments, the composition is administered with one or more other agents useful in treating or delaying the onset of a disorder. The compositions of the inventions and any additional agent (if administered) can be administered within the same formulation or different formulations. If administered in different formulations, the composition and the additional agent(s) can be administered by the same route or by different routes, before, during, and/or after administration of the composition of the invention.

Depending on the intended mode of administration, the compositions used in the methods described herein may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. Each dose may include an effective amount of a composition used in the methods described herein in combination with a pharmaceutically acceptable carrier and, in addition, may include other medicinal agents, pharmaceutical agents, carriers, adjuvants, diluents, etc. An effective dose in vitro or in vivo will be appropriate for the desired effect (e.g., treating or delaying the onset of a disorder (e.g., a cell proliferation disorder such as cancer), regulating or suppressing appetite, inhibiting HMG-CoA reductase, inhibiting transformation of pre-adipocytes to adipocytes and inhibiting triglyceride storage, promoting insulin sensitivity in adipocytes, stimulating AMPK, promoting heat shock protein production (for example, heat shock protein 70 (HSP70)), inhibiting production of phosphorylated target of rapamycin (TOR), and increasing NAD and NAD/NADH ratio). For example, in some embodiments, 500 mg of the composition is orally administered to a subject once or twice per day. The percentage of active ingredients in cosmeceutical formulations tends to be in the range of 0.1%-2.0%.

In some embodiments, the composition comprises at least 0.1% guggulsterone (total E and/or Z guggulsterones). In some embodiments, the composition of the invention comprises at least 1% guggulsterone. In some embodiments, the composition comprises 0.1%-5% guggulsterone (total E and/or Z guggulsterones). In some embodiments, the composition comprises 1%-5% guggulsterone (total E and/or Z guggulsterones). In some embodiments, the composition comprises 1.5%-3% guggulsterone (total E and/or Z guggulsterones).

In some embodiments, the composition comprises about 0.1% to about 2% guggulsterone (total E and/or Z guggulsterones, e.g., about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% guggulsterone, or an increment in between).

In some embodiments, the composition comprises 1.9%-2.1% guggulsterones (e.g., by HPLC); 6%-9% phytosterol (e.g., sitosterol); essential oil; cembrene; mukulol (allycembrol); and less than 3% ethanol.

The percentage of active ingredients in the compositions of the invention can be tailored to the desired application. For example, excipients and other agents may be added to reduce the concentration of a desired active ingredient. In some embodiments, an oil is included in the composition. In some embodiments, triheptanoin (TC7) or another oil, is included for topical applications. In some embodiments, MCT or another oil, is included for dietary application. In some embodiments, for cosmeceutical formulations, a composition of the invention comprising about 0.1% to about 1% guggulsterones is administered to the subject topically. In some embodiments, for cosmeceutical formations, a composition of the invention comprising about 1% guggulsterones (e.g., GU-TC7) is administered to the subject topically.

Liquid pharmaceutically administrable compositions can be prepared, for example, by combining a composition described herein with an excipient, such as, for example, water, saline aqueous dextrose, glycerol, ethanol, and the like, to thereby form a solution or suspension. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. If desired, the composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; see, for example, Remington's Pharmaceutical Sciences, 18th Ed. (1990), Mack Publishing Co., Easton, Pa., the entire disclosure of which is hereby incorporated by reference).

Formulations comprising compositions described herein may be presented in unit-dose or multi-dose containers, for example sealed ampoules and vials, and may be stored in a freeze dried (lyophilized) condition requiring only the condition of the sterile liquid carrier, for example, water, prior to use. Extemporaneous injection solutions and suspensions may also be prepared from sterile powder, granules, tablets, etc. It should be understood that in addition to the ingredients particularly mentioned above, the formulations of the subject invention can include other agents conventional in the art having regard to the type of formulation in question.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal; B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification Principles and Practice (2nd ed., Springer-Verlag); and PCR: A Practical Approach (McPherson et al. Eds. (1991) IRL Press)), each of which are incorporated herein by reference in their entirety.

Experimental controls are considered fundamental in experiments designed in accordance with the scientific method. It is routine in the art to use experimental controls in scientific experiments to prevent factors other than those being studied from affecting the outcome.

Exemplified Embodiments

Embodiment 1

A composition comprising a supercritical carbon dioxide extract of *Commiphora mukul* resin (guggul), wherein the carbon dioxide is optionally modified by ethanol addition.

Embodiment 2

The composition of embodiment 1, further comprising an oil (natural or synthetic).

Embodiment 3

The composition of embodiment 2, wherein the oil comprises one or more medium chain triglycerides.

Embodiment 4

The composition of embodiment 3, wherein the one or more triglycerides comprise C8 and C10 fatty acids.

Embodiment 5

The composition of embodiment 3, wherein the oil comprises triheptanoin.

Embodiment 6

The composition of embodiment 2, wherein the oil comprises at least one selected from among olive oil, chia seed oil, soy germ oil, pomegranate oil (seed, pericarp, fruit), fish oil, and seafood oil (e.g., krill oil).

Embodiment 7

The composition of any preceding embodiment, wherein the composition contains 0.1%-5% guggulsterone (total E and Z guggulsterones).

Embodiment 8

The composition of embodiment 7, wherein the composition contains 1.5%-3% guggulsterone (total E and Z guggulsterones).

Embodiment 9

The composition of any preceding embodiment, wherein the composition comprises 1.9%-2.1% guggulsterones (by HPLC); 6%-9% phytosterol (e.g., sitosterol); essential oil; cembrene; mukulol (allycembrol); and less than 3% ethanol.

Embodiment 10

The composition of any preceding embodiment, further comprising an agent selected from among a botanical extract, mineral, vitamin, nutrient, other nutraceutical, dietary supplement, or active pharmaceutical ingredient.

Embodiment 11

The composition of any preceding embodiment, further comprising a botanical extract selected from among a sterol, sterone, steroid, polyphenol, flavonoid, terpenoid, alkaloid, or a polysaccharide.

Embodiment 12

The composition of any preceding embodiment, wherein the composition is an oral formulation.

Embodiment 13

The composition of any one of embodiments 1 to 11, wherein the composition is a topical formulation.

Embodiment 14

The composition of any preceding embodiment, wherein the composition is 100% natural.

Embodiment 15

The composition of any preceding embodiment, wherein the composition is a liquid.

Embodiment 16

The composition of any one of embodiments 1 to 14, wherein the composition is a powder.

Embodiment 17

The composition of any one of embodiments 1 to 14, wherein the composition is formulated as a microencapsulation, nanoencapsulation, microemulsion, nanoemulsion, liposomal preparation, capsule, tablet, sublingual form, quick-dissolve form, biofilm, oil solubilization, spray, or cosmeceutical preparation (e.g., cream, oil, or shampoo).

Embodiment 18

A method for treating or delaying the onset of a disorder in a subject, comprising administering an effective amount of the composition of any one of embodiments 1 to 17 to the subject.

Embodiment 19

The method of embodiment 18, wherein the disorder is a cell proliferation disorder.

Embodiment 20

The method of embodiment 19, wherein the cell proliferation disorder is cancer or atherosclerosis.

Embodiment 21

The method of embodiment 19 or 20, further comprising administering a different treatment for the cell proliferation disorder before, during, and/or after administration of the composition.

Embodiment 22

The method of embodiment 21, wherein the cell proliferation disorder is cancer, and the different treatment comprises administration of a chemotherapeutic agent, radiation therapy, immunotherapy, and/or surgery.

Embodiment 23

The method of embodiment 18, wherein the composition is an oral formulation, and wherein the disorder is selected from among hypercholesterolemia, hyperlipidemia, hyperglycemia, obesity, metabolic syndrome, cardiovascular disease, atherosclerotic heart disease, autoimmune disorder, insulin resistance, leptin resistance, arthritis, and cell proliferation disorder.

Embodiment 24

The method of embodiment 18, wherein the composition is a topical formulation, and wherein the disorder is selected from among damaged skin (epidermis, dermis, or collagen), sores, cuts, rashes, bruises, dryness, burns, sunburn, radiation burn, and infection.

Embodiment 25

The method of any preceding embodiment, wherein the subject is a human.

Embodiment 26

The method of any preceding embodiment, wherein the subject is a non-human animal.

Embodiment 27

A method for regulating or suppressing appetite in a subject, comprising administering an effective amount of a composition of any one of embodiments 1 to 17 to the subject.

Embodiment 28

A method for inhibiting HMG-CoA reductase, inhibiting transformation of pre-adipocytes to adipocytes and inhibiting triglyceride storage, promoting insulin sensitivity in adipocytes, stimulating AMPK, promoting heat shock protein production, inhibiting production of phosphorylated target of rapamycin (TOR), and increasing $NAD^+$ and NAD/NADH ratio, comprising contacting a target cell with an effective amount of a composition of any one of embodiments 1 to 17 in vitro or in vivo.

Embodiment 29

A method for producing a supercritical carbon dioxide (with or without ethanol addition) extract of *Commiphora mukul* resin (guggul), comprising subjecting guggul to supercritical carbon dioxide extraction, resulting in a supercritical extract.

Embodiment 30

The method of embodiment 29, wherein the supercritical carbon dioxide extraction is carried out with a blend of carbon dioxide and ethanol as co-solvent under supercritical conditions.

Embodiment 31

The method of embodiment 29, wherein the supercritical solvent comprises 1%-20% ethanol.

Embodiment 32

The method of embodiment 31, wherein the supercritical solvent comprises 5%-15% ethanol.

Embodiment 33

The method of any preceding embodiment, further comprising cryo-milling the guggul prior to supercritical carbon dioxide extraction.

Embodiment 34

The method of embodiment 33, wherein said cryo-milling is carried out using liquid carbon dioxide as a cryogen, and wherein the liquid carbon dioxide is injected directly into a milling chamber.

Embodiment 35

The method of embodiment 33 or 34, further comprising mixing the cryo-milled guggul with an inert carrier.

Embodiment 36

The method of embodiment 35, wherein the mixture of the cryo-milled guggul and carrier is a powder that is subjected to the supercritical carbon dioxide extraction.

Embodiment 37

The method of embodiment 35 or 36, wherein the carrier comprises flux-calcinated diatomite or other inert mineral carrier.

Embodiment 38

The method of any one of embodiments 35 to 37, wherein the mixture comprises 35%-70% carrier.

Embodiment 39

The method of embodiment 38, wherein the mixture comprises 40%-60% carrier.

Embodiment 40

The method of any preceding embodiment, wherein the extraction pressure is adjusted to 150-500 bar, and the extraction temperature is in the range of 40 degrees C. to 80 degrees C.

Embodiment 41

The method of any preceding embodiment, wherein the extraction pressure is adjusted to 200-400 bar, and the extraction temperature is in the range of 45 degrees C. to 60 degrees C.

Embodiment 42

The method of any preceding embodiment, wherein the supercritical extract is obtained by pressure release to 50-80 bar at a temperature in the range of 25 degrees C. to 70 degrees C.

Embodiment 43

The method of embodiment 30, wherein the supercritical extract is obtained by a two-stage separation at which non-volatiles (e.g., sterols, sterones, polypodane-type triterpenes, and guggulignans) are obtained in the first stage, and wherein lower molecular weight components (e.g., mono- and sesquiterpenes and cembrenoid type diterpenes) are obtained together with the main proportion of ethanol in the second stage.

Embodiment 44

The method of any one of embodiments 30-42, further comprising removing the ethanol from the supercritical extract by vacuum evaporation.

Embodiment 45

The method of any preceding embodiment, further comprising combining the supercritical extract with an oil (natural or synthetic) to form a liquid extract.

Embodiment 46

The method of embodiment 45, wherein the oil comprises one or more medium chain triglycerides.

Embodiment 47

The method of embodiment 46, wherein the one or more medium chain triglycerides comprise caprylic/capric triglycerides, triheptanoin, or both.

Embodiment 48

The method of embodiment 45, wherein the oil includes at least one selected from among olive oil, chia seed oil, soy germ oil, pomegranate oil (seed, pericarp, fruit), fish oil, and seafood oil (e.g., krill oil).

Embodiment 49

The method of any one of embodiments 45 to 48, wherein the liquid extract contains 0.1%-5% guggulsterone (total E and Z guggulsterones).

Embodiment 50

The method of embodiment 49, wherein the liquid extract contains 1.5%-3% guggulsterone (total E and Z guggulsterones).

Embodiment 51

The method of any one of embodiments 45 to 50, wherein the liquid extract contains 1.9%-2.1% guggulsterones (by HPLC); 6%-9% phytosterol (e.g., sitosterol); essential oil; cembrene; mukulol (allycembrol); and less than 3% ethanol.

Embodiment 52

The method of any preceding embodiment, further comprising adding an agent to the supercritical extract, wherein the agent is selected from among a botanical extract, mineral, vitamin, nutrient, other nutraceutical, dietary supplement, or active pharmaceutical ingredient.

Embodiment 53

The method of any preceding embodiment, further comprising adding a botanical extract to the supercritical extract, wherein the botanical extract is selected from among a sterol, sterone, steroid, polyphenol, flavonoid, terpenoid, alkaloid, or a polysaccharide.

Definitions

In order that the present disclosure may be more readily understood, certain terms are first defined. Additional definitions are set forth throughout the detailed description.

The terms "eliminating," "substantially reducing," "treating," and "treatment," as used herein, refer to therapeutic or preventative measures described herein. The methods of "eliminating or substantially reducing" employ administration of a composition of the invention to a subject having a disorder, such as cancer or a metabolic disorder. In some embodiments, the term "eliminating" refers to a complete remission of the disorder in a subject treated using the methods described herein. In some embodiments, a subject is in complete remission at the time the composition of the invention is administered.

The terms "cancer" and "malignancy" are used herein interchangeably to refer to or describe the physiological condition in mammals that is typically characterized by unregulated cell growth. The cancer may be a drug-resistant or drug-sensitive type. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, gastrointestinal cancer, endometrial carcinoma, kidney cancer, and thyroid cancer.

Other non-limiting examples of cancers are basal cell carcinoma, biliary tract cancer; bone cancer; brain and CNS cancer; choriocarcinoma; connective tissue cancer; colorectal cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer (melanoma); stomach cancer; testicular cancer; uterine cancer; cancer of the urinary system, as well as other carcinomas and sarcomas. Examples of cancer types that may potentially be treated, or their onset delayed, using the compositions and methods of the present invention are also listed in Table 1.

TABLE 1

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult |
| Acute Myeloid Leukemia, Adult | (Primary) |
| Acute Myeloid Leukemia, Childhood | Hepatocellular (Liver) Cancer, Childhood |
| Adrenocortical Carcinoma | (Primary) |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, |
| Astrocytoma, Childhood Cerebral | Childhood |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |

TABLE 1-continued

Examples of Cancer Types

Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma TABLE 1-continued Examples of Cancer Types

| | |
|---|---|
| Primary, Metastatic | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In some embodiments of the invention, the cell proliferation disorder is a cancer selected from leukemia, hepatic carcinoma, pancreatic cancer, colon cancer, rhabdomyosarcoma, brain cancer, neuroblastoma, and breast cancer. In some embodiments of the invention, the cell proliferation disorder is selected from among cancer of the lung, breast, prostate, colon, ovary, gastrointestinal system (e.g., esophagus), head and neck, endometrium, and skin (melanoma).

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The compositions and methods of the invention can be utilized for early, middle, or late stage disease, and acute or chronic disease.

As used herein, the terms "treat" or "treatment" refer to both therapeutic treatment and prophylactic or preventative measures, wherein the object is to prevent or slow down (lessen) an undesired physiological change or disorder, such as the development or spread of cancer or other disorder. For purposes of this invention, beneficial or desired clinical results (i.e., a positive clinical outcome) include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a composition in accordance with the invention can result in therapeutic treatment or prophylaxis of cancer. "Treatment" can also mean prolonging survival as compared to expected survival if not receiving treatment. Those in need of treatment include those already with the condition or disorder as well as those prone to have the condition or disorder or those in which the onset of the condition or disorder is to be delayed (e.g., prevented). Optionally, the subject may be identified (e.g., diagnosed by a medical professional) as one suffering from the disease or condition prior to treatment with the composition.

As used herein, the term "(therapeutically) effective amount" refers to an amount of a composition effective to treat a disorder in a mammalian subject (human or non-human mammal). In the case of cancer (which includes pre-cancer), the therapeutically effective amount of a composition may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer (i.e., a positive clinical outcome). To the extent administration prevents growth of and/or kills existing cancer cells, it may be cytostatic and/or cytotoxic.

As used herein, the term "growth inhibitory amount" refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

As used herein, the terms "patient", "subject", and "individual" are used interchangeably and are intended to include human and non-human animal species. For example, the subject may be a human or an animal model.

As used in this specification, the singular forms "a", "an", and "the" include plural reference unless the context clearly dictates otherwise. Thus, for example, a reference to "an antibody" means one or more such antibody.

The following abbreviations are used herein:
GS: guggul carbon dioxide ($CO_2$) extract
GSE=guggul $CO_2$ and ethanol extract of GS residue
GU=GS and GSE blend All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume, supra and infra, unless otherwise noted.

Example 1

Supercritical Extract Obtained Directly from Guggul Gum Resin

The composition of the invention represents the first supercritical extract that is directly obtained from guggul gum resin. The sticky and brittle starting material is conditioned in a special cryo-milling process characterised by injection of liquid carbon dioxide directly into the milling chamber to form dry ice and provide inert milling atmosphere. The resulting powder is immediately mixed with inert mineral carrier. The carrier can be, but is not limited to, flux-calcinated diatomite. Calcination avoids the introduction of organic components into the extract. The ratio of carrier to gum powder should be adjusted in a way such that the blend maintains powder form under ambient conditions, suitable for subsequent supercritical extraction. A preferred proportion of the mineral carrier in the blend is 35-70%, preferentially 40-60%. The powder material is extracted with a blend of $CO_2$ and ethanol as co-solvent under supercritical conditions. The supercritical solvent contains 1-20% of ethanol, preferentially 5-15% of ethanol. Extraction pressure is adjusted to 150-500 bar, preferentially 200-400 bar and extraction temperature is 40-80° C., preferentially 45-60° C. The extract is obtained by pressure release to 50-80 bar at a temperature of 25-70° C.

Preferably, the extract is obtained by a two-stage separation at which the non-volatiles, e.g., sterols, sterones, polypodane type triterpenes and guggullignans are obtained mainly in the first stage whereas lower molecular weight components, e.g., mono- and sesquiterpenes and cembrenoid type diterpenes are obtained together with the main proportion of ethanol in the second stage. This approach facilitates extract work up and standardization as well as removal of ethanol by vacuum evaporation in a special distillation unit designed for handling viscous products under gentle conditions. The remaining extract fractions are combined, analysed and standardised to 1-5% (Z+E)-guggulsterone content, preferentially 1.5-3% sterone content by the addition of medium chain triglycerides, caprylic/capric triglycerides or triheptanoin. This results in a unique type of liquid guggul extract with high sterone and sterol content similar to standard solvent extracts which have powder form and are not miscible with medium chain triglycerides.

The liquid form of this special extract blend offers new and improved delivery possibilities for use of guggul actives in supplements, pharmaceuticals, and cosmetics. Incorporation of the oils, such as medium chain triglycerides, not only allows for the addition of inert excipient for standardization, but also contributes to efficacy and bioavailability.

Example 2

Supercritical Guggul Extract has Protective and Restorative Effects on Skin Fibroblasts Cells The present investigation, was undertaken to evaluate the effects of GU-TC7 compared to CoQ10 on biomarkers of skin aging and damage, viz., type I collagen synthesis, and inhibition of elastase and MMP-1 in a human skin fibroblast cell line.

Materials and Methods

Cell Line.

The fibroblast cell line CCL-110 was purchased from American Type Culture Collection (Manassas, Va., U.S.A.). The cells were grown in Eagle's Minimum Essential Medium (EMEM) containing 10% fetal bovine serum and antibiotics (penicillin and streptomycin) in a humidified atmosphere containing 95% air and 5% $CO_2$ at 37° C.

GU-TC7 Preparation.

Supercritical guggul extract was obtained by $CO_2$-cosolvent extraction with small amount of ethanol as entrainer. The purified genuine extract represents about 20% of the starting material and contains small amounts of volatile components, cembrene-type deterpenes, polypodane-type triterpenes, pregnane-type sterones as well as phytosterols and lipophilic lignans. The extract is standardized to 2% guggulsterones (HPLC) by the addition of treheptanoin. Triheptanoin, a food-grade medium-chain triglyceride, has natural origin and was produced by re-esterification of heptanoic acid obtained from castor oil and glycerol obtained from vegetable oils. Chemical analysis of guggul extract showed that it contains 6.6% essential oil, 0.82% guggulsterone E, 2.9% guggulsterone Z, 2.1% cembrene A, 0.71% mukulol and (allylcembrol) and 14.2% sitosterols.

Cytotoxicity Assay

Cytotoxicity Assay.

CCL-110 skin fibroblasts were cultured and plated at a density of $0.5 \times 10^4$ cells per well in 96-well tissue culture multiwell plates in EMEM medium. On the next day when cells were attached, they were treated with increasing concentrations (0-100 µg mL$^{-1}$) of GU-TC7 and CoQ10 (CoQ10 purchased from Sigma Chemical Co., St. Louis, Mo., U.S.A.) at 37° C. for 24 hours in a $CO_2$ incubator maintained at 5% $CO_2$ and 95% air. Cell proliferation assay was performed using the Cell Proliferation I kit (Roche Biochemicals, Indianapolis, Ind., U.S.A.) according to the manufacturer's protocol. The percentage survival of cells at each concentration was calculated based on the untreated control and plotted against drug concentrations (Cochrane, C. B. et al. "Anticancer effects of *Annona glabra* plant extracts in human leukemic cell lines" *Anticancer Res.*, 2008, 28:965-971). Cytotoxicity assay was repeated three times with triplicate samples in each and mean values calculated.

MMP-1 Expression.

CCL-110 skin fibroblast cells ($10^5$ mL$^{-1}$) were plated in 0.5% FBS containing EMEM for 24 hours for starvation and then treated with increasing concentrations of GU-TC7 and CoQ10 (0-100 µg mL$^{-1}$) for another 24 hours with and without the positive control (10 ng mL$^{-1}$ of TNF-α). The medium was harvested and analyzed for MMP-1 (ng mL$^{-1}$) using the human MMP-1 ELISA kit from R&D Systems (Minneapolis, Minn., U.S.A.) according to the manufacturer's instructions. MMP-1 ELISA studies were repeated three times, with duplicate samples in each assay.

Collagen Type I Expression.

CCL-110 human fibroblast cells ($0.5 \times 10^6$) were treated with increasing concentrations of GU-TC7 and CoQ10 for 24 hours in 0.5% starving medium. On the next day, the medium was completely removed, washed with phosphate buffered saline once and lysed with 500 µL of 0.05 M acetic acid (pH 2.8-3.0) and 50 µL of pepsin solution by incubating at 4° C. for 48 hours. Later, 50 mL of 10×TBS (1 M Tris, 2 M NaCl, 50 mM $CaCl_2$) was added, and pH was adjusted to 8.0 with 1 N NaOH, and 50 µL of human pancreatic elastase was added followed by the incubation for another 48 hours at 4° C. The cells were scraped and transferred to eppendorf tubes and centrifuged for 10 min at 10 000 rpm. The supernatant was transferred to a new eppendorf tube, and protein concentration of the extract was determined. The type I collagen in the extract was analyzed using the human type 1 collagen ELISA kit from MD Bio-products (St. Paul, Mich., U.S.A.).

PMN-Elastase Expression.

CCL-110 skin fibroblast cells ($10^6$) were plated in EMEM containing 0.5% FBS and treated with increasing concentrations of GU-TC7 and CoQ10 for 24 hours in a $CO_2$ incubator. The monolayer was lysed with 500 µL of RIPA buffer (50 mM Tris PH 7.4, 150 mM NaCl, 0.1% SDS, 0.5% Sodium deoxycholate, 1% Triton X-100 with one tablet for 25 mL of buffer) and protein concentration of the cellular extract was determined. Cellular extract (100 µg protein) was analyzed for the expression of human elastase using the PMN-Elastase ELISA kit form Alpco Immunoassays (Salem, N.H., U.S.A.).

Statistical Analysis.

Mean and standard deviation values were calculated from three independent experiments with duplicate samples in each assay for MMP-1, type 1 collagen and elastase. Mean values were compared statistically using Student's t-test.

Results

Cytotoxicity of GU-TC7 and CoQ10

Within the test window up to 100 µg mL$^{-1}$, both GU-TC7 and CoQ10 showed no cytotoxic effects on CCL-110 skin fibroblasts in culture (FIG. 1). However, a slight but noticeable cell proliferation effect was evident with GU-TC7 treatment between 5 and 50 µg mL$^{-1}$ concentrations ($P<0.05$).

Inhibition of MMP-1

Figure 2:
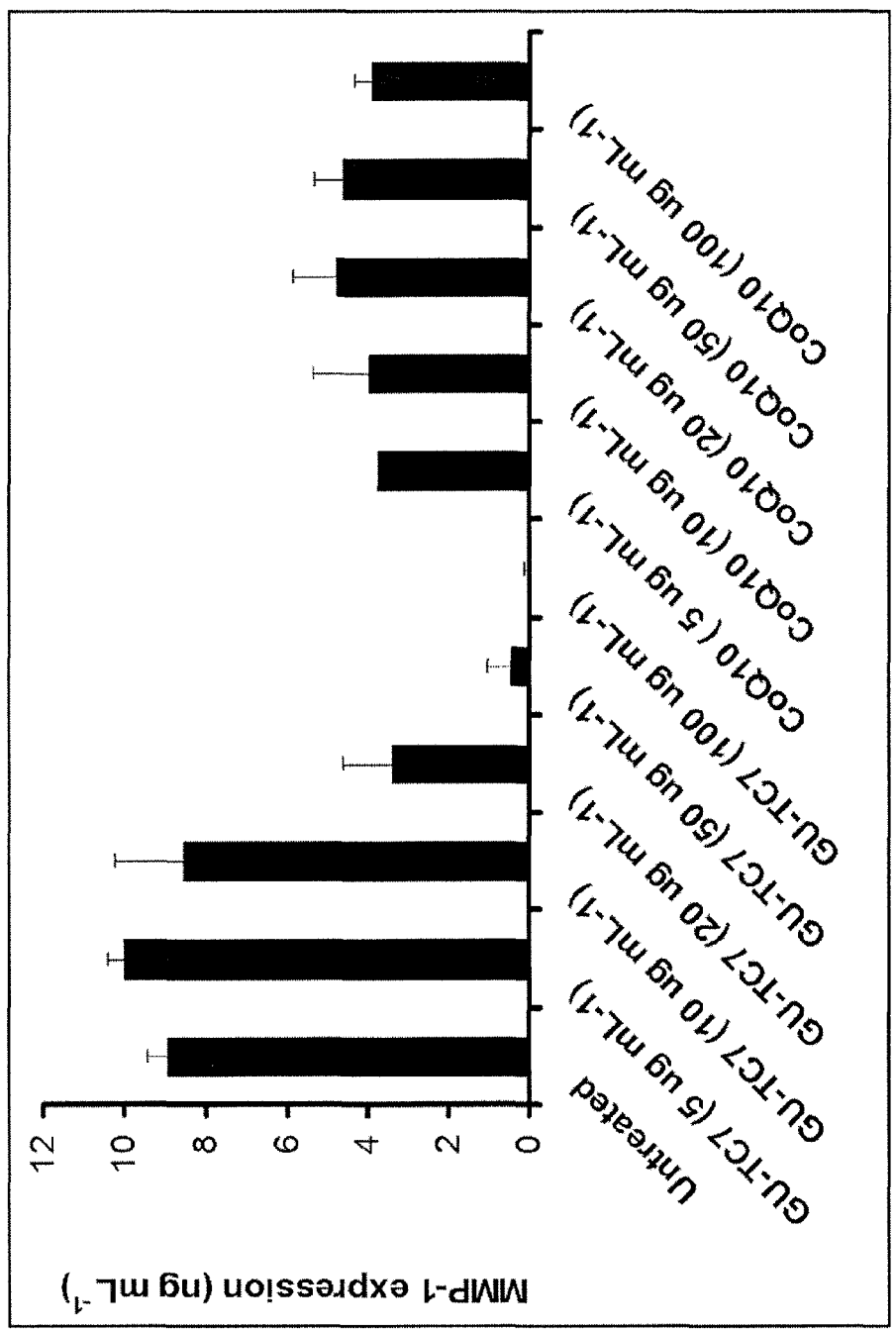
FIG. 2 is a graph showing inhibition of matrix metalloproteinase-1 expression by GU-TC7 (GU solubulized in triheptanoin) and CoQ10 in CCL-110 human skin fibroblast cell line.
Figure 3:
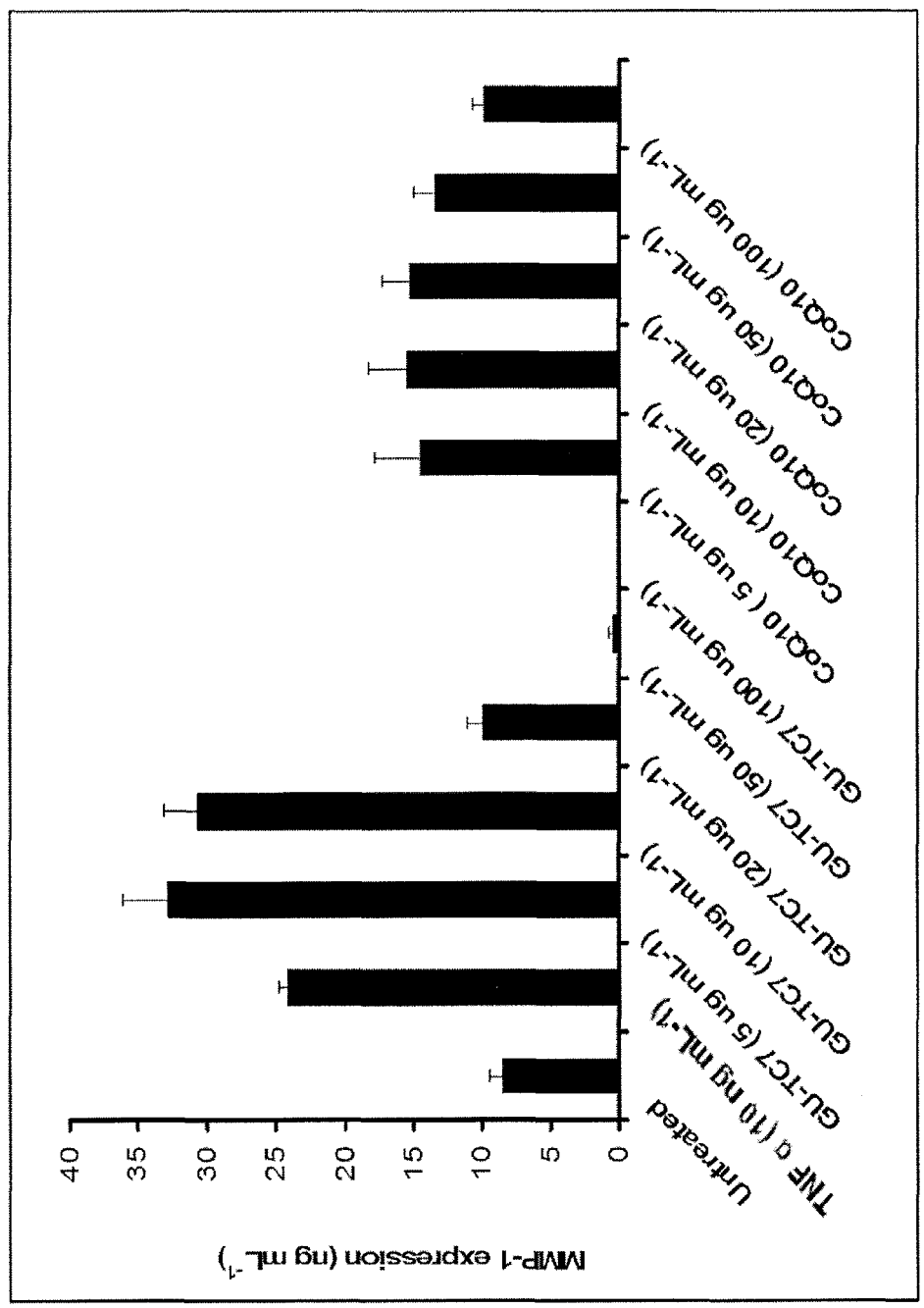
FIG. 3 is a graph showing Inhibition of TNF-α-induced matrix metalloproteinase-1 expression by GU-TC7 and CoQ10 in CCL-110 human fibroblast cell line.

The effect of GU-TC7 and CoQ10 on MMP-1 protein expression is shown in FIG. 2. GU-TC7 at 20 µg mL$^{-1}$ and above inhibited MMP-1 expression in a dose-dependent manner. CoQ10 although inhibits MMP-1 at 5 µg mL$^{-1}$, the inhibition rate remained almost constant with increasing concentrations. TNF-α(10 µg mL$^{-1}$) treatment increased MMP-1 expression three times compared to untreated CCL-110 cells (FIG. 3). GU-TC7 at 5 and 10 µmL$^{-1}$ failed to inhibit TNF-α-induced MMP-1 expression and started inhibiting MMP-1 secretion by skin fibroblasts at concentrations of 20 µg mL$^{-1}$ with almost complete inhibition by 50-100 µg mL$^{-1}$.

Enhancement of Collagen Type 1 Synthesis

Figure 4:
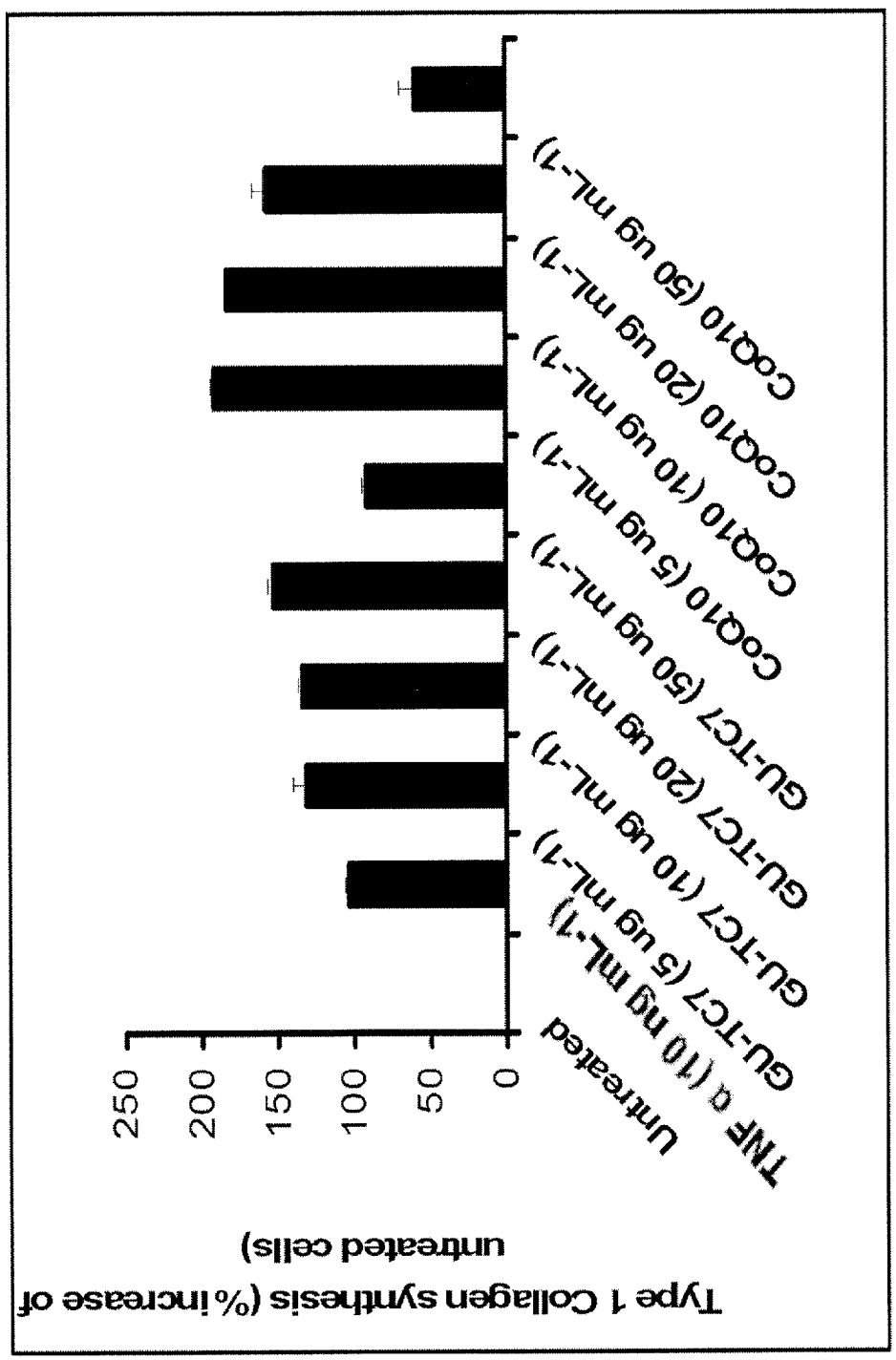
FIG. 4 is a graph showing effect of GU-TC7 and CoQ10 on Type I collagen synthesis in CCL-110 human fibroblast cell line.

GU-TC7 treatment increased type I collagen synthesis, although the effect may be lower than with CoQ10 (FIG. 4). However, an inhibitory trend was noticed with increasing doses of CoQ10. Even though GU-TC7 at 50 µg mL$^{-1}$ decreased the level of type 1 collagen, the level of decrease was smaller than at 50 µg mL$^{-1}$ of CoQ10.

Inhibition of Human Elastase

Figure 5:
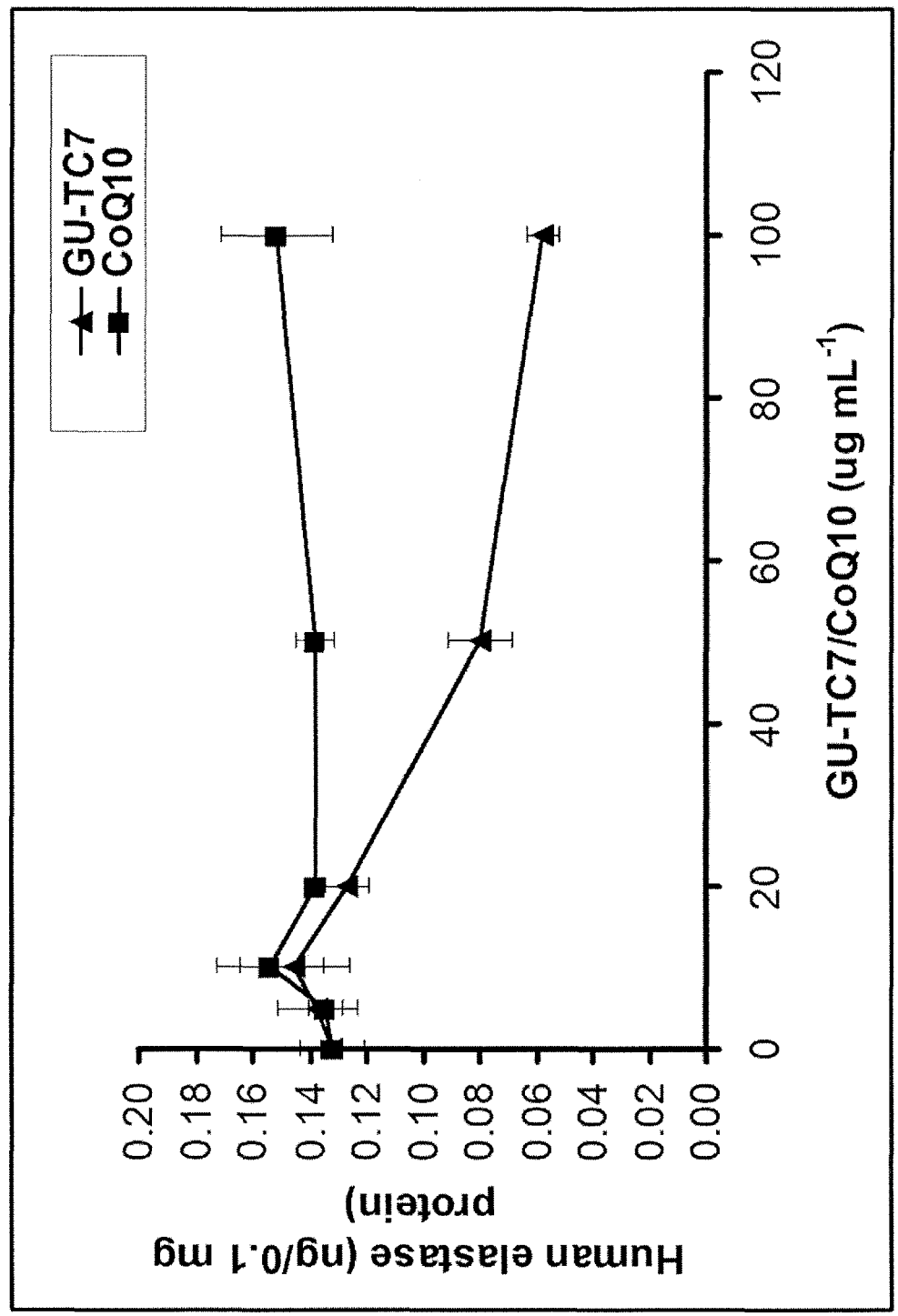
FIG. 5 is a graph showing inhibition of human elastase expression by GU-TC7 and CoQ10 in CCL-110 human fibroblast cell line.

The effect of GU-TC7 and CoQ10 on human elastase expression is shown in FIG. 5. GU-TC7 inhibits elastase expression significantly ($P<0.05$), whereas no such inhibition was evident with CoQ10. GUd-TC7 inhibits more than 50% of elastase at 100 µg mL$^{-1}$ concentration.

Discussion

Age and sun exposure contribute significantly to skin damage; with increasing age, the density of collagen and elastic fibres is reduced and elasticity decreases, impairing the protective benefits of the skin and predisposing an increased susceptibility to serious pathologies. Pharmaceutical and cosmeceutical agents, environmental factors, diseases and lifestyle also have important effects on skin. Wrinkles are a consequence of loss of skin elasticity in part because of decreased collagen production and collagen cross-linking. Coenzyme Q10, one of the major ingredients in the cosmetic skin care products, has been used topically as a cosmetic in Europe and the U.S.A., although because of its bright yellow to orange color, products with high concentrations of CoQ10 may cause discoloration of skin or fabrics. Topical application of products containing 0.3% coenzyme Q10 for approximately 6 months has demonstrated improvement of wrinkles (Hope, U. "Coenzyme Q10, a cutaneous antioxidant and energizer" *Biofactors*, 1999, 9:371-378). Coenzyme Q10, shown to be present in every cell of the body, was discovered in 1957. This vitamin-like substance is a powerful antioxidant and plays a major role in energy production (Wu, J. et al. "The hypolipidemic natural product guggulsterone acts as an antagonist of the bile acid receptor" *Mol. Endocrinol.*, 2009, 16:1590-1597). Its natural level in the human body decreases with age and is used as a supplement to inhibit various undesirable processes because of oxidative stress in the body and to promote energy production (Ashida, Y. et al. "Effect of coenzyme Q10 as a supplement on wrinkle reduction" *Food Style*, 2004, 21:1-4). Coenzyme Q10 has been reported to inhibit UVB-induced wrinkle formation in vitro and in vivo by reducing the production of IL-6 and MMPs in fibroblasts (Prahl, S. et al. "Aging skin is functionally anaerobic: importance of coenzyme Q10 for anti-aging skin care" *Biofactors*, 2008, 32:245-255; Inui, M. et al. "Mechanisms of inhibitory effects of CoQ10 on UVB-induced wrinkle formation in vitro and in vivo" *Biofactors*, 2008, 32:237-243). Furthermore, CoQ10 is reported to protect against oxidative stress-induced cell death and enhance the synthesis of basement membrane components in dermal and epidermal cells (Muta-Takada, K. et al. "Coenzyme Q10 protects against oxidative stress-induced cell death and enhances the synthesis of basement membrane components in dermal and epidermal cells" *Biofactors*, 2009, 35:435-441). However, oral use of CoQ10 has been associated with a number of side effects including heartburn, nausea, vomiting, loss of appetite, stomach upset, diarrhea, skin rash, insomnia, headache, fatigue, irritability and flu-like symptoms. Moreover, prolonged intake of CoQ10 at higher amounts has been shown to impair cognitive functions in older mice (Sumien, N. et al. "Prolonged intake of coenzyme Q10 impairs cognitive function in mice".*J. Nutr.*, 2009, 139:1926-1932). It has also been found to worsen the age-related losses in acuity to auditory and shock stimuli, and impaired the spatial learning/memory of old mice.

Coenzyme Q10 demonstrates little cytotoxicity and proliferative effects on skin fibroblasts but did demonstrate beneficial effects on two biomarkers of skin aging, viz., inhibition of MMP-1 expression and enhanced synthesis of type I collagen. However, a dose-dependent relationship between CoQ10 and type I collagen synthesis or MMP-1 inhibition was not clearly evident within the range of concentrations evaluated. This observation may in part be explained by greater potency of CoQ10 at lower concentrations. Additionally, CoQ10 showed no inhibition of elastase at any evaluated concentration. GU-TC7 also showed no evidence of cytotoxicity; however, it did demonstrate a mild increase in fibroblast proliferation at lower concentrations. GU-TC7 also demonstrated a dose-dependent increase in type I collagen synthesis, inhibition of MMP-1 with nearly complete inhibition at 50 µg mL$^{-1}$, and inhibition of elastase. Consequently, GU-TC7 has the potential to be a protective and restorative cosmetic ingredient.

Example 3

Functional Assessment of Two Supercritical Carbon Dioxide GUGGUL Extract Compositions (GU-MCT810 and GU-TC7)

The inventors have investigated the development of supercritical carbon dioxide guggul extracts for the treatment of metabolic syndrome; hypercholesterolemia, obesity, insulin resistance and hypertension. The inventors' screening process has identified an oleoresin of *Commiphora wightii* bark; guggul, that is rich in sterols, sterones and other chemicals that alone—or in synergy—target the principle conditions associated with metabolic syndrome. Two refined fractions have to date demonstrated (1) potent inhibition of HMG-CoA reductase, comparable to the statin drugs for hypercholesterolemia, (2) inhibition of differentiation of preadipocytes to adipocytes and inhibition of triglyceride storage and (3) marked promotion of insulin sensitivity in adipocytes as measured by enhanced glucose uptake at levels beyond thiazolidinedione drugs, (4) stimulation of AMPK (nutrient/energy sensor), an upstream target of pharmaceuticals for treatment of hyperglycemia and (5) increase of the NAD/NADH ratio and increased NAD (Shishodia S. et al., "The Guggul for Chronic Diseases Ancient Medicine, Modern Targets," *Anticancer Research*, 2008, 28:3647-3664; Burris T. B. et al. "The Hypolipidemic Natural Product Guggulsterone Is a Promiscuous Steroid Receptor Ligand," *Molecular Pharmacology*, 2005, 67:948-954; Yang J-Y. et al. "Guggulsterone Inhibits Adipocyte Differentiation and Induces Apoptosis in 3T3-L1 Cells", *Obesity*, 2008, 16:16-22; Urizar N. L. et al., "A Natural Product That Lowers Cholesterol As an Antagonist Ligand for FXR," *Science*, 2002, 296; 1703-1706; and Ervin R B, "Prevalence of Metabolic Syndrome Among Adults 20 Years of Age and Over, by Sex, Age, Race and Ethnicity, and Body Mass Index: United States, 2003-2006. National Health Statistics Reports, 2009, 13; 1-4).

A novel feature of this approach is that chemical compounds within the two bioactive fractions identified are directed at upstream molecular targets that normalize the component conditions associated with metabolic syndrome. Current drug therapies for metabolic syndrome target each disorder independently and while improving one of the conditions, current drugs may also antagonize other conditions. For example, thiazolidinedione drugs which are PPAR-γ agonists effectively promote insulin sensitivity and glucose uptake thus treating hyperglycemia. However, these drugs have also been reported to exacerbate obesity, another component of metabolic syndrome. Furthermore, some drugs in this family are now being cited for cardiac toxicities, potentially jeopardizing their future use.

Current therapies for metabolic syndrome target each disorder independently and while improving one of the conditions, current drugs may also antagonize other conditions. The bioactive fractions of the invention target upstream molecular targets, thereby normalizing the component conditions associated with metabolic syndrome. This approach provides increased therapeutic efficacy compared with current therapies.

Metabolic syndrome represents an unmet need in healthcare by virtue of the fact that multiple approaches for the treatment of this disorder have failed to reduce or halt the growing prevalence of this disease or curtail the economic sequale to the healthcare system and society. Metabolic syndrome is considered to be a chronic disease. Furthermore, this disease is associated with increased risk for cancer, heart disease and other chronic diseases. The inventors have identified two refined fractions that demonstrate strong activity on upstream metabolic syndrome targets. A recent two-year multi-center study (*Metabolic Syndrome and Related Disorders*, 2009; 7:305) demonstrated that risk factors for metabolic syndrome (34% prevalence in adults-CDC) increases a persons healthcare costs nearly 1.6-fold. The therapy being developed is in part aimed at reducing this economic burden through amelioration of this disease.

*Commiphora wightii* bark is the source of an oleoresin known as guggul in Ayurvedic literature. The oleoresin is a mixture of terpenoids, steroids, esters and alcohols. Guggulsterone, one of the active components has been shown to be an agonist for the Farnesoid X receptor which plays a fundamental role in maintaining bile acid, cholesterol, glucose and triglyceride metabolism homeostasis. Evidence exists that guggulsterone is effective in inhibiting adipocyte differentiation; hence, a role in controlling obesity. Evaluation of the oleoresin chemistry suggests the presence of other compounds that are beneficial for the spectrum of disorders in metabolic syndrome and are amenable for drug development.

The present inventors have developed functional assays to measure the effectiveness of refined fractions of the resin for inhibition of HMG-CoA reductase (the most upstream target of cholesterol synthesis), inhibition of adipocyte differentiation (anti-obesity) and stimulation of glucose uptake (promotion of insulin sensitivity) in adipocytes and the upstream targets, AMPK and NAD/NADH ratio that play a role in the modulation of these mechanisms. The inventors have identified two fractions, GS and GSE that demonstrate positive effects in each case and are proceeding with isolation of unique molecules. These extracts have been blended together to form GU. GU was solubilzed in triheptanoin (TC-7; a medium chain triglyceride used as a food additive that appears to act synergistically with GU and provides a convenient method of delivery), or C8 and C10 fatty acids (caprylic/capric triglyceride), and evaluated as described below. The mixture of GU and triheptanoin is referred to herein as GU-TC7 or GU-TC. The mixture of GU and C8 and 10 fatty acids is referred to herein as GU-MCT810 or GU-MCT.

Materials and Methods

HMG Co-A Reductase Activity.

HMG Co-A activity was measured using the HMG Co-A reductase activity assay kit from Sigma Chemical Co., MO. The inhibitory effect of low levels of guggul extracts (0-0.1 ug) on HMGCR activity was estimated in a kinetic assay protocol. The percentage of inhibition was plotted against extract concentrations. The positive controls 0.04 ug Pravastatin and Mevastatin.

HDL and LDL/VLDL Cholesterol Quantification.

HepG2 cells ($2\times10^6$) were incubated with increasing concentrations of Glucodox (0-100 ug/ml) for 72 hours at 37° C. The cells, after washing with PBS, were lysed with methanol:choloroform ( ) solution. Both HDL an LDL fractions were separated and estimated using the HDL and LDL/VLDL quantification kit (MBL International Corporation, MA).

Adipocyte Staining and Quantification.

3T3-LI preadipocytes were cultured in DMEM medium to confluency. To induce differentiation, 2-day post-confluent preadipocytes were stimulated for 72 hours by adding 0.5 mM 3-isobutyl-1-methylxanthine, 1 uM dexamethasone, 0.125 mM indomethacin and 1 uM insulin (MDI) to the DMEM/10% FBS medium. Subsequently, on day 3, the MDI was replaced with DMEM/10% FBS containing 1 uM insulin. On day 5 again MDI medium was replaced with fresh MDI-insulin medium. On day 7 cells medium was aspirated out and 10% formalin was added. After 5 min the wells were replaced with fresh formalin solution and the plate was incubated for 1 hour at room temperature. The formalin was removed and wells were washed with 60% isopropanol. The wells were allowed to dry for 1 min and stained with Oil Red O solution (0.42%) The Oil Red O solution was removed immediately and wells were washed with water four times. Water was removed completely and wells were dried for 20 min. The Oil Red O solution was eluted with 100% ethanol for 10 min and absorbance was measured at 500 nm. Since the intensity of staining corresponds to adipocyte differentiation, the inhibitory effect of guggul extracts on adipocyte formation was estimated based on untreated controls.

Glucose Uptake:

3T3-LI preadipocytes were used for glucose uptake and they were differentiated in the same manner as for adipocyte staining. The differentiated adipocytes ($0.5\times10^6$) were treated with increasing concentrations (2-100 µg/ml) of guggul extracts for 72 hours in DMEM medium containing 1 µM insulin. 2,4-Thiazolidinedione (0.005 µM-0.1 µM) was used as a positive control for comparison. After 72 hours, the medium was replaced with starving medium (DMEM without FBS) for 2 hours at 37° C. and then with 3 ml KRH buffer (136 mM NaCl, 4.7 mM KCl, 1.25 mM CaCl2, 1.25 mM Mg SO4, 10 mM Hepes, pH 7.4) with 1 uM insulin at 37° C. for 30 min. For glucose uptake, 4.5 mg/ml glucose was added into the KRH buffer and plates were incubated for another 15 min. The plates were washed 4 times with KRH buffer, cells were lysed with RIPA buffer (0.5 ml/plate). The protein concentration of the extract was estimated and 500 ug extract was used for glucose estimation using the assay kit from Sigma Chemical Co., MO. The absorbance of the reaction mixture was measured at 340 nm and glucose concentration calculated.

Alpha Glucosidase Activity.

The inhibitory effect of guggul extracts against yeast alpha-glucosidase was determined by measuring the formation of p-nitrophenol by alpha-glucosidase after reaction with p-nitrophenyl-alpha-D-glucopryanoside substrate in the presence and absence of guggul extracts (Bramnono et al. 2006). The 200 ul reaction mixture containing alpha glucosidase (0.1 U, guggul extract and PBS was incubated at 37° C. for 15 min, followed by addition of 100 ul of 0.2 uM PNP and subsequent incubation for another 30 min at 37° C. The reaction was stopped by incubating at 100° C. for 10 min and 200 µl of 1M sodium carbonate solution was added before the calorimetric measurement at 405 nm in a multi-well plate reader. The percentage of inhibition of alpha glucosidase activity was calculated and plotted against extract concentrations.

Results

Inhibition of HMG-CoA Reductase by Guggul Extracts

Inhibition of HMG-CoA reductase is beneficial for promoting healthy cholesterol levels within the normal range (Izzat N. N. et al., "New molecular targets for cholesterol-lowering therapy," *The Journal of Pharmacology and Experimental Therapeutics*, 2000; 293:315-320; Goldstein J. L. and Brown M. S., "Regulation of the mevalonate pathway," *Nature*, 1990, 343:425-430). HMG-CoA reductase is a pharmaceutical target for reduction of plasma cholesterol, specifically LDL.

Figure 6:
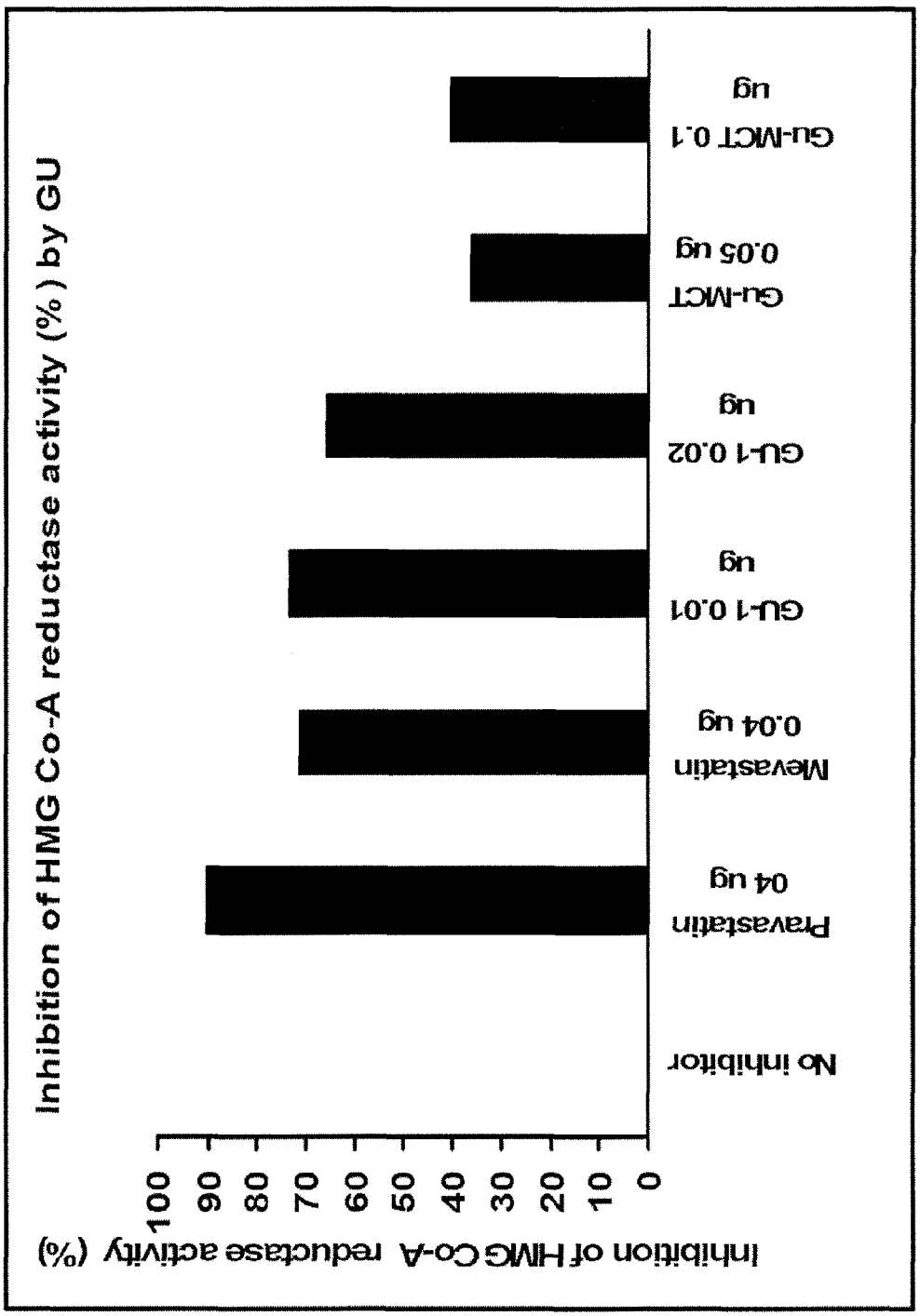
FIG. 6 is a graph showing inhibition of HMG-CoA reductase by GU-MCT810 (blend of GU and C8 and C10 fatty acid triglycerides).
Figure 13:
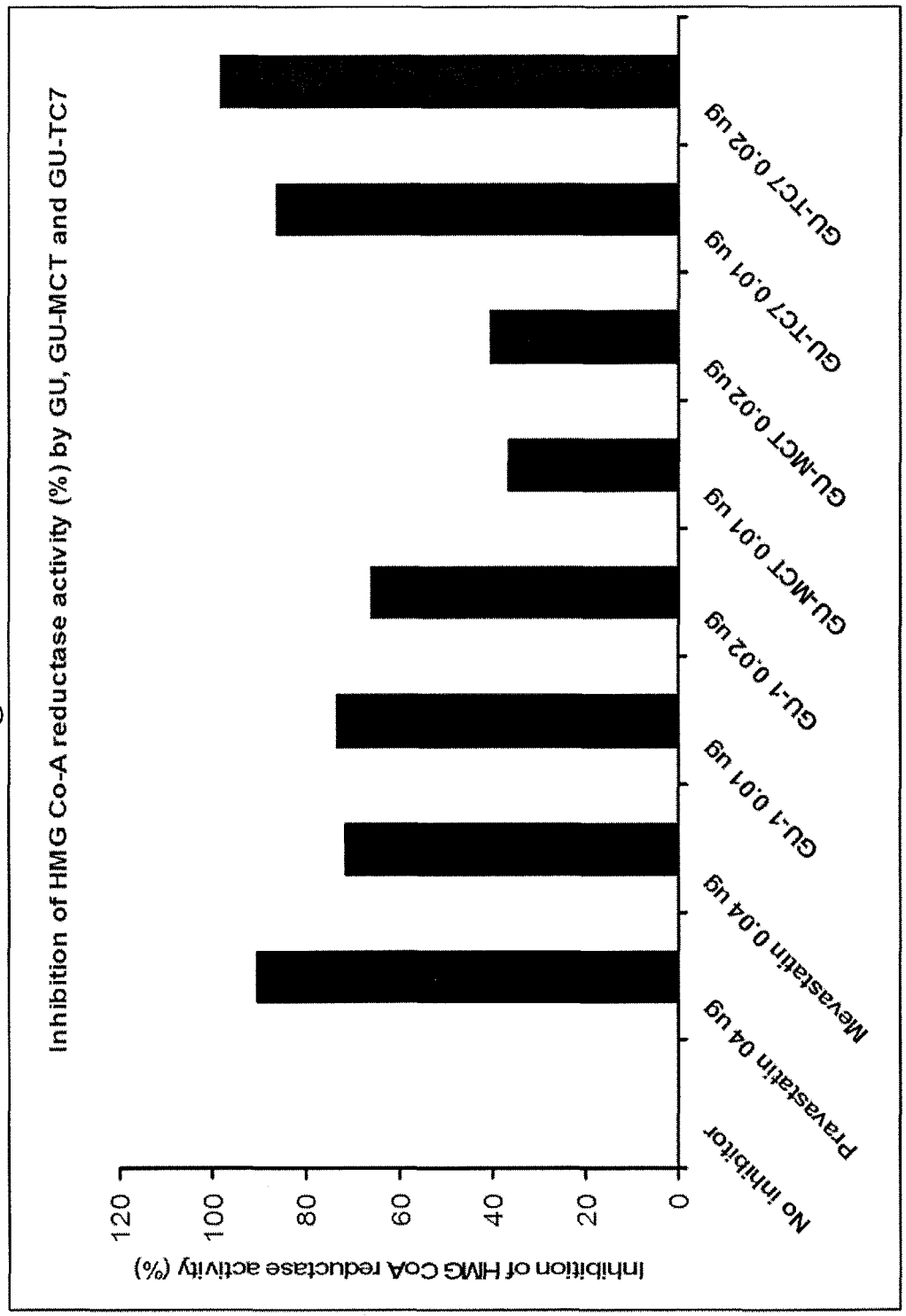
FIGS. 13 and 14 are graphs showing inhibition of HMG-CoA reductase by Guggul preparations of the invention.
Figure 14:
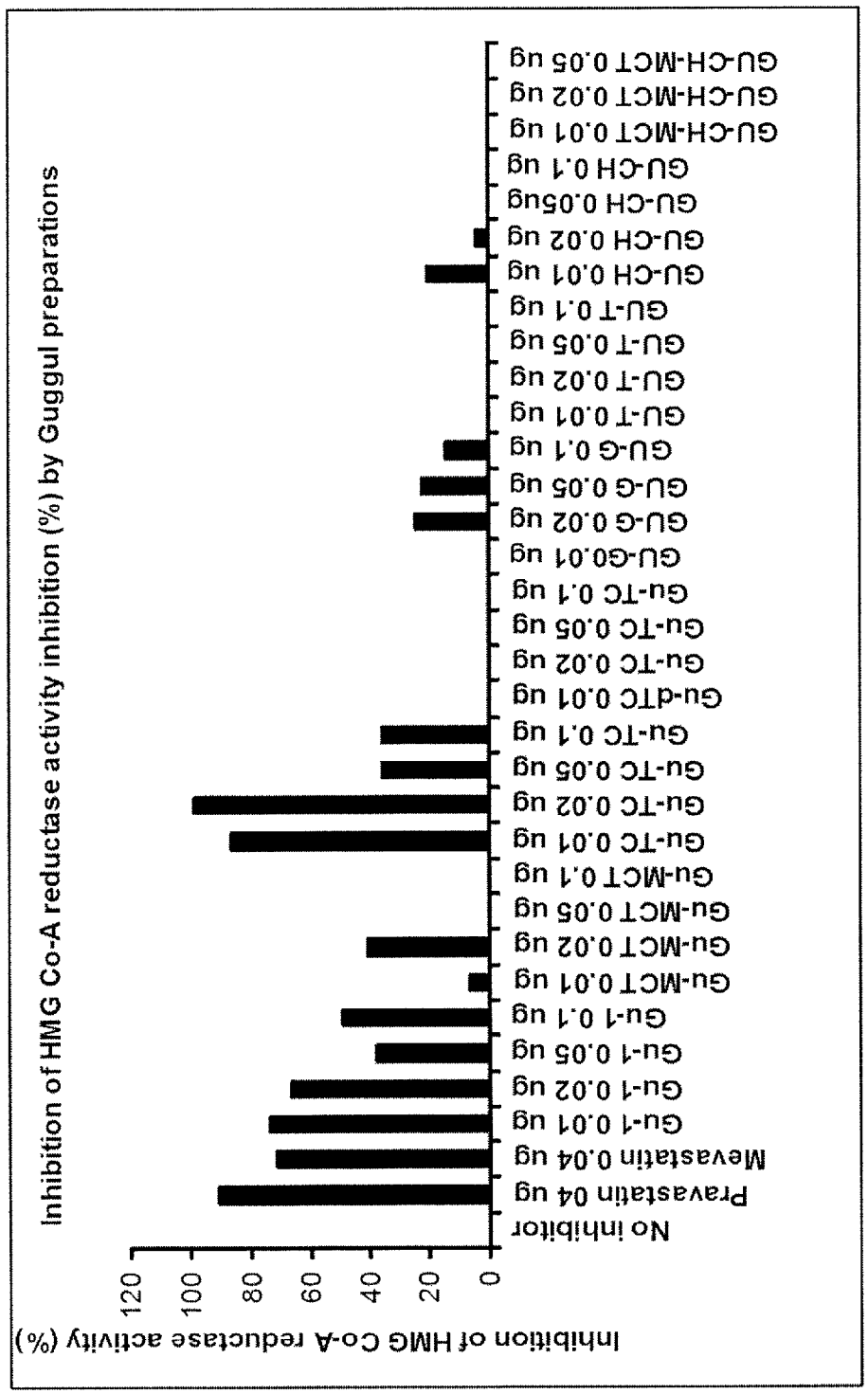

Very good efficacy was seen for the GU extracts. GU-MCT810 showed HMG-CoA reductase inhibitory activity comparable to mevastain (FIG. 6). GU-TC7 also showed good efficacy (FIG. 13). However, it was learned that this cell-free assay required the use of lower concentrations of test products. FIG. 14 clearly shows GU-TC7 to be more effective than Pravastatin and Mevastatin for inhibition of HMG-CoA reductase. In this study, GU-MCT810 was also effective but not to the degree of GU-TC7 so the carrier used does matter. Other compounds are GU-G (combined with ginger extract) and GU-CH (combined with chia seed oil).

Inhibition of Adipocyte Differentiation by Guggul Extracts

The 3T3-L1 cell line is a pre-adipocyte cell line that is commonly used to evaluate properties related to lipid metabolism (Yang J-H. et al., "Guggulsterone inhibits adipocyte differentiation and induces apoptosis in 3T3-L1 cells," *Obesity*, 2008, 16:16-22; Rizzo G, et al., "The farnesoid X receptor promotes adipocyte differentiation and regulates adipose cell function in vivo, "*Mol Pharmacol.* 2006, 70:1164-1173). If these pre-adipocytes are allowed to remain in culture without interference, over time they will differentiate and store lipid. This assay is used to show the inhibition of this process by the guggul extracts and represent a surrogate for reduced lipid uptake.

Figure 7:
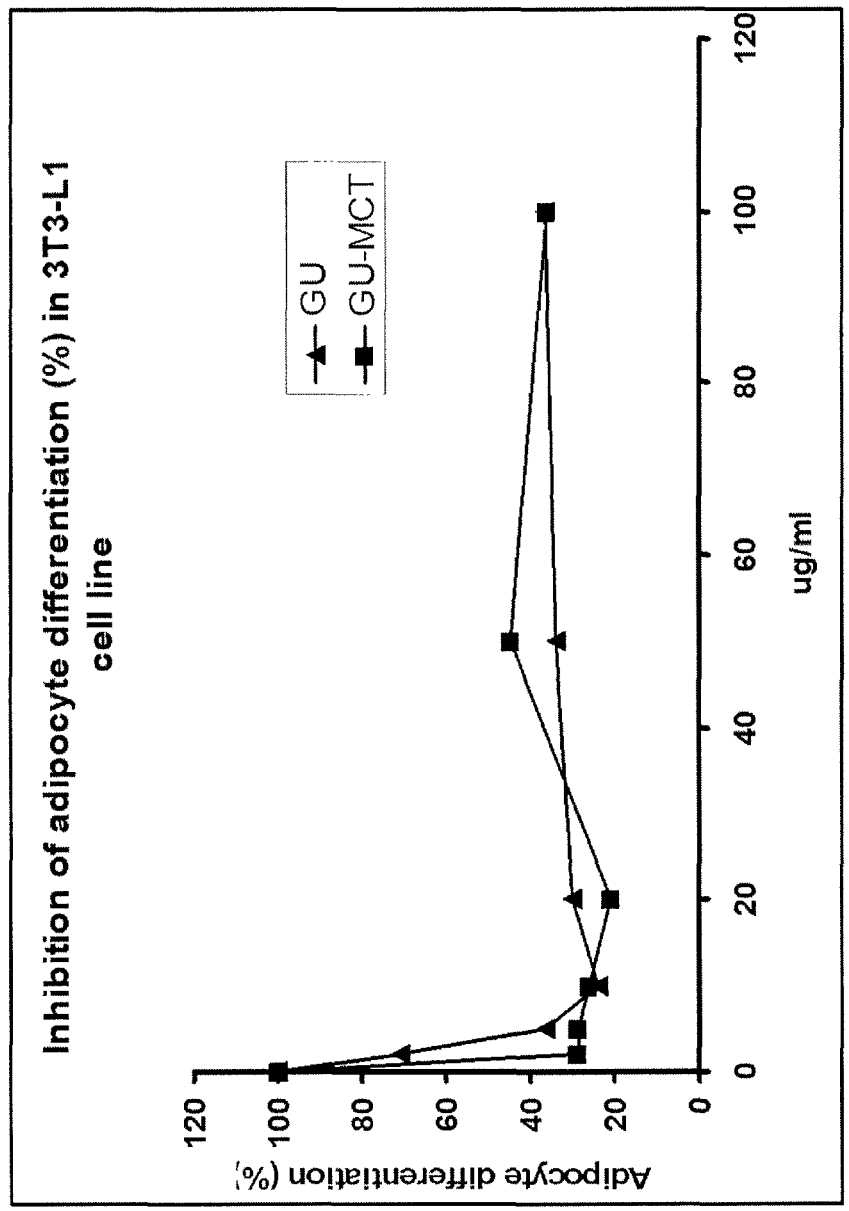
FIG. 7 is a graph showing inhibition of adipocyte differentiation by GU-MCT810 in the 313-L1 cell line.
Figure 15:
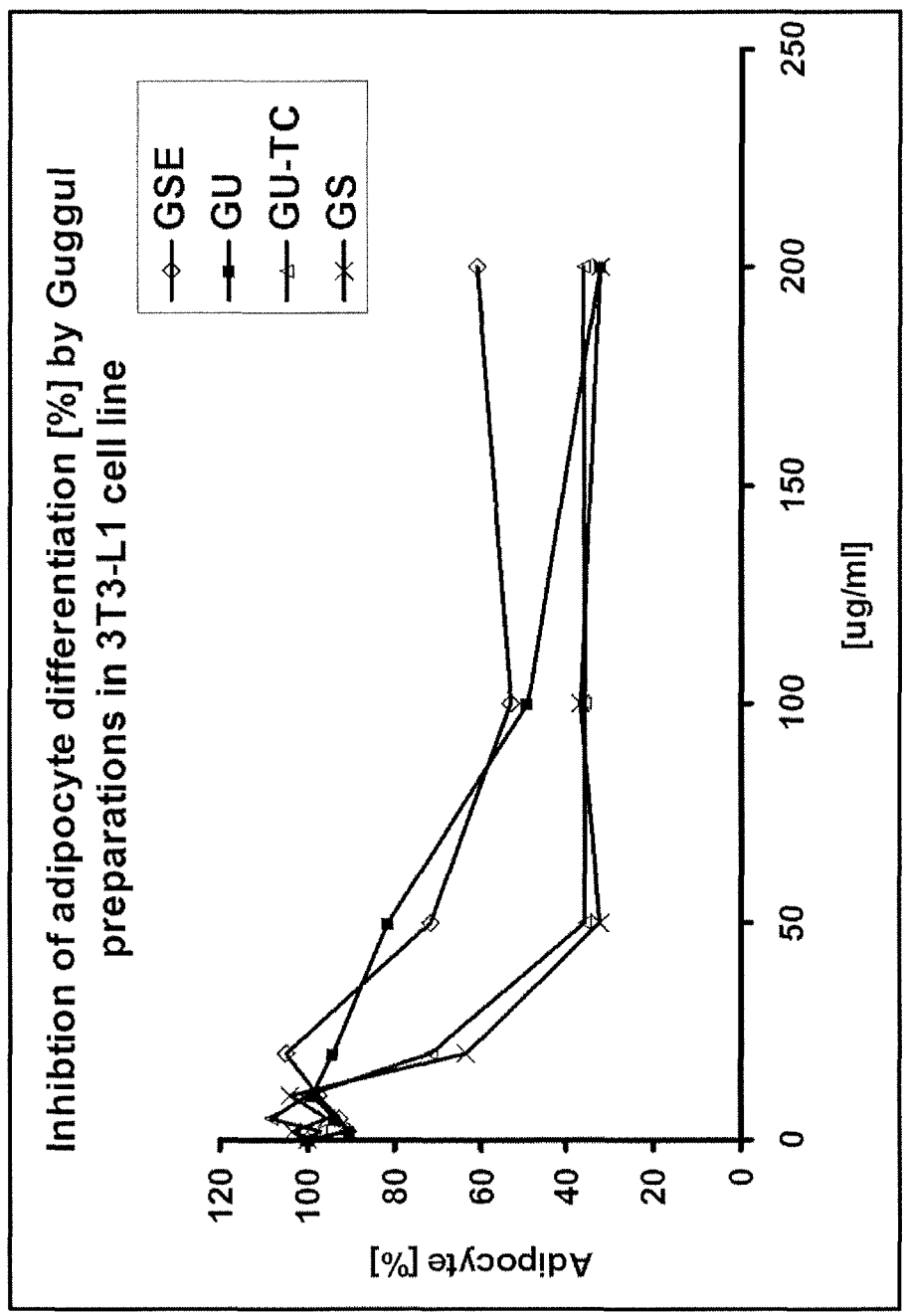
FIG. 15 is a graph showing inhibition of adipocyte differentiation by GU-TC7 in the 3T3-L1 cell line.

In the experiment shown in FIG. 7, GU-MCT810 was the most effective, especially at low concentrations. In the experiment shown in FIG. 15, GU-TC7 was the most effective, especially at low concentrations.

Increased Glucose Uptake by Guggul Extracts

The measure of glucose uptake in 313-L1 pre-adipocytes is a surrogate measure for insulin sensitivity which is an important clinical target for type 2 diabetes and metabolic syndrome (Shishidia S. et al., "The guggul for chronic diseases: Ancient medicine, modern targets," *Anticancer Res*, 2008, 28:3647-3664; Gruzman A, and Sasson S., "Adenosine monophosphate-activated protein kinase (AMPK) as a new target for antidiabetic drugs: A review on metabolic, pharmacologic and chemical considerations," *Rev Diabet Stud*, 2009, 6:13-36; Zhang B. B. et al., "AMPK: and emerging drug target for diabetes and the metabolic syndrome," *Cell Metabolism*, 2009, 9:407-416; Claudel T. et al., "The farnesoid X receptor: A molecular link between bile acid and lipid and glucose metabolism Arterioscler Thromb Vasc Biol.," 2005, 25; 2020-2030; and Stayrook K. R. et al., "Regulation of carbohydrate metabolism by the farnesoid X receptor," *Endocrinology*, 2005; 146:984-991).

Figure 8:
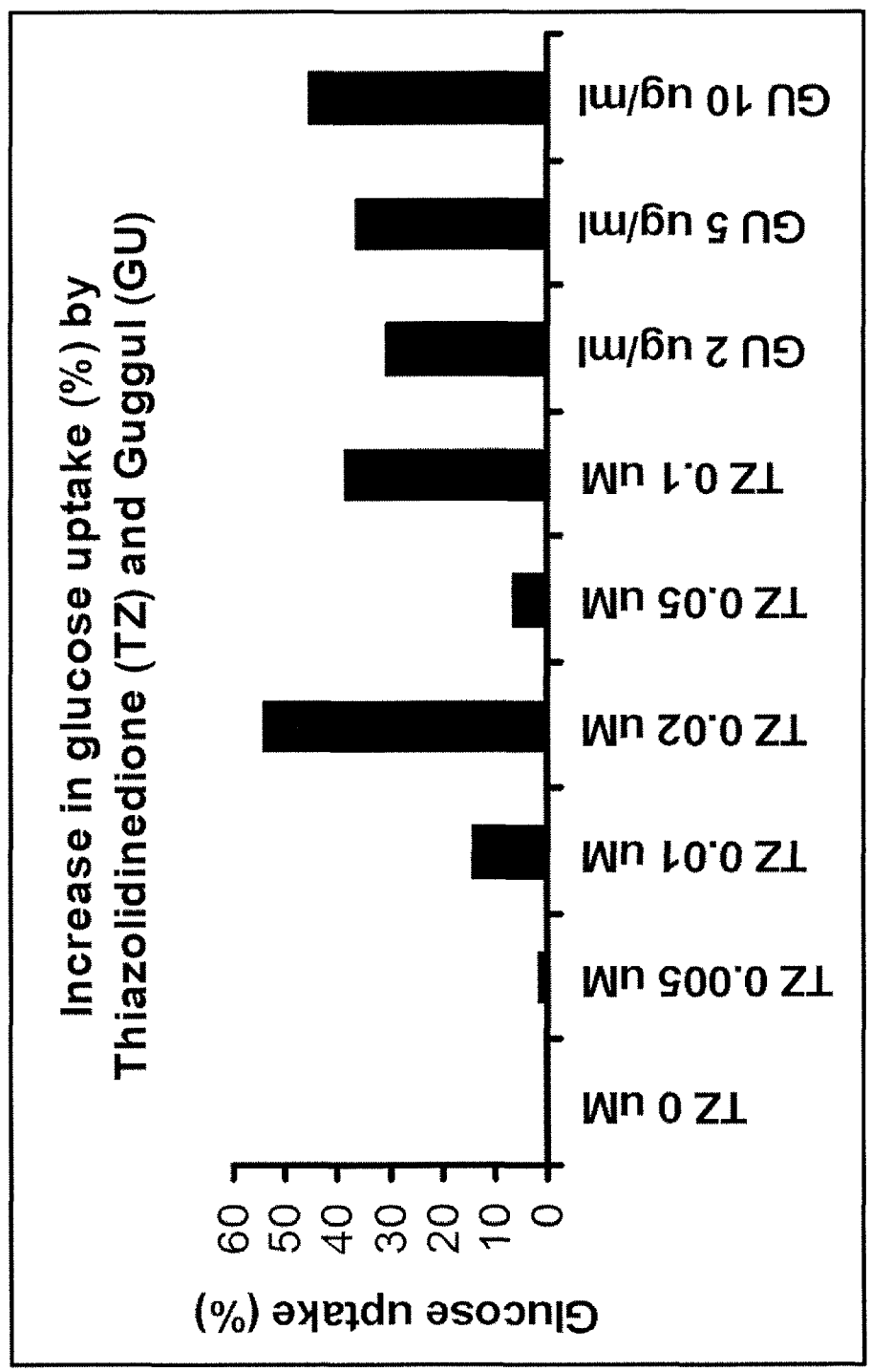
FIG. 8 is a graph showing the effect of GU-MCT810 on glucose uptake (%).
Figure 16:
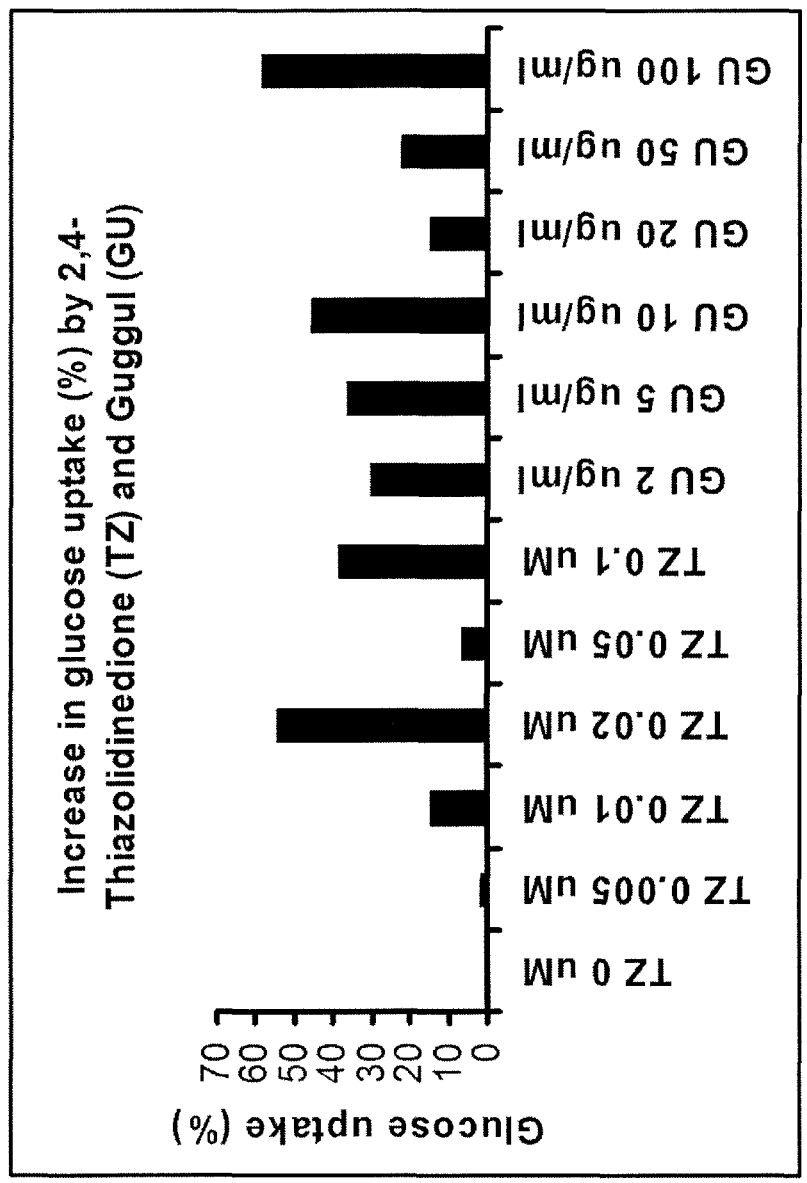
FIGS. 16 and 17 are graphs showing the effects of GU-TC7 on glucose uptake (%).
Figure 17:
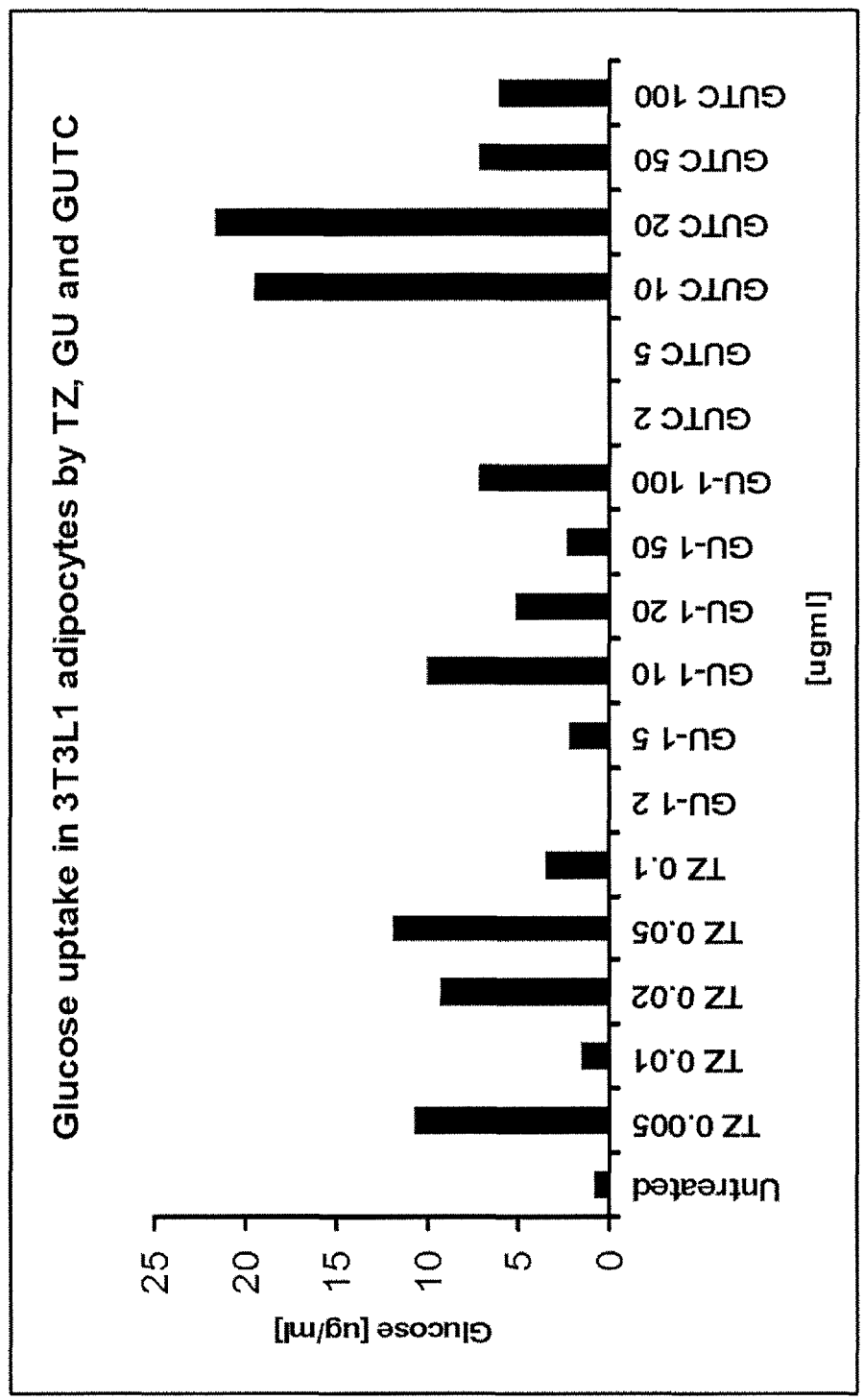
Figure 23:
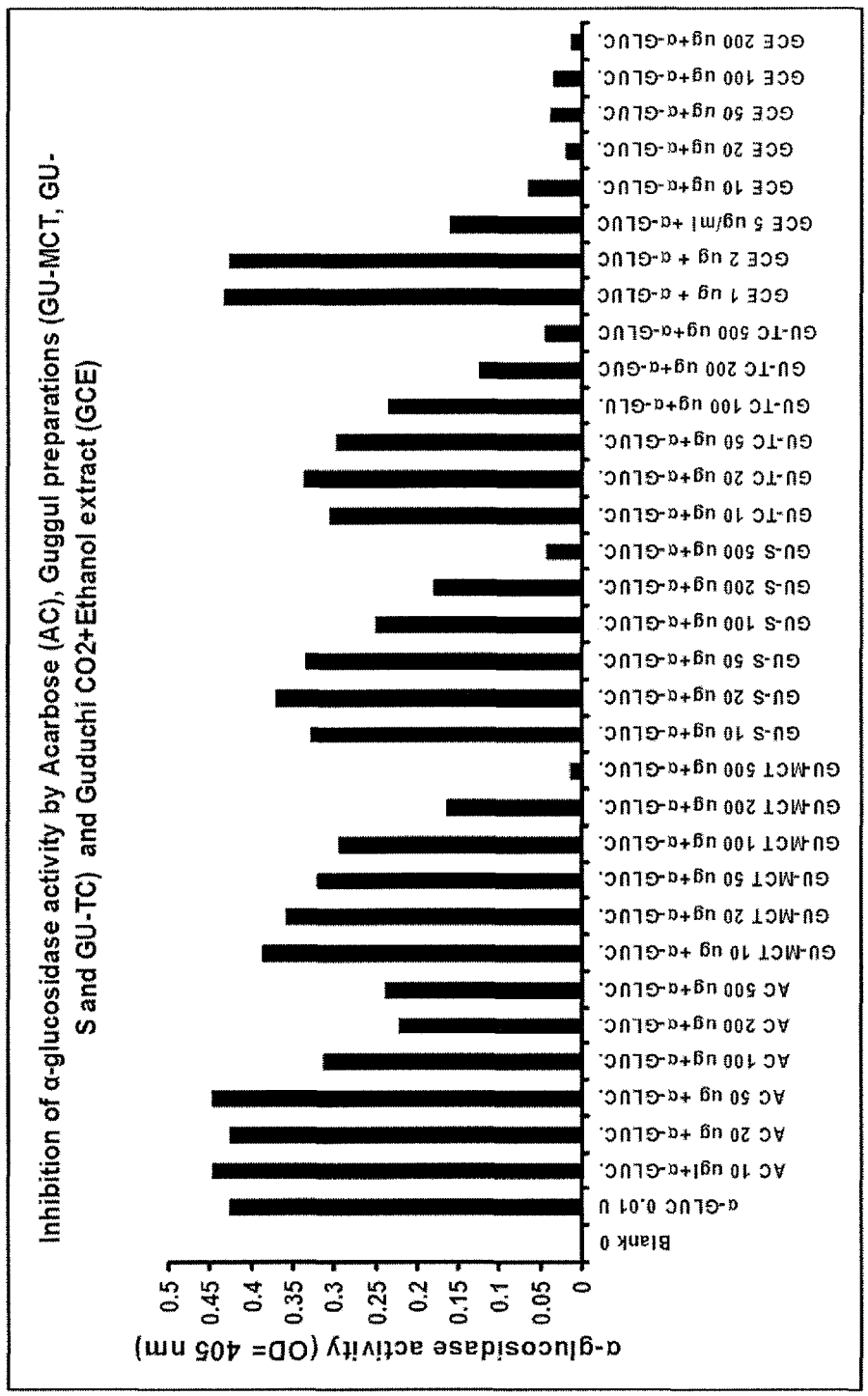
FIG. 23 is a graph showing inhibition of alpha-glucosidase activity by GU-MCT810 (GU-MCT) and GU-TC7 (GU-TC), as well as GU-S and Guduchi carbon dioxide+ethanol extract (GCE).

2,4 Thiazolidinedione is a pharmaceutical therapy and is more potent than the guggul extracts; however, both GU-MCT810 (FIG. 8) and GU-TC7 (FIGS. 16 and 17) exert an effect at concentrations that may be achieved with oral doses. FIG. 23 shows the inhibitory effects of GU-MCT810 (GU-MCT) and GU-TC7 (GU-TC) on alpha-glucosidase activity relative to acarbose (AC), GU-S, and Guduchi carbon dioxide+ethanol extract (GCE).

Increased AMPK Activity by Guggul Extracts

Stimulation of AMPK (nutrient/energy sensor) is an important target that also helps to naturally reduce blood sugar levels within the normal range (Zhang B. B. et al., "AMPK: and emerging drug target for diabetes and the metabolic syndrome," *Cell Metabolism*, 2009, 9:407-416; Lage R. et al., "AMPK: a metabolic gauge regulating whole-body energy homeostasis," *Trends in Molec Med.*, 2008, 14:539-549; Long Y. C., and Zierath J. R., "AMP-activated protein kinase signaling in metabolic regulation," *J Clin Invest.*, 2006, 116:1776-1783; Canto C. et al., "AMPK regulates energy expenditure by modulating NAD metabolism and SIRT1 activity," *Nature*. 2009, 458:1056-1062; Steinberg G. R., and Kemp B. E., "AMPK in health and disease," *Physiol Rev.*, 2009, 89:1025-1078; Hardie D. G. et al., "AMP-activated protein kinase-development of the energy sensor concept," *J Physiol.*, 2006, 574:7-15; Hardie D. G., "The AMP-activated protein kinase pathway-new players upstream and downstream," *J Cell Sci.* 2004, 117: 5479-5487; Lim C. T. et al., "AMPK as a mediator of hormonal signaling," *Journal of Molecular Endocrinology*, 2010, 44:87-97; Osler M. E., and Zierath J. R. "Minireview: Adenosine 5'-monophosphate-activated protein kinase regulation of fatty acid oxidation in skeletal muscle," *Endocrinology*, 2008, 149:935-941; and Hardie D. G. and Sakamoto K. "AMPK: A key sensor of fuel and energy status in skeletal muscle," *Physiology*, 2006, 2:48-60).

Arguably, the key sensor and effector of energy balance at a cellular level is 5' adenosine monophosphate-activated protein kinase (AMPK). Activation of AMPK occurs through phosphorylation via different feedback mechanisms or other signaling events. Specific responses to AMPK vary by cell type and organ. This variation reflects the different needs and functions of organs and systems with respect to management of energy metabolism. The role of AMPK that is common to all cells is the sensing of energy depletion or excess and the activation of pathways that regulate these conditions. This principle may be illustrated by considering the energy deficient state in a cell. The subsequent phosphorylation of AMPK will induce a state of catabolism with complementary attenuation of energy consumption in the peripheral organs, until the energy stores are replenished. One of several mechanisms that phosphorylate AMPK is the increased AMP/ATP ratio. The resulting phosphorylation of AMPK that replenishes ATP signals an up-regulation of a large number of important downstream molecular pathways; PGC-1α, SIRT-1, FOXO and $NAD^+$. These products induce phosphorylation of AMPK that stimulates the FOXO pathway to enhance anti-oxidation mechanisms. AMPK phosphorylation also up-regulate PGC-1α that promotes mitochondrial biogenesis, increase catabolism and reduce lipid synthesis, increase autophagy, etc. The reflex to this stimulus is to ensure survival and health. However, this assurance will be forfeited if the capacity of these mechanisms is exceeded.

AMPK phosphorylation leads to a switch from a state of energy consumption to energy production. The latter involves catabolism and corresponds to a state where ROS is low, $\Delta\psi m$ (mitochondrial membrane potential) is very low and various downstream events which are focused on energy production and efficiency are engaged; mitochondrial biogenesis (PGC-1α), up-regulation-of SIRT-1, FOXO, TOR, PPARγ (another important target for inducing insulin sensitivity) and the modulation of a variety of functions related to, insulin sensitivity, increased lipid oxidation, increased glycolysis, decreased fatty acid and triglycerol synthesis, decreased autophagy, decreased apoptosis, increase antioxidant defenses, activations of defense mechanisms that relate to survival, etc. Once the deficit of ATP is corrected, the system reverts to the normal sensitive tone of AMPK readiness (to respond). Another important downstream event as mentioned is the increase in $NAD^+/NADH$ in response to the up-regulation of AMPK phosphorylation. $NAD^+$ is also associated with many vital downstream cellular events. In essence, it is possible to connect virtually all major molecular pathways and systems; endocrine system, inflammatory system, immune system, etc. from the AMPK and $NAD^+$ axis.

Drugs such as metformin are now targeting AMPK to restore insulin sensitivity and reduce lipid synthesis. However, drugs have side effects. There is an enormous opportunity for safe natural solutions to supplement diet and exercise.

From the analytical perspective, it seems that AMPK is an appropriate target to consider and may well be the fulcrum for this balance. Why focus on AMPK when there are so many other intracellular molecular and metabolic pathways? AMPK is a significantly upstream sensor and is connected directly or indirectly (through $NAD^+/NADH$) to most if not all other downstream pathways. Furthermore, the degree or type of response of AMPK phosphorylation is cell-type dependent and it appears to be fundamental to the coordination of the metabolic responses in different organs that occurs via the endocrine system. This coordination involves a host of positive and negative feedback loops. If this model is accurate, it should be possible to show that regulation of AMPK phosphorylation results in balance of downstream effects. To a certain extent, this has been demonstrated using several recently implemented models described herein. In this research, a number of natural compounds were shown to concomitantly induce insulin sensitivity (demonstrating usefulness for type 2 diabetes treatment), inhibit adipocyte differentiation (demonstrating usefulness for treatment of obesity) and inhibit HMG-CoA reductase (demonstrating usefulness for the reduction of cholesterol). In contrast, drugs such as thiazolidinediones, which effectively promote insulin sensitivity, also promote obesity. Therefore, the effects of these types of drugs must be relatively downstream. The fact that it can be demonstrated that natural compounds can promote all three targets in the desired direction means that balance is restored from a more upstream perspective; most likely AMPK.

Figure 9:
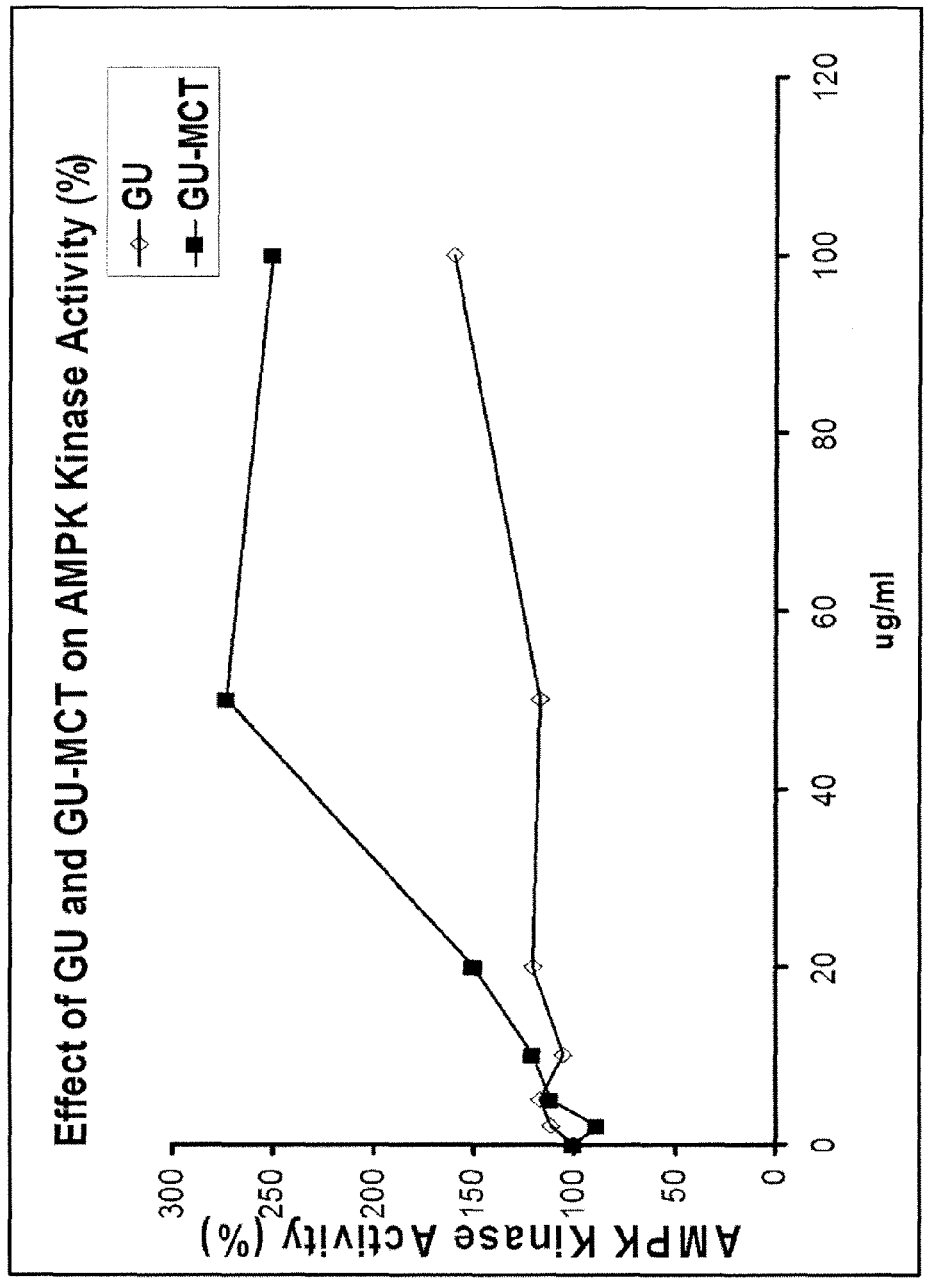
FIGS. 9 and 10 are graphs showing the effect of GU-MCT810 on AMPK activity in the HepG2 cell line.
Figure 10:
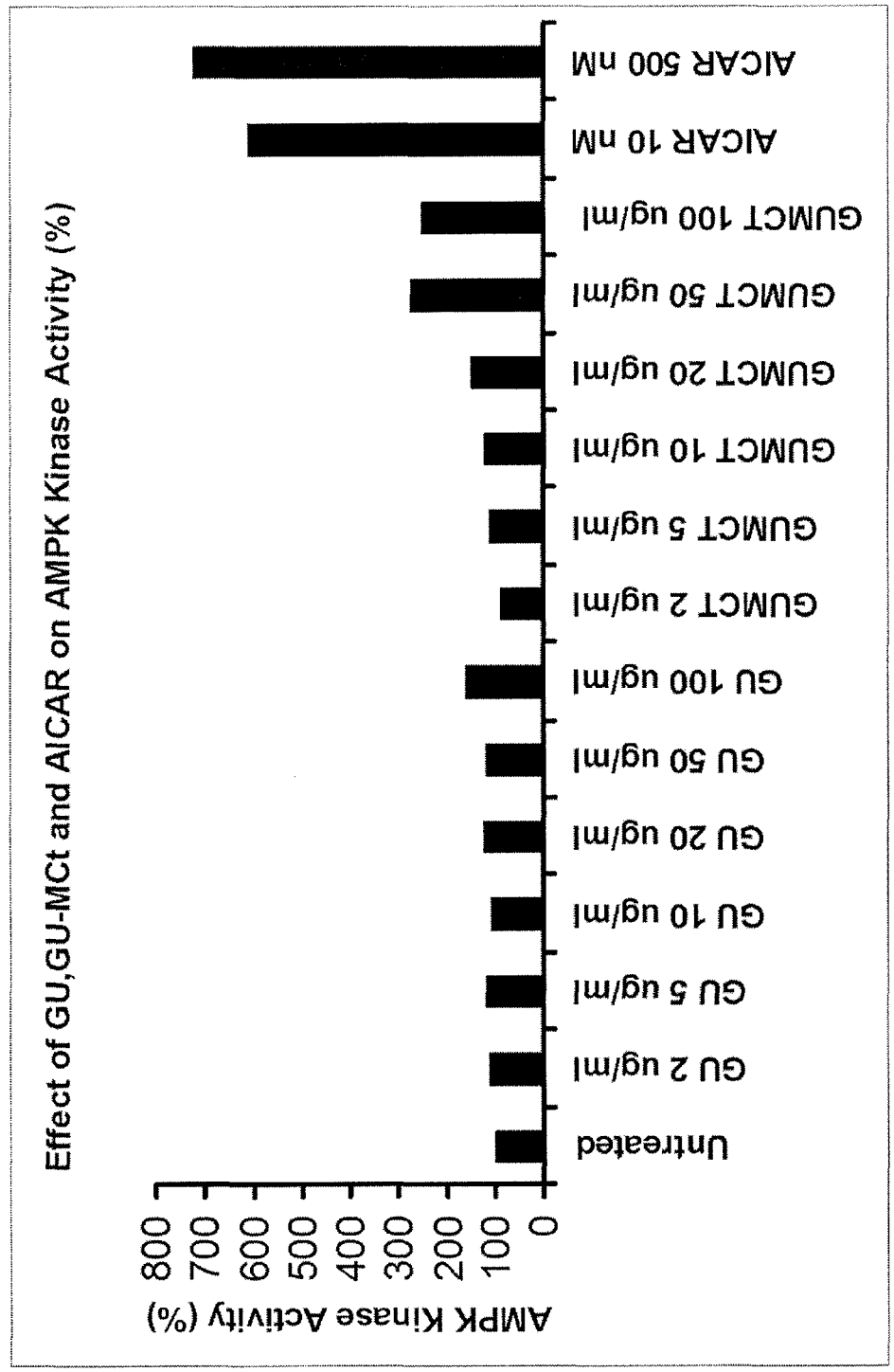
Figure 11:
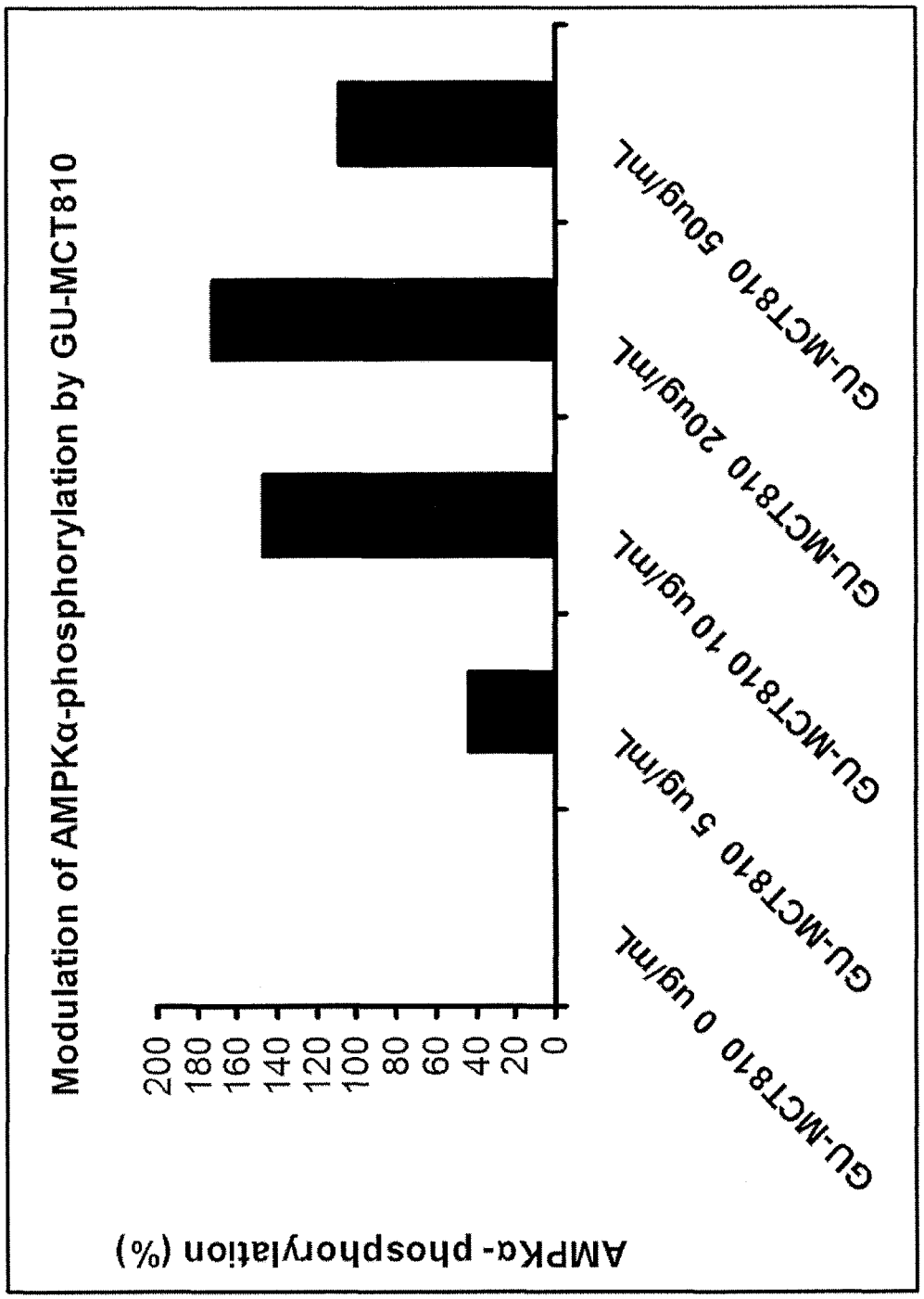
FIG. 11 is a graph showing the effect of GU-MCT810 on phosphorylation of AMPK α1.

FIGS. 9 and 10 demonstrate the effect of GU and GU-MCT810 on AMPK activity in the HepG2 cell line. FIG. 11 shows the effect of GU-MCT810 on the induction of phosphorylation of AMPK α1 which is necessary for activation of AMPK activity. The level of phospho AMPKα1 increased from 318 pg/ml to 863 pg/ml at 20 ug/ml GU-MCT concentration.

Figure 18:
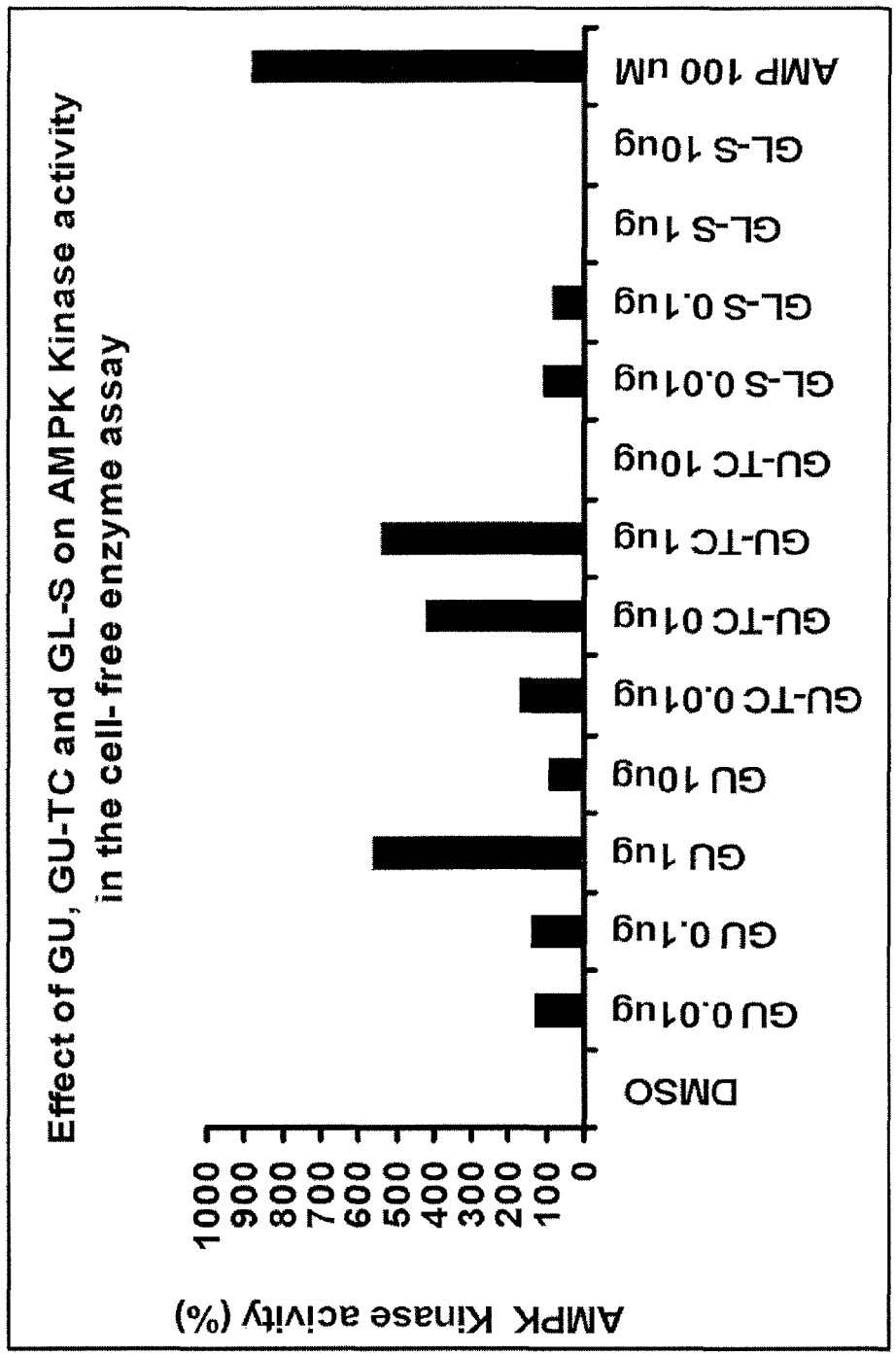
FIG. 18 is a graph showing the effect of GU-TC7 on AMPK activity in a cell-free enzyme assay.
Figure 19:
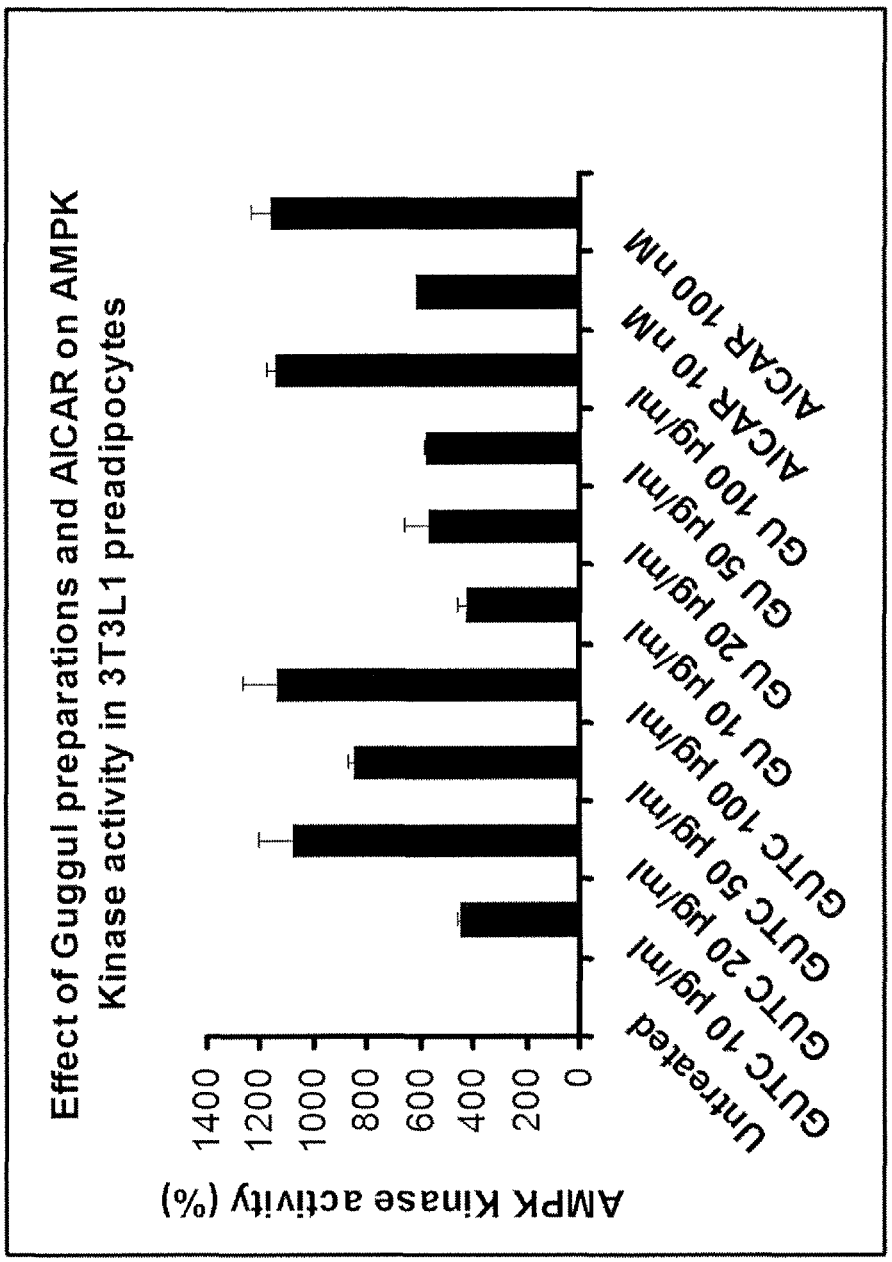
FIGS. 19 and 20 are graphs showing the effects of GU-TC7 on AMPK activity in 3T3L1 pre-adipocytes.
Figure 20:
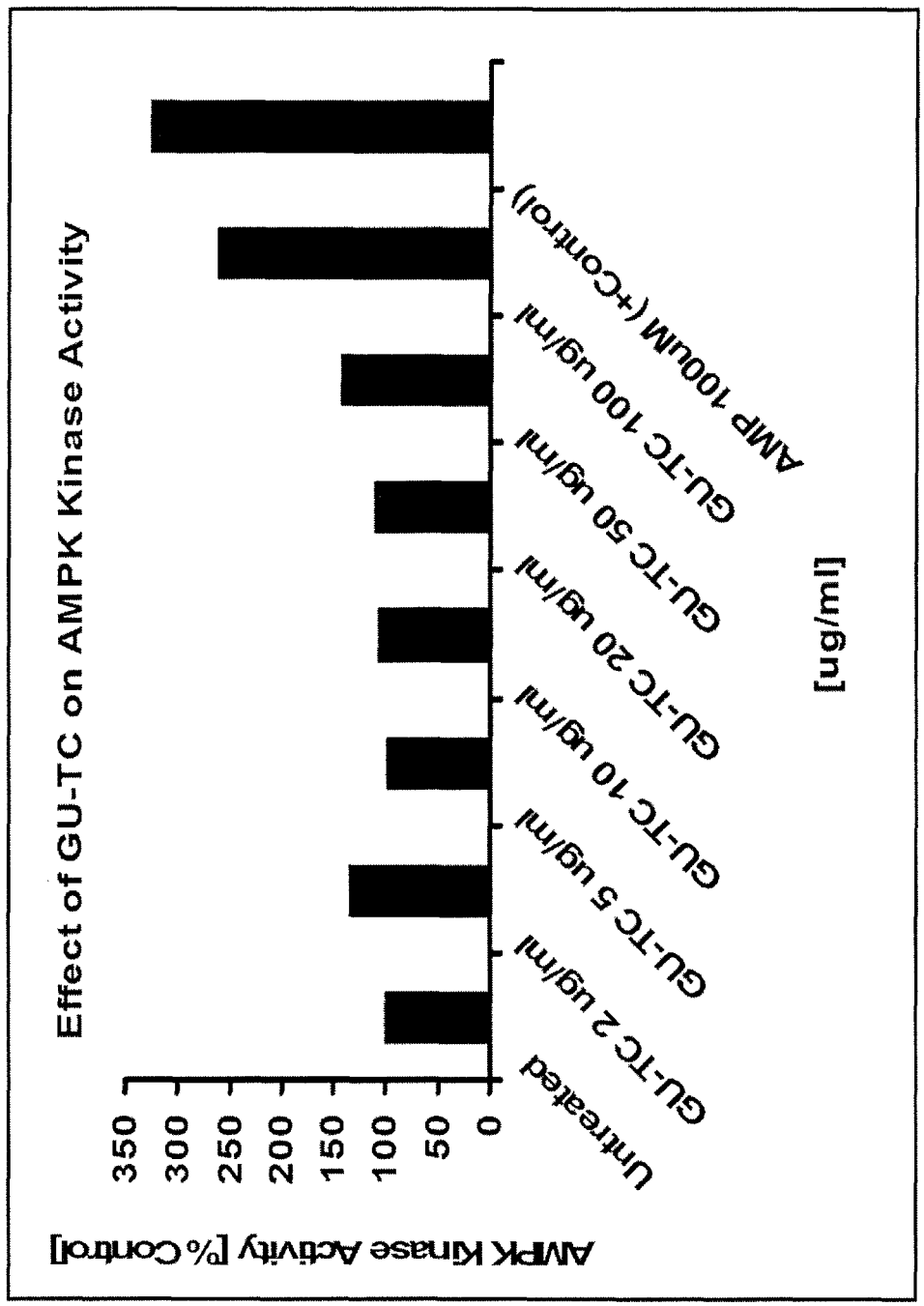
Figure 21:
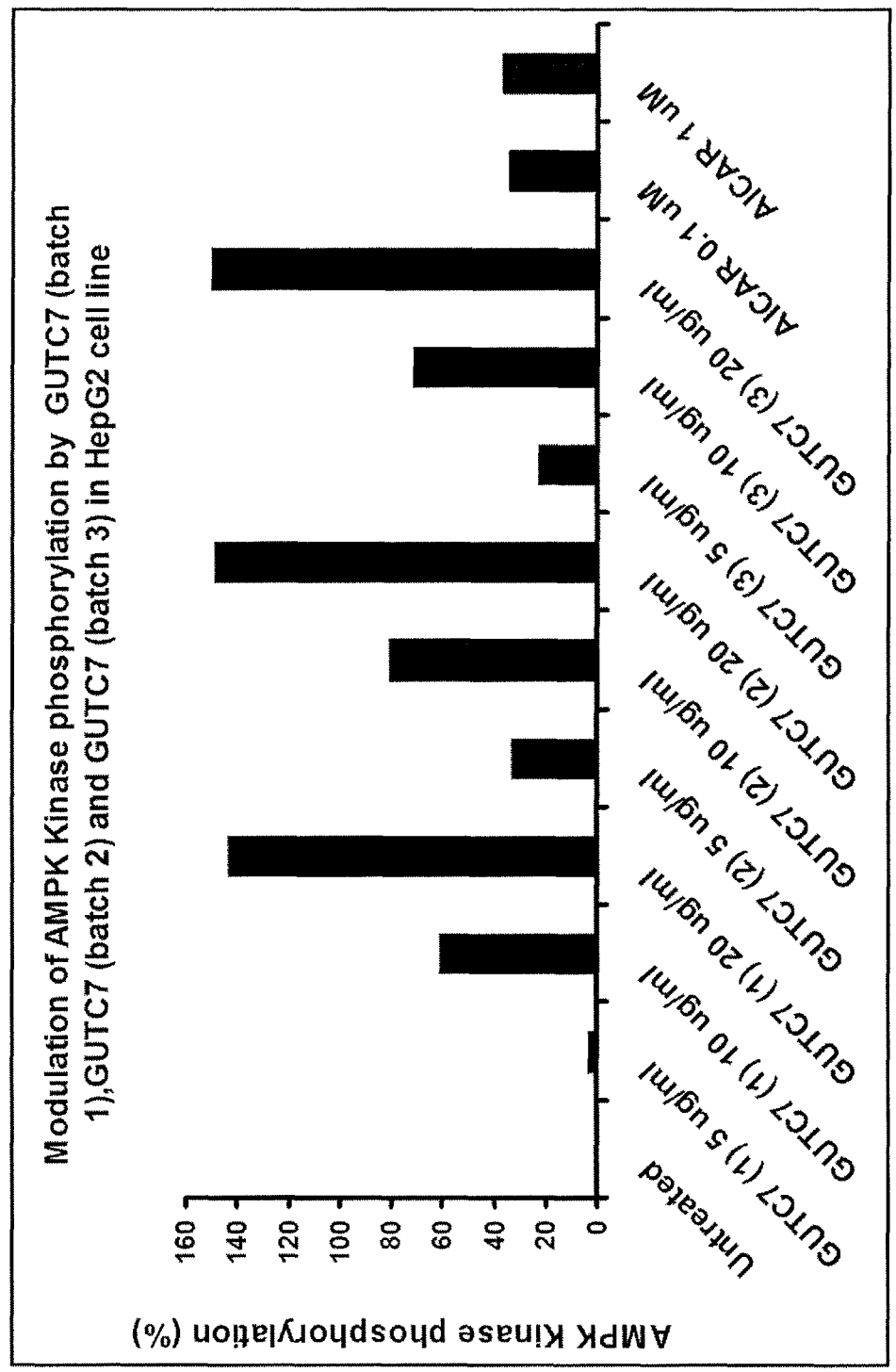
FIG. 21 is a graph showing the effect of four different batches of GU-TC7 on AMPK phosphorylation in HepG2 hepatocytes following treatment with an AMPK inhibitor.

FIG. 18 shows the effect of GU-TC7 on AMPK activity compared to AMP in a cell-free assay. FIG. 19 shows the effect of GU and GU-TC7 on AMPK activity in the 313-L1 preadipocyte cell line. FIG. 20 shows the effect of GU-TC7 on AMPK activity in the 313-L1 preadipocyte cell line. FIG. 21 shows the effect of four different batches of GU-TC7 on AMPK phosphorylation following treatment with an AMPK inhibitor in HepG2 hepatocytes.

Effect of Guggul Extracts on the Cellular NAD/NADH Ratio

Nicotinamide adenine dinucleotide, $NAD^+$, is a coenzyme found in all living cells. There is increasing evidence that $NAD^+$ and NADH play critical roles not only in energy metabolism and mitochondrial functions, but also in cell death, aging and most of the major cellular functions. In the context of metabolic syndrome, increased cellular $NAD^+$ increase regulates various molecular pathways that promote balanced lipid metabolism. It is also a downstream target of the important energy metabolism sensor, AMPK.

Increase in the NAD/NADH ratio occurs via increased NA (Lin A-J, and Guarente L., "Nicotinamide adenine dinucleotide, a metabolic regulator of transcription, longevity and disease," *Curr Opin Cell Biol*, 2003, 15:241-246; Ying W., "$NAD^+$ and NADH in cellular functions and cell death," *Front Biosci.*, 2006, 11:3129-3148; and Ying W., "NAD_/NADH and NADP_/NADPH in cellular functions and cell death: Regulation and biological consequences," *Antioxid. Redox Signal.*, 2008, 10:179-206).

By these last two pathways (stimulation of AMPK and increased NAD/NADH ratio), it is possible to positively influence many major molecular pathways and systems including the endocrine system, inflammatory system, immune system, and more.

Figure 12:
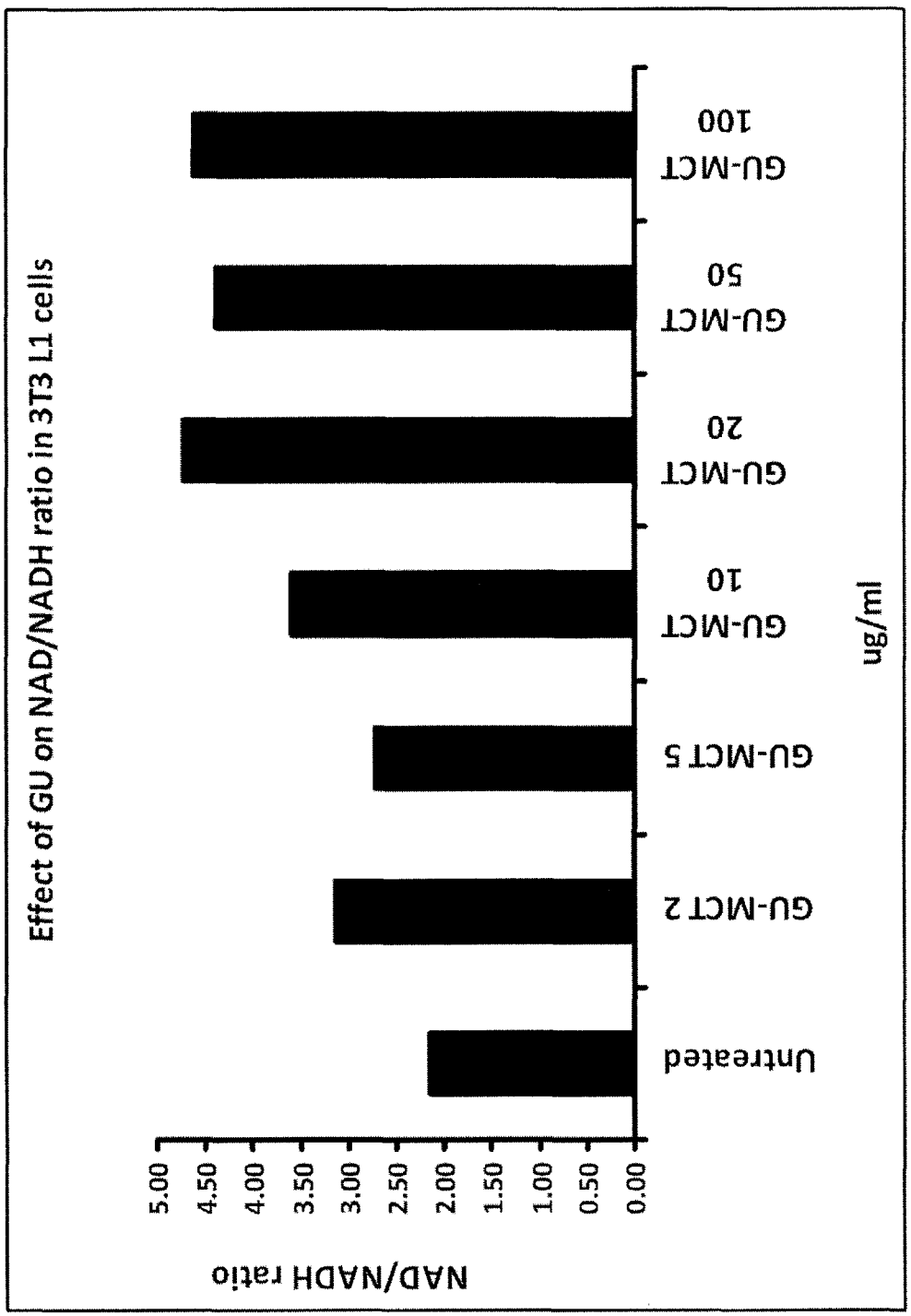
FIG. 12 is a graph showing the effect of GU-MCT810 on the cellular NAD/NADH ratio.
Figure 22:
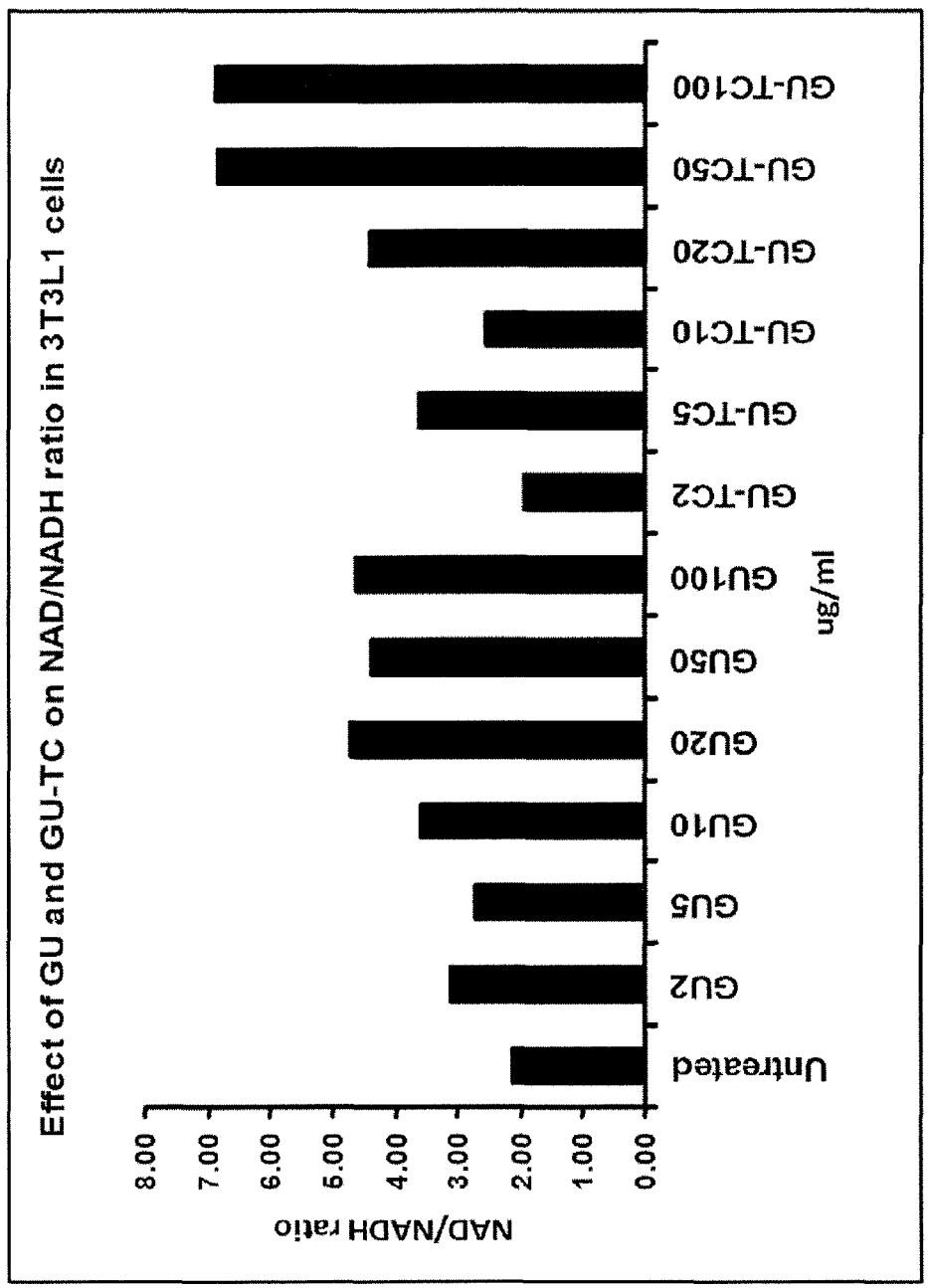
FIG. 22 is a graph showing the effect of GU-TC7 on cellular NAD/NADH ratio.

In the experiment shown in FIG. 12, GU-MCT810 demonstrated the greatest impact on increasing the NAD/NADH ratio. Likewise, in the experiment shown in FIG. 22, GU-TC7 had the greatest effect on NAD/NADH ration.

Effects of Guggul Extracts on Cholesterol

Figure 24:
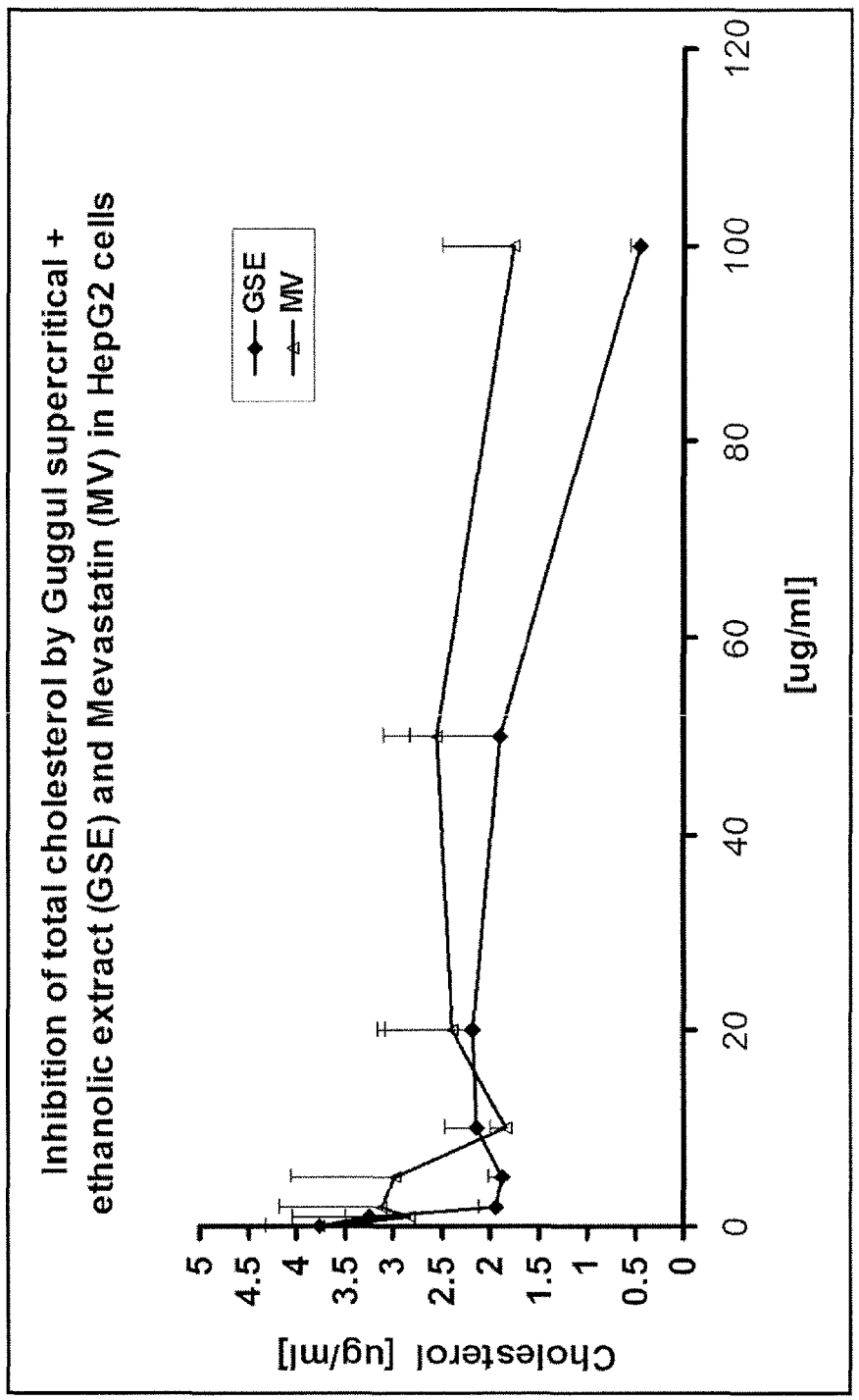
FIG. 24 is a graph showing the effect of guggul supercritical+ethanolic extract (GSE) and Mevastatin (MV) on total cholesterol in HepG2 cells.
Figure 25:
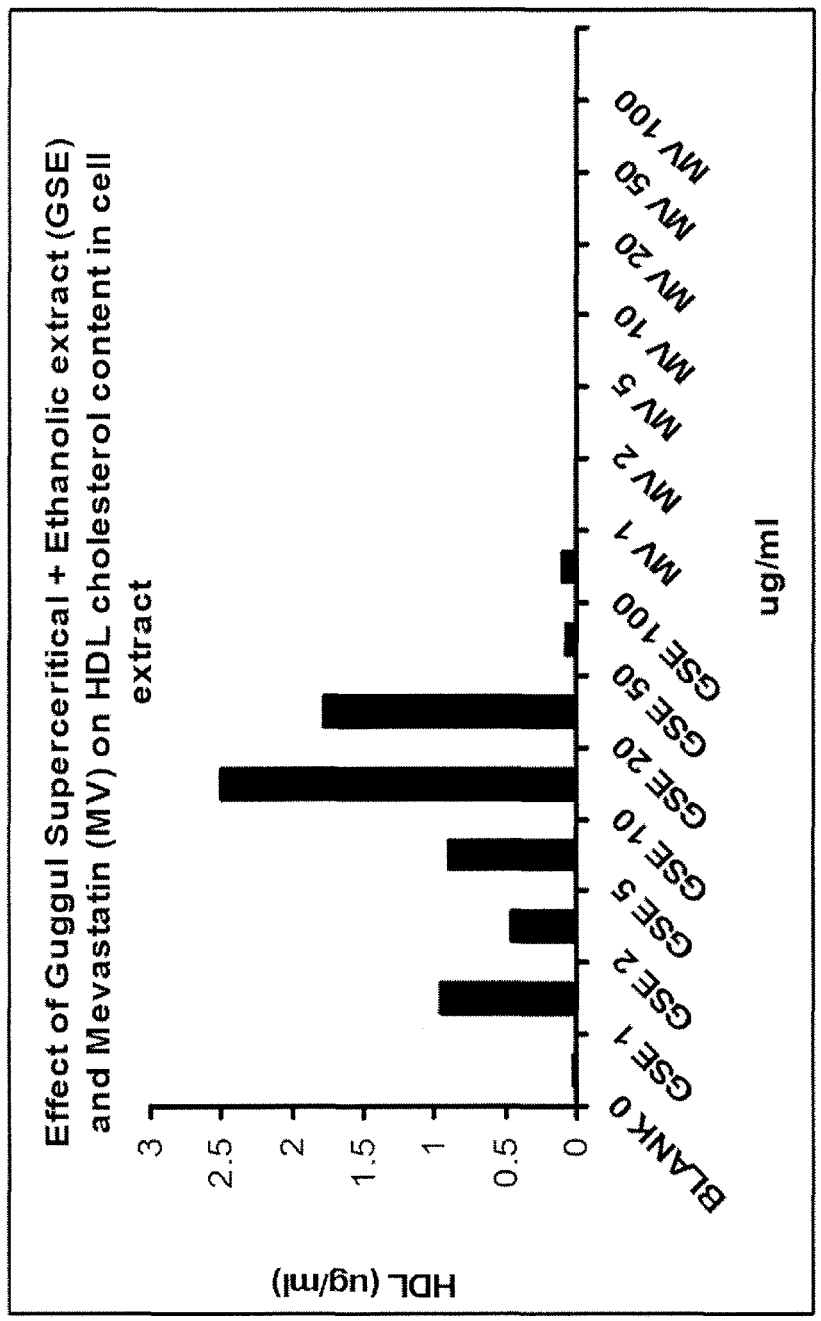
FIG. 25 is a graph showing the effects of GSE and MV on high density lipoprotein (HDL) in cell extracts.
Figure 26:
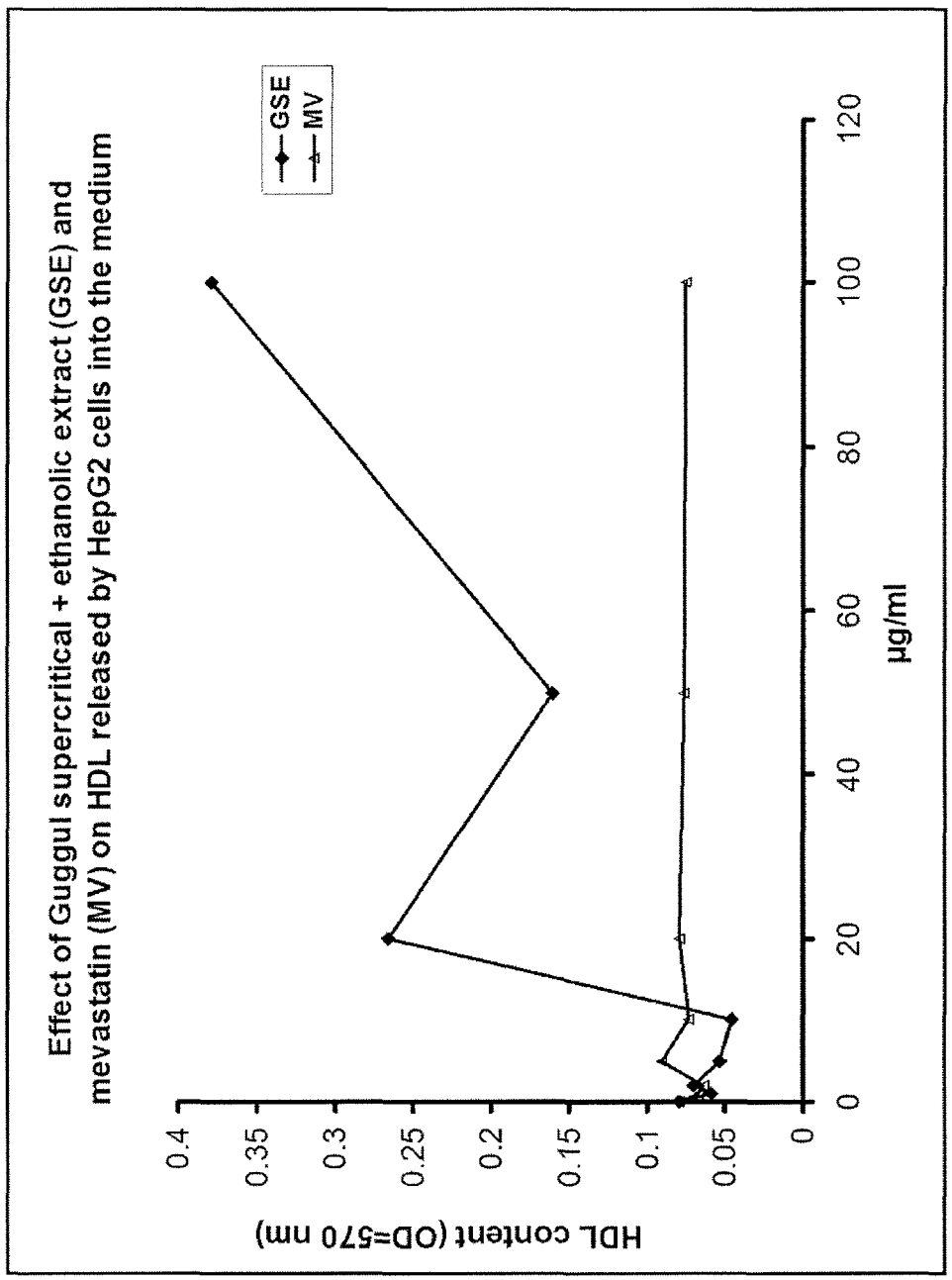
FIGS. 26 and 27 are graphs showing the effects of GSE and MV on HDL (FIG. 26) and LDL (FIG. 27) released by Hep G2 cells into the culture medium.
Figure 27:
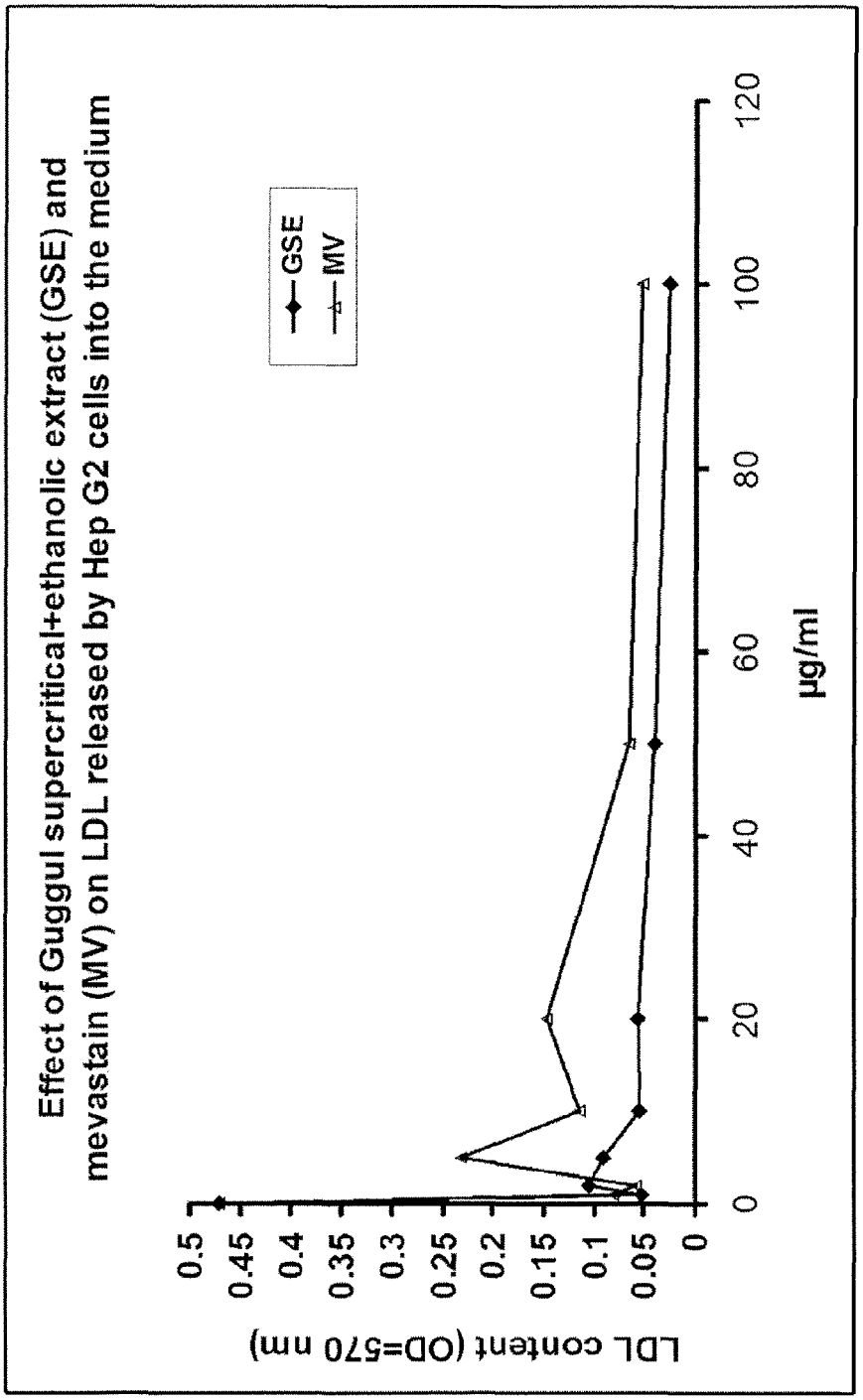

FIG. 24 shows inhibition of total cholesterol by guggul supercritical+ethanolic extract (GSE) and Mevastatin (MV) in HepG2 cells. FIG. 25 shows the effect of GSE and MV on HDL content in cell extract. FIG. 26 shows the effect of GSE and MV on high density lipoprotein (HDL) released by Hep G2 cells into the culture medium. FIG. 27 shows the effect of GSE and MV on low density lipoprotein (LDL) released by Hep G2 cells into the culture medium.

Figure 28:
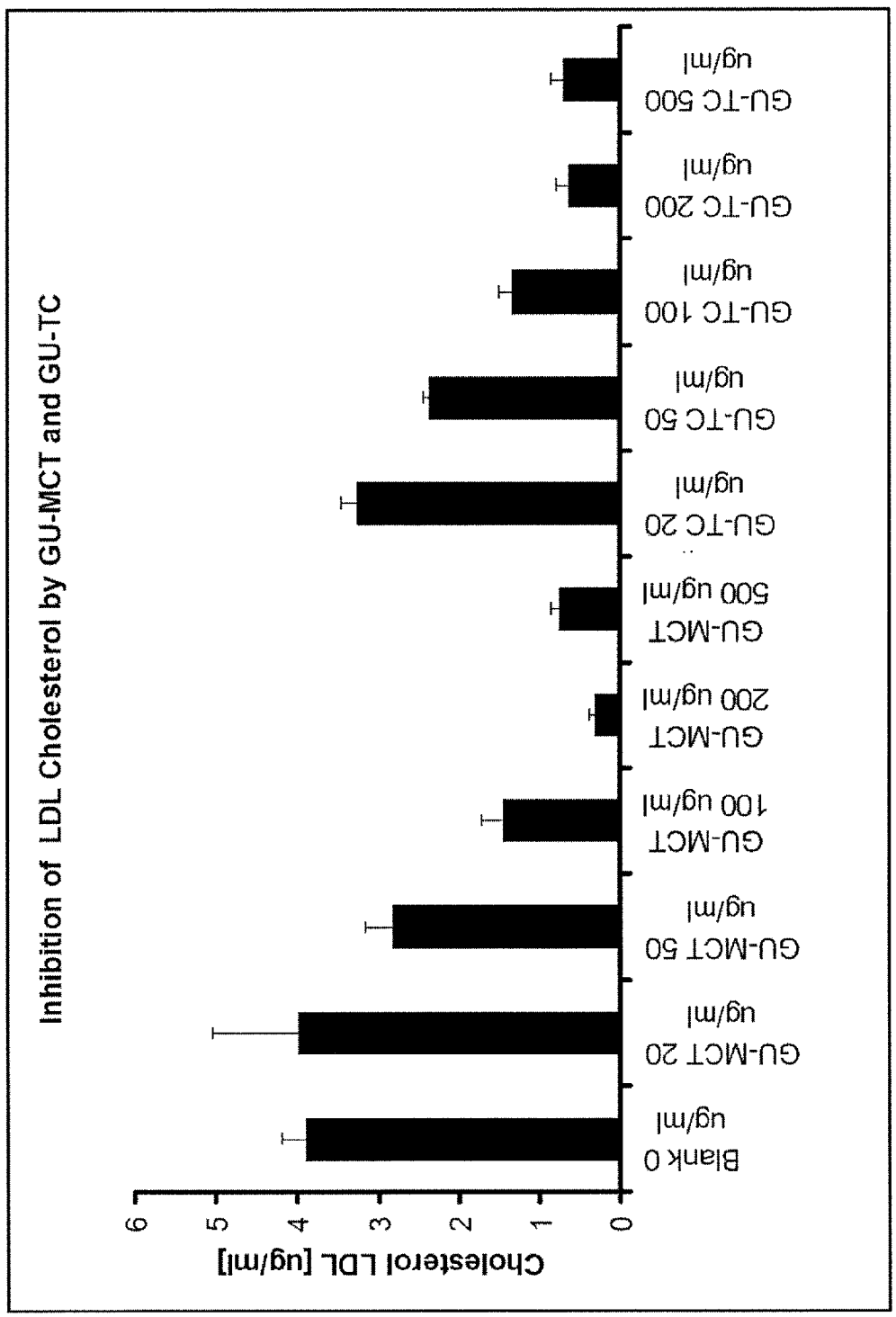
FIGS. 28 and 29 are graphs showing the effects of guggul preparations (GU-MCT810-containing Chia (50:25:25) and Gu-TC7 (50:50)) on LDL (FIG. 29) and HDL (FIG. 30) concentration.
Figure 29:
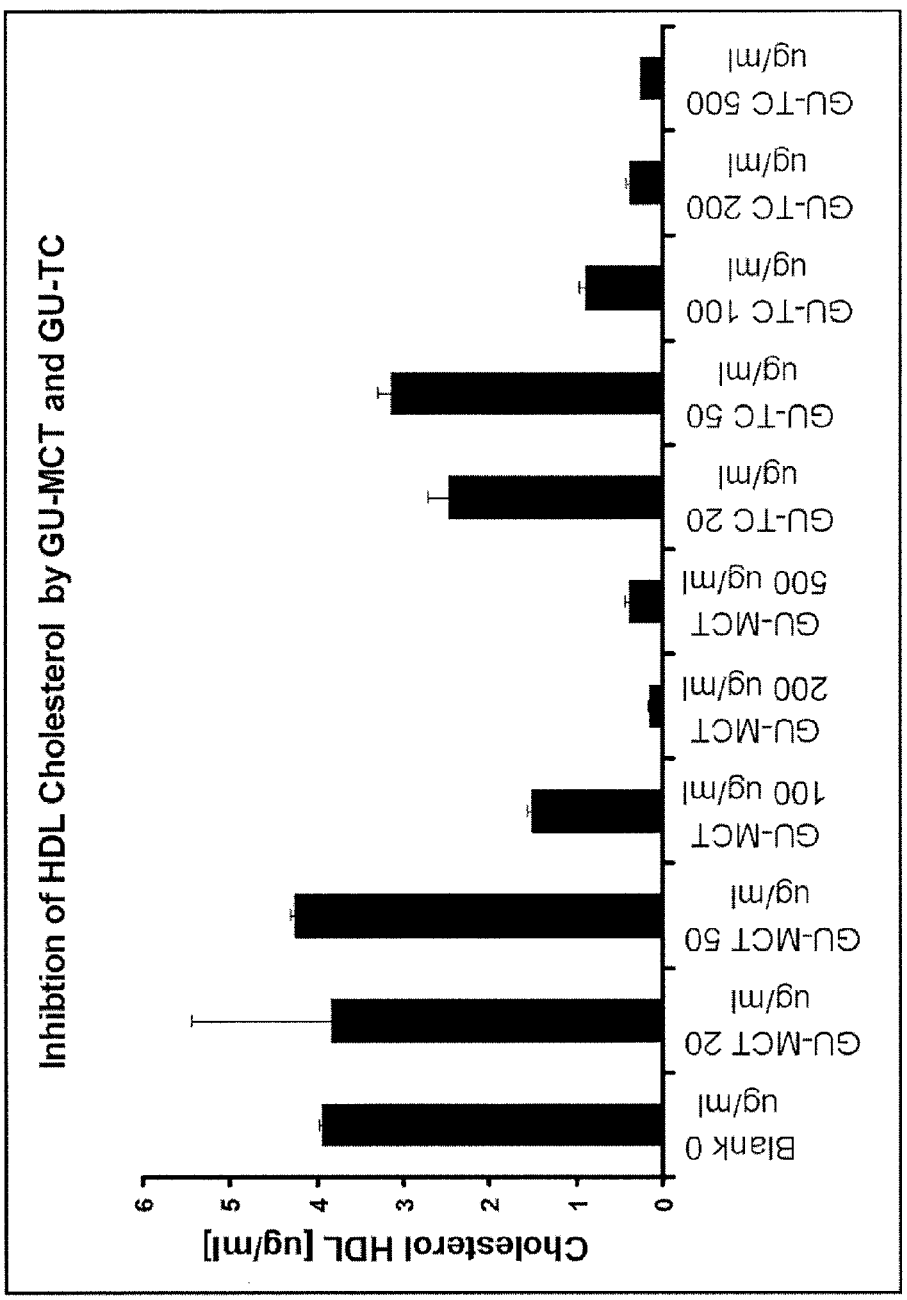

In order to evaluate guggul preparations (GU-MCT810-containing Chia (50:25:25) and Gu-TC7 (50:50) for potential use to treat and/or delay onset of hypercholesterolemia, cell extracts were analyzed for both LDL (FIG. 28) and HDL (FIG. 29) concentration. Inhibition was observed for both preparations, but GU-TC7 performed better. Both these preparations have lowered the LDL and HDL.

Figure 30:
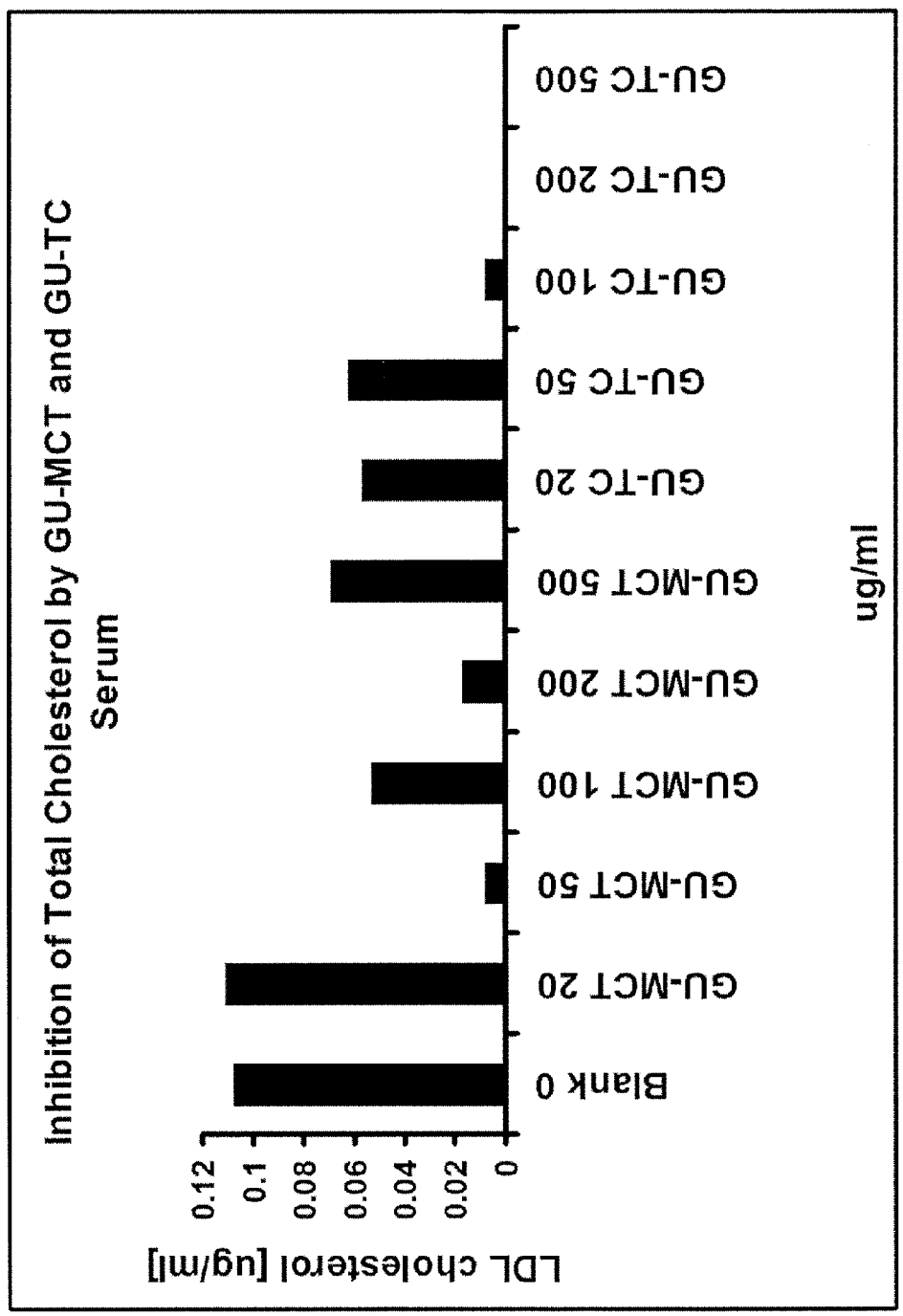
FIGS. 30 and 31 are graphs showing the effects of lower doses of guggul preparations on total cholesterol (FIG. 30) and HDL (FIG. 31) in cell culture medium.
Figure 31:
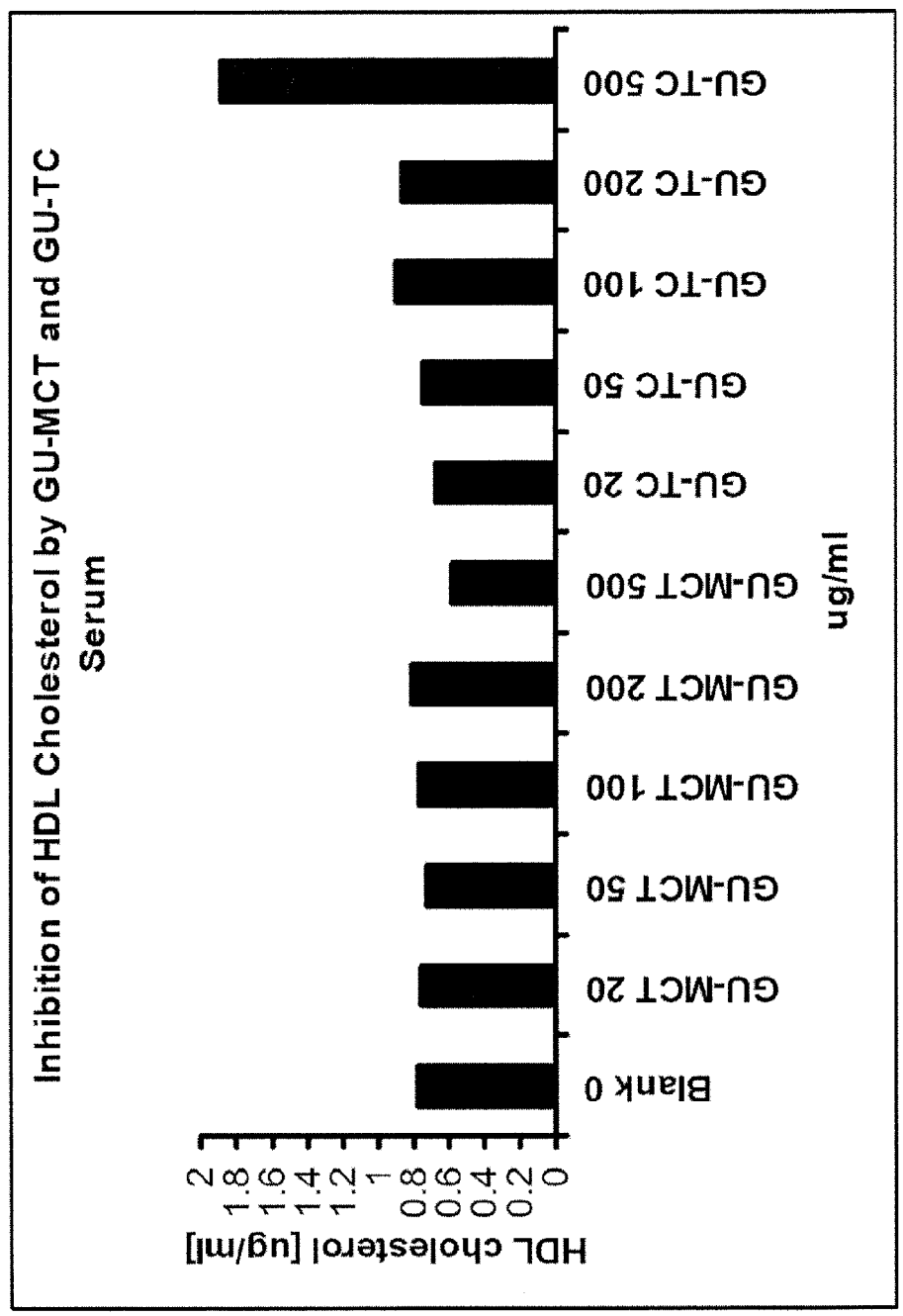
Figure 32:
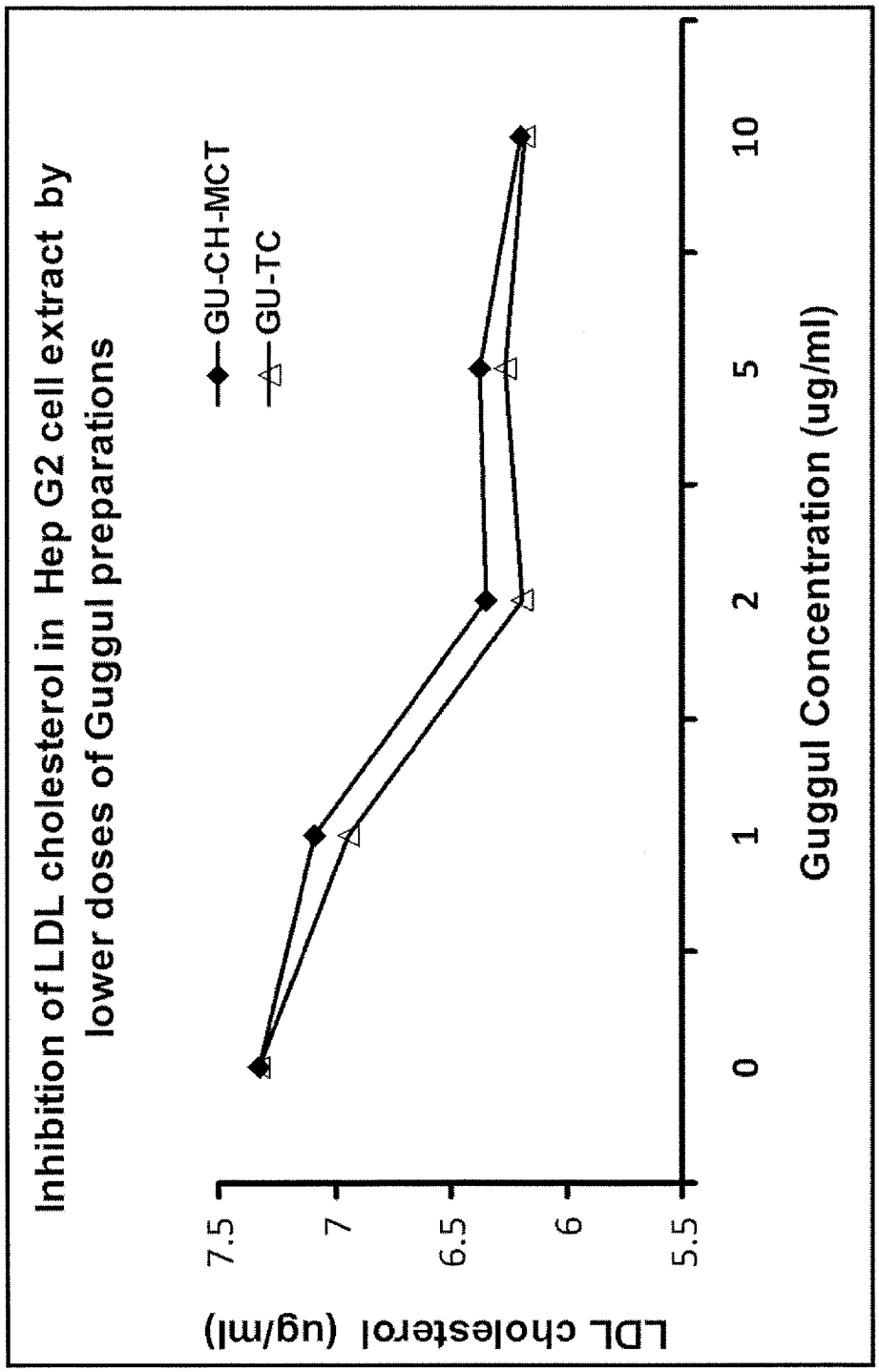
FIGS. 32 and 33 are graphs showing the effects of lower doses of guggul preparations on LDL in HepG2 cell extract and HDL in Hep G2 cells, respectively.
Figure 33:
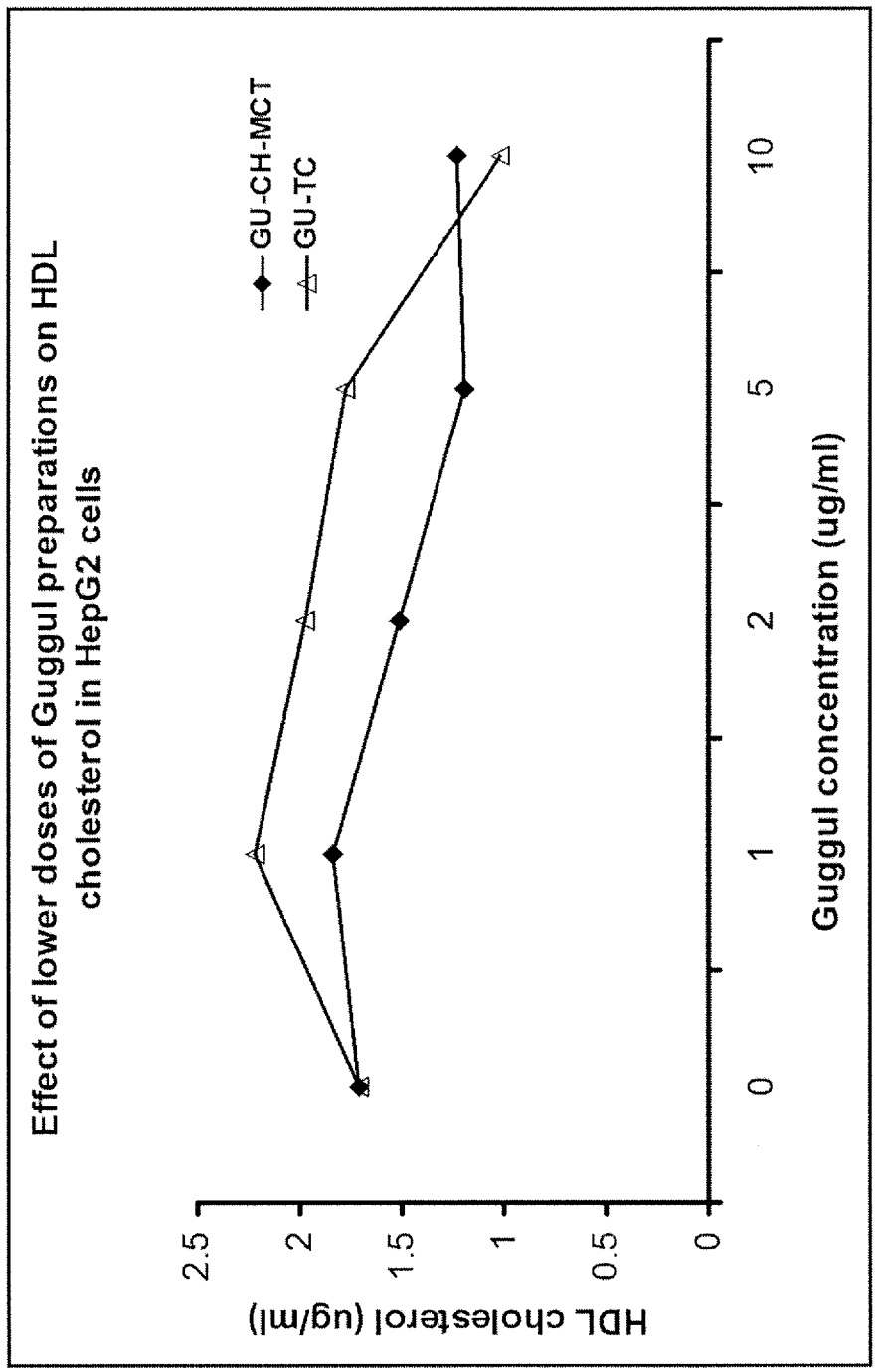

The effects of lower doses of guggul preparations on LDL and HDL were also evaluated. The cell culture medium was analyzed for both LDL and HDL. Inhibition of total cholesterol is shown in FIG. 30. Inhibition of HDL is shown in FIG. 31. The LDL was inhibited but not HDL in the serum. Here again, the GU-TC showed better activity. Interestingly, HDL in the serum was enhanced by the GU-TC. Lower doses of both these agents were used for treating Hep G2 cells for 72 hours and cell extract was analyzed for both LDL and HDL components (FIGS. 32 and 33). Even though the drop is smaller, GU-TC7 showed slightly better results. GU-TC7 elevated HDL initially and then flattened off.

The results disclosed herein indicate inhibition of total cholesterol, LDL, and HMG-CoA reductase activity by GSE. Interestingly, there was enhancement of HDL as analyzed in both cellular extracts and cell culture medium. In contrast, modulation of HDL is not induced by Mevastatin.

Example 4

Adaptogenic Properties of Glucodox (GU-MCT)

Heat shock proteins (HSPs) are ubiquitous and essential to the cells of all organisms and play crucial roles in cellular homeostasis and cell survival in response to a variety of cell stresses. HSPs, a major component of protein chaperones have multiple cellular functions in signal transduction, cell survival and cell death (apoptosis), and protein dynamics (including synthesis, folding, degradation and translocation), intercellular signaling, cellular organization and immunity. They are categorized in families based of their approximate molecular weight (kDa); HSP 40, 60, 70, 90, 100). HSPs are constitutively expressed (5-10% of total protein content) with levels increased up to three-fold times by stress When the cell is under stress arising from oxidation, heat, infection, toxic contamination or any other stressful condition, proteins may unfold and expose residues in their structure that under normal conditions are hidden and shielded from chemical reactions. As a consequence of stress, these residues can easily interact and form aggregates which may harm or even kill the cell (Krebs, 2003). Under such conditions, all cells produce stress proteins to protect the cell from damage. Most well known are the HSPs, a much conserved group of proteins originally discovered in 1962. Stress proteins can help the cell in mainly three respects: down-regulating general protein production; assisting in the refolding of misfolded proteins; and destroying misfolded proteins.

The adaptogenic properties of the composition (GU-MCT) in general include supporting and restoring of cellular stress response mechanisms, increasing resistance to a broad spectrum of stressors, and increasing stress response capacity (stress tolerance/conditioning). The effect on HSPs is but one among other mechanisms that reflect adaptogenic properties.

Materials and Methods

A human liver cell line (HepG2) was used to study the expression of HSP70 in GU-MCT treated cells. The cells ($2\times10^6/4$ ml) were grown in Eagles minimal essential medium and treated with 50 μM Menadione (Vitamin K analogue) for 3 hours in order to induce stress in the presence or absence of increasing concentrations of GU-MCT (0-100 μg/ml). The cells were harvested by scraping and cell lysate prepared by homogenizing cells in 0.5 ml of lysis buffer (R&D systems, Minneapolis, Minn.). Protein concentration of cell lysate was estimated and 10 μg protein was used for ELISA. The ELISA kit from R&D systems, MN was used to analyze the HSP70 protein expression (pg/ml) in the cell extract. The percentage of change in HSP70 expression was calculated based on the expression in untreated sample (100%).

Results

Figure 34:
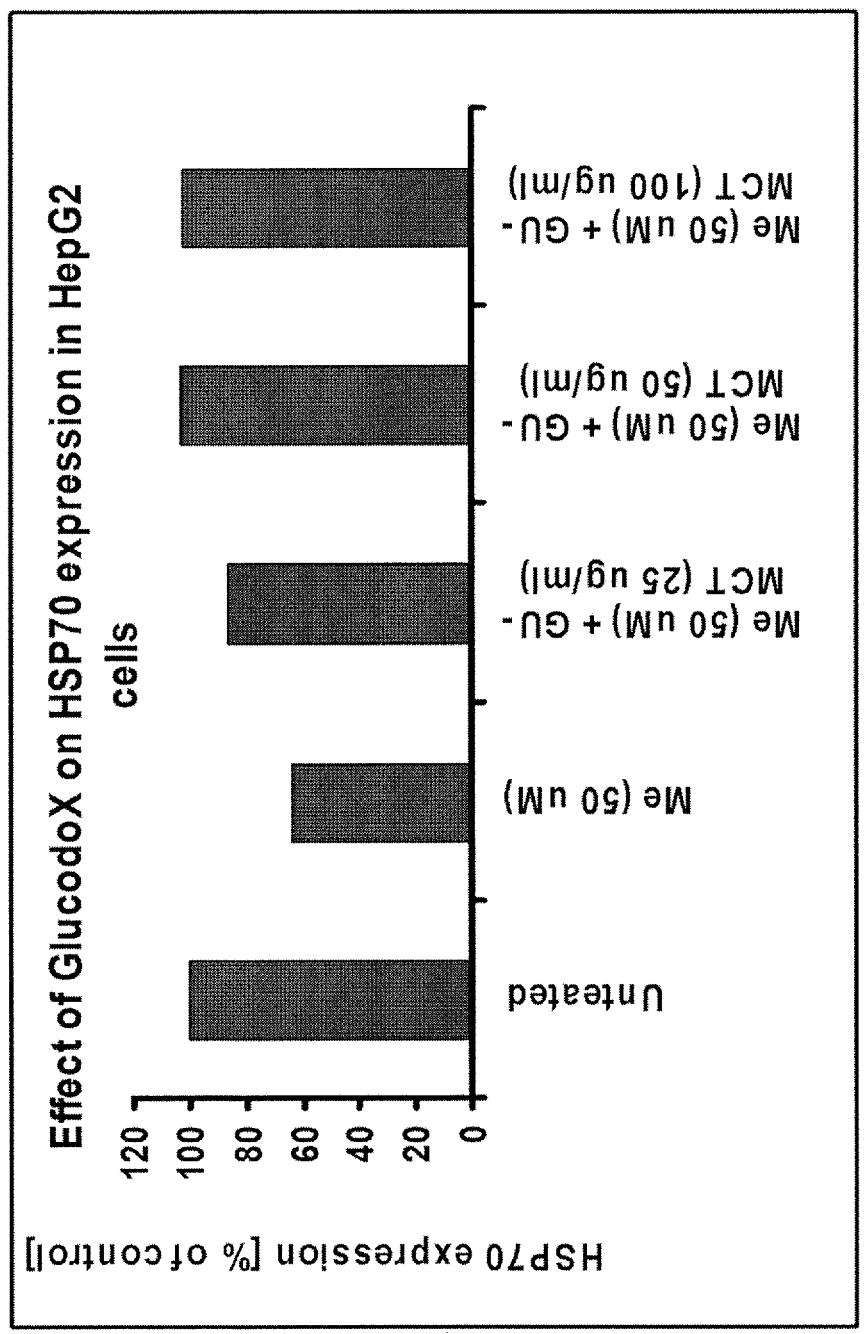
FIG. 34 is a graph showing reversal of Menadione-induced down regulation of heat shock protein 70 (HSP70) expression in HepG2 cells upon treatment with GU-MCT.

HSP70 expression was significantly down regulated (40%) by Menadione (50 μM) treatment for 3 hours (FIG. 34). GU-MCT treatment reversed the Menadione induced-inhibition of HSP70. Complete restoration was established at 50 μg/ml GU-MCT treatment.

Example 5

Anti-Aging Properties of Glucodox (GU-MCT)

Recent research has revealed roles for the protein kinase termed "the target of rapamycin" (TOR) in modulating lifespan, and for two of the processes which TOR regulates, i.e., protein synthesis and autophagy. Studies in diverse model organisms have shown that impairment of TOR signaling leads to increased life span (longevity). mTOR, a serine/threonine kinase, is phosphorylated in the active form. There is overwhelming evidence that cellular mechanisms and signaling pathways regulating aging are controlled by mTOR. The present inventors have analyzed the inhibition of the phosphorylated form of mTOR by GU-MCT in human liver cells (HepG2) using the phospho-TOR immunoassay (R&D systems, Minneapolis, Minn.).

Materials and Methods

HepG2 (human hepatoma) cells ($2 \times 10^6$ cells/4 ml) were treated with increasing concentrations of GU-MCT (0-100 ug/ml) for 72 h and cell extract was prepared by homogenizing cells in lysis buffer (R&D Systems, Minneapolis, Minn.). The protein concentration of cell extracts were estimated and cell extract equivalent to 100 ug protein was used for ELISA. Phospho-TOR immunoassay kit from R&D Systems, Minneapolis, Minn. was analysis of mTOR expression (pg/ml) in the cell extract. The percentage change in phospho-mTOR expression was calculated based on the expression in untreated sample (100%).

Results

Figure 35:
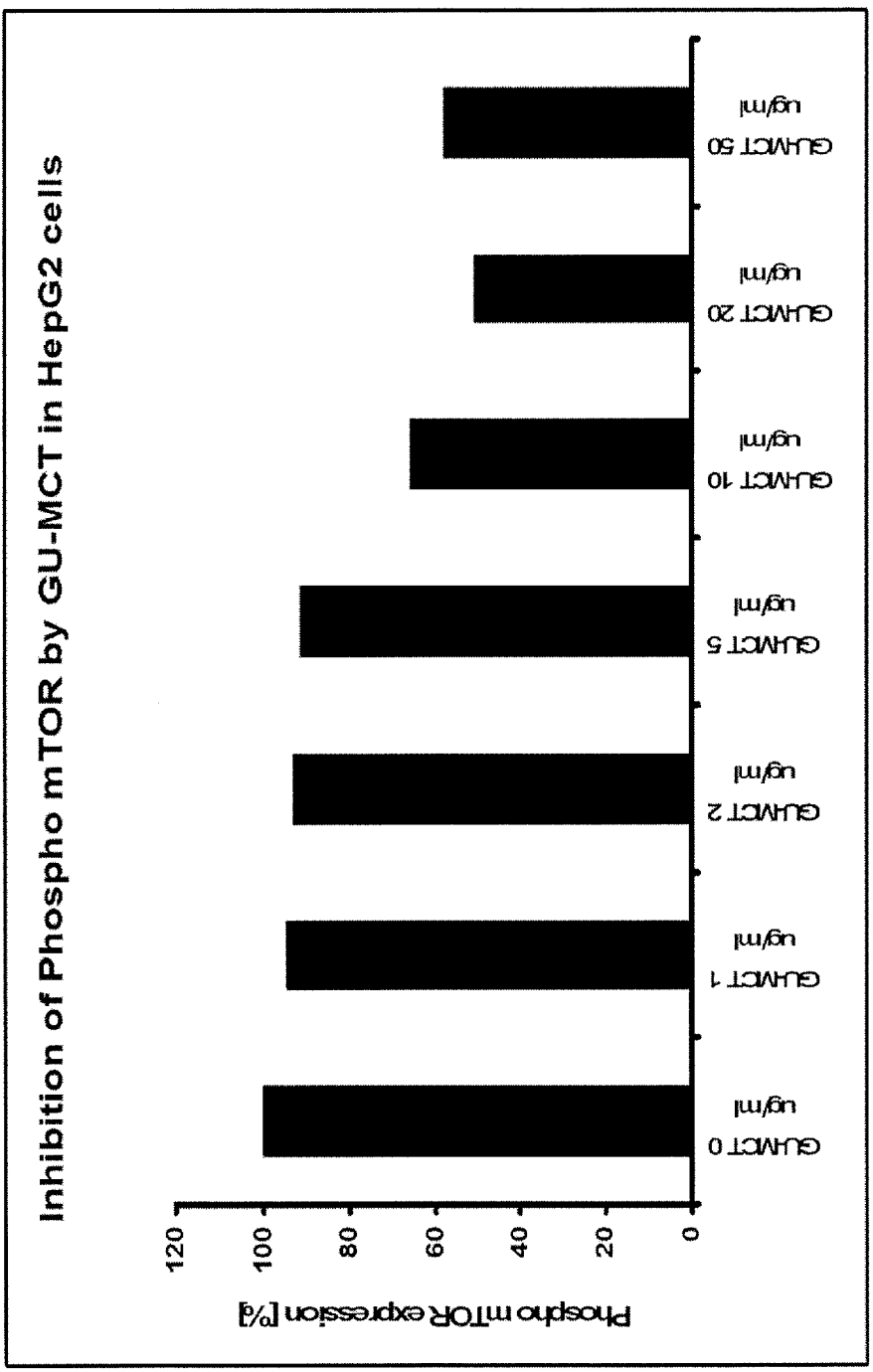
FIGS. 35 and 36 are graphs showing inhibition of phosphorylated mammalian target of rapamycin (phospho mTOR) in HepG2 cells upon treatment with GU-MCT (72-hour and 48-hour exposure, respectively).
Figure 36:
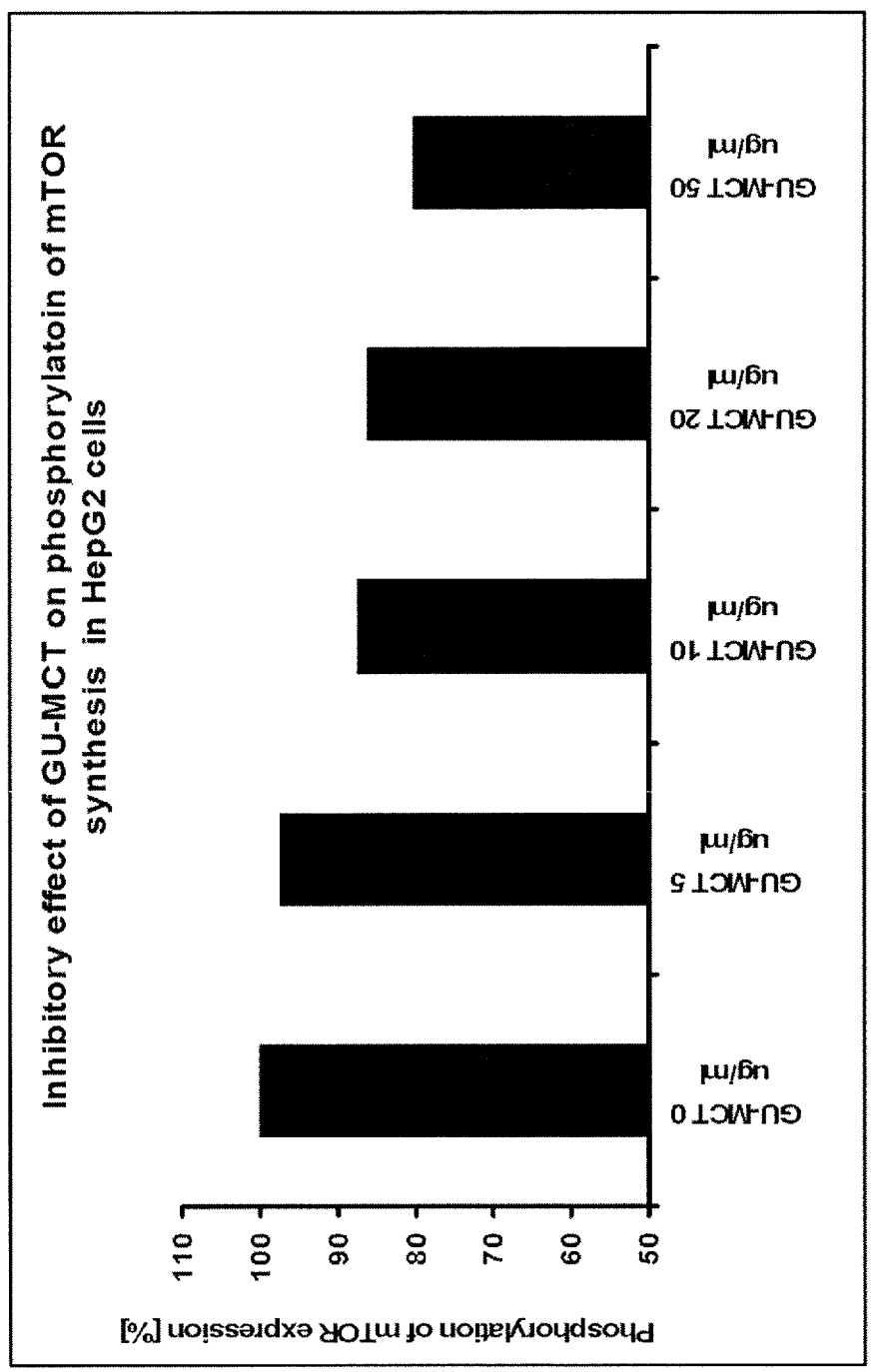

Treatment of HepG2 cells with GU-MCT for 72 hours inhibits phosphorylated mTOR expression significantly. About 50% inhibition in phospho-mTOR expression was observed by 20 μg/ml GU-MCT treatment (FIG. 35). FIG. 36 shows results of treatment with GU-MCT for 48 hours. This reduction in mTOR expression may have significance in AMPK expression and the anti-aging property of the compositions of the invention.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method for stimulating phosphorylation of AMP-activated protein kinase (AMPK) in a target cell of a human or non-human animal subject having a disorder associated with suppression of AMPK, comprising contacting the target cell with a composition in vivo, wherein the composition comprises an effective amount of a supercritical carbon dioxide extract of *Commiphora mukul* resin (guggul) and an effective amount of one or more medium chain triglycerides, wherein the carbon dioxide is modified by ethanol addition, and wherein said contacting increases phosphorylation of AMPK in the target cell.

2. The method of claim 1, wherein the one or more medium chain triglycerides comprise C8 and C10 fatty acids.

3. The method of claim 1, wherein the composition contains 0.1%-5% guggulsterone (total E and Z guggulsterones).

4. The method of claim 3, wherein the composition comprises 1.5%-3% guggulsterone (total E and Z guggulsterones).

5. The method of claim 3, wherein the composition comprises 1.9%-2.1% guggulsterones (by HPLC); 6%-9% phytosterol; essential oil; cembrene; mukulol (allycembrol); and less than 3% ethanol.

6. The method of claim 1, wherein the composition further comprises a botanical extract selected from among a sterol, sterone, steroid, polyphenol, flavonoid, terpenoid, alkaloid, or a polysaccharide.

7. The method of claim 1, wherein said contacting comprises administering the composition to the subject, and wherein the composition is orally administered to the subject.

8. The method of claim 1, wherein said contacting comprises administering the composition to the subject, and wherein the composition is topically administered to the subject.

9. The method of claim 1, wherein the target cell is a cancer cell.

10. The method of claim 1, wherein the disorder is selected from among hypercholesterolemia, hyperlipidemia, hyperglycemia, obesity, metabolic syndrome, cardiovascular disease, atherosclerotic heart disease, autoimmune disorder, insulin resistance, leptin resistance, arthritis, cell proliferation disorder, damaged skin, sore, cut, rash, bruise, dryness, burn, sunburn, radiation burn, and infection.

11. The method of claim 1, wherein the subject is human.

12. The method of claim 1, wherein the subject is a non-human animal.

13. The method of claim 1, wherein one or more of the following occur in the contacted target cell: inhibition of production of phosphorylated mechanistic target of rapamycin (mTOR), increase in NAD$^+$ and NAD/NADH ratio, up-regulation of NAD-dependent deacetylase sirtuin-1 (SIRT-1), up-regulation of FOXO transcription factors, up-regulation of peroxisome proliferator-activated receptor gamma coactivator-1 alpha (PGC-1α), and up-regulation of peroxisome proliferator-activated receptor gamma (PPARγ).

14. The method of claim 1, wherein one or more of the following occur in the contacted target cell: inhibition of HMG-CoA reductase, inhibition of adipocyte differentiation, increased glucose uptake, inhibition of alpha-glucosidase, and promotion of heat shock protein production.

15. The method of claim 1, wherein one or more of the following occur in the contacted target cell: inhibition of matrix metalloproteinase-1 (MMP-1), increase of collagen type I synthesis, and inhibition of polymorphonuclear (PMN) elastase.

16. The method of claim 1, wherein the one or more medium chain triglycerides comprise triheptanoin.

17. The method of claim 1, wherein the disorder is a cancer or other cell proliferation disorder.

18. The method of claim 1, wherein the disorder is cardiovascular disease.

19. The method of claim 1, wherein the disorder is type 2 diabetes, insulin resistance, or leptin resistance.

20. The method of claim 1, wherein the disorder is obesity.

21. The method of claim 1, wherein the disorder is metabolic syndrome.

22. The method of claim 1, wherein the disorder is inflammation.

23. The method of claim 1, wherein the disorder is an infection.

24. The method of claim 1, wherein the disorder is damaged or aged skin.

25. The method of claim 1, wherein said contacting comprises administering the composition to the subject, and wherein the composition is administered in solid form.

26. The method of claim 1, wherein said contacting comprises administering the composition to the subject, and wherein the composition is administered in liquid form.

27. The method of claim 1, wherein said contacting comprises administering the composition to the subject, and wherein the composition is administered in semi-solid form.

28. The method of claim 1, wherein said contacting comprises administering the composition to the subject, and wherein the composition is administered in the form of a micro-emulsion, micro-encapsulation, nano-emulsion, nano-encapsulation, or liposomal preparation.

29. The method of claim 1, wherein said contacting comprises administering the composition to the subject, and wherein the composition is administered sublingually.

* * * * *

UNITED STATES PATENT AND TRADEMARK OFFICE
CERTIFICATE OF CORRECTION

PATENT NO. : 9,913,870 B2
APPLICATION NO. : 14/368888
DATED : March 13, 2018
INVENTOR(S) : Steven J. Melnick et al.

Page 1 of 1

It is certified that error appears in the above-identified patent and that said Letters Patent is hereby corrected as shown below:

In the Specification

Column 4,
Line 16, "hill oil" should read --krill oil--.

Column 27,
Line 25, "Later, 50 mL" should read --Later, 50 µL--.

Column 28,
Line 2, "10 µmL$^{-1}$" should read --10 µg mL$^{-1}$--.

Column 33,
Line 25, "NAD" should read --NAD$^+$--.

Signed and Sealed this
Sixth Day of November, 2018

Andrei Iancu
*Director of the United States Patent and Trademark Office*